US010836029B2

(12) United States Patent
Mahoney et al.

(10) Patent No.: US 10,836,029 B2
(45) Date of Patent: Nov. 17, 2020

(54) EXOSUIT LOAD BEARING DISTRIBUTION SYSTEMS

(71) Applicant: SEISMIC HOLDINGS, INC., Menlo Park, CA (US)

(72) Inventors: Richard Mahoney, Menlo Park, CA (US); Katherine Goss Witherspoon, Menlo Park, CA (US)

(73) Assignee: SEISMIC HOLDINGS, INC., Menlo Park, CA (US)

( * ) Notice: Subject to any disclaimer, the term of this patent is extended or adjusted under 35 U.S.C. 154(b) by 201 days.

(21) Appl. No.: 16/203,220

(22) Filed: Nov. 28, 2018

(65) Prior Publication Data

US 2019/0160652 A1    May 30, 2019

Related U.S. Application Data

(60) Provisional application No. 62/591,739, filed on Nov. 28, 2017, provisional application No. 62/644,301, (Continued)

(51) Int. Cl.
*B25J 9/00* (2006.01)
*A61H 3/00* (2006.01)
(Continued)

(52) U.S. Cl.
CPC ............... *B25J 9/0006* (2013.01); *A61F 2/68* (2013.01); *A61H 3/00* (2013.01); *A61B 5/1114* (2013.01);
(Continued)

(58) Field of Classification Search
CPC ........ B25J 9/0006; B25J 9/104; B25J 9/1633; A61F 2/68; A61H 3/00; A61H 2201/1616;
(Continued)

(56) References Cited

U.S. PATENT DOCUMENTS 9,089,173 B2    7/2015 Krishnan
9,351,900 B2 *  5/2016 Walsh .................... B25J 9/0006
(Continued)

FOREIGN PATENT DOCUMENTS

WO    2016/138264 A1    9/2016
WO    2017/026943 A1    2/2017
WO    2017/160751 A1    9/2017

OTHER PUBLICATIONS

Home Brew Robotics Club Meeting—Feb. 2016—Talk2: SRI Robotics, published Mar. 2, 2016, https://www.youtube.com/watch?v=UzpisQq0I3U (2 pages).

*Primary Examiner* — Suba Ganesan
*Assistant Examiner* — Aren Patel
(74) *Attorney, Agent, or Firm* — Van Court & Aldridge LLP

(57) ABSTRACT

Exosuit systems may be assistive, as it physically assists the wearer in performing particular activities, or can provide other functionality such as communication to the wearer through physical expressions to the body, engagement of the environment, or capturing of information from the wearer. In order to transmit assistance to the user of the exosuit, loads need to be translated by the exosuit. This is can be through the use of load distribution members. Load distribution members can be placed around the pelvis, waist, thighs, and other body parts.

19 Claims, 88 Drawing Sheets

Related U.S. Application Data filed on Mar. 16, 2018, provisional application No. 62/724,452, filed on Aug. 29, 2018.

(51) Int. Cl.
| | |
|---|---|
| *A61F 2/68* | (2006.01) |
| *B25J 9/10* | (2006.01) |
| *B25J 9/16* | (2006.01) |
| *A63B 21/00* | (2006.01) |
| *A61B 5/11* | (2006.01) |

(52) U.S. Cl.
CPC ....... *A61F 2002/6827* (2013.01); *A61H 2201/163* (2013.01); *A61H 2201/165* (2013.01); *A61H 2201/1616* (2013.01); *A61H 2201/1626* (2013.01); *A61H 2201/1642* (2013.01); *A61H 2201/1659* (2013.01); *A61H 2201/5023* (2013.01); *A61H 2201/5038* (2013.01); *A61H 2201/5061* (2013.01); *A61H 2201/5069* (2013.01); *A61H 2201/5079* (2013.01); *A63B 21/4039* (2015.10); *A63B 21/4043* (2015.10); *A63B 2209/10* (2013.01); *B25J 9/104* (2013.01); *B25J 9/1633* (2013.01); *G05B 2219/39345* (2013.01); *G05B 2219/40305* (2013.01)

(58) Field of Classification Search
CPC .... A61H 2201/1676; A61H 2201/1626; A61H 2201/163; A61H 2201/165; A61H 2201/1659; A61H 2201/5023; A61H 2201/5038; A61H 2201/5061; A61H 2201/5079; A63B 21/4039; A63B 21/4043

See application file for complete search history.

(56) References Cited

U.S. PATENT DOCUMENTS

| | | | |
|---|---|---|---|
| 2004/0230150 A1* | 11/2004 | West | A61H 3/008 602/19 |
| 2005/0130815 A1* | 6/2005 | Abdoli-Eramaki | A61H 3/008 482/121 |
| 2007/0265140 A1 | 11/2007 | Kim et al. | |
| 2013/0288863 A1 | 10/2013 | Yamamoto et al. | |
| 2014/0277739 A1* | 9/2014 | Kornbluh | A41D 13/002 700/260 |
| 2015/0216756 A1* | 8/2015 | Yamamoto | A61H 3/00 601/134 |
| 2016/0107309 A1* | 4/2016 | Walsh | A61H 3/00 248/550 |
| 2016/0213548 A1 | 7/2016 | John et al. | |
| 2019/0290466 A1* | 9/2019 | Nishi | A61F 5/01 |

\* cited by examiner

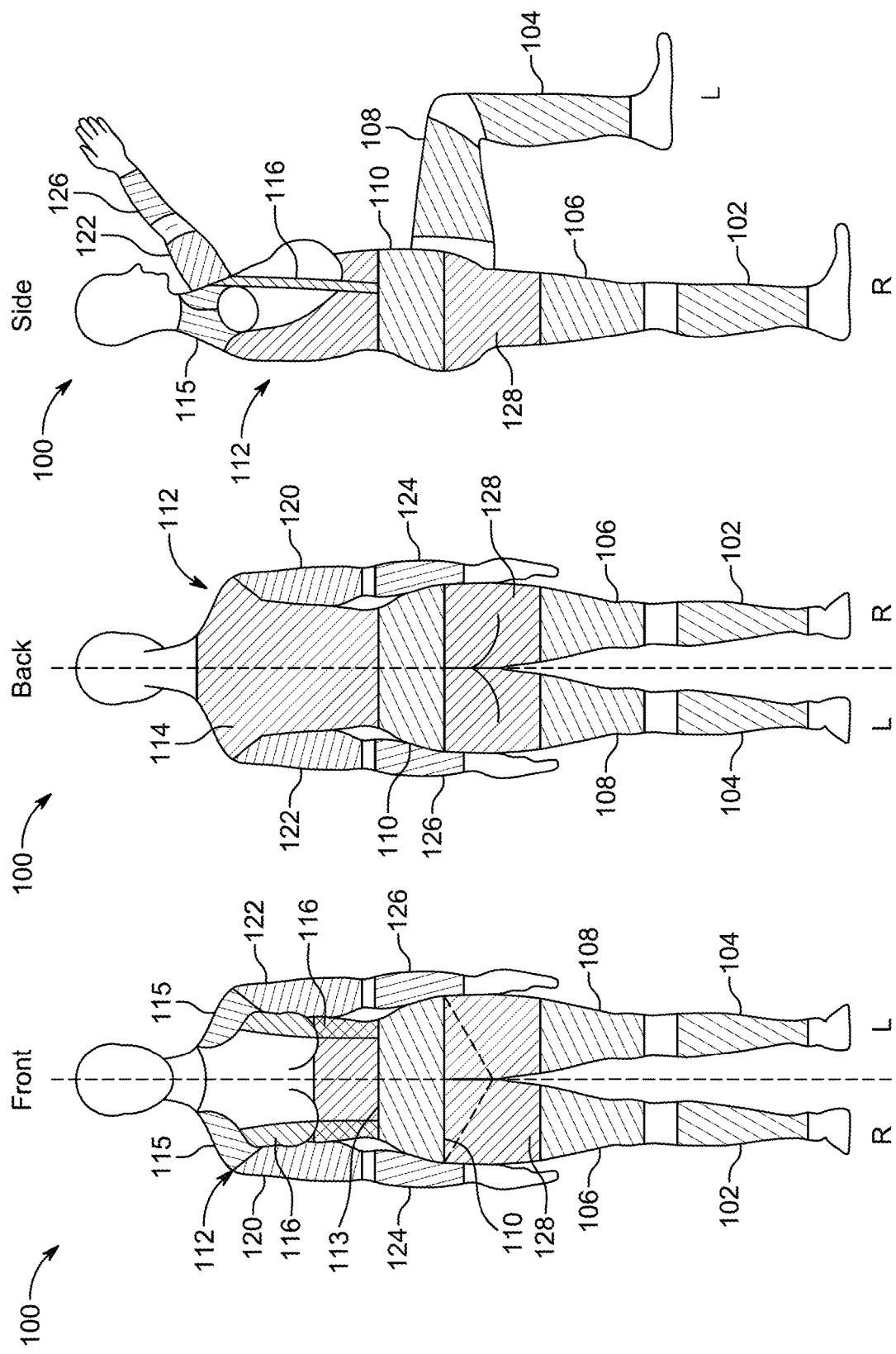

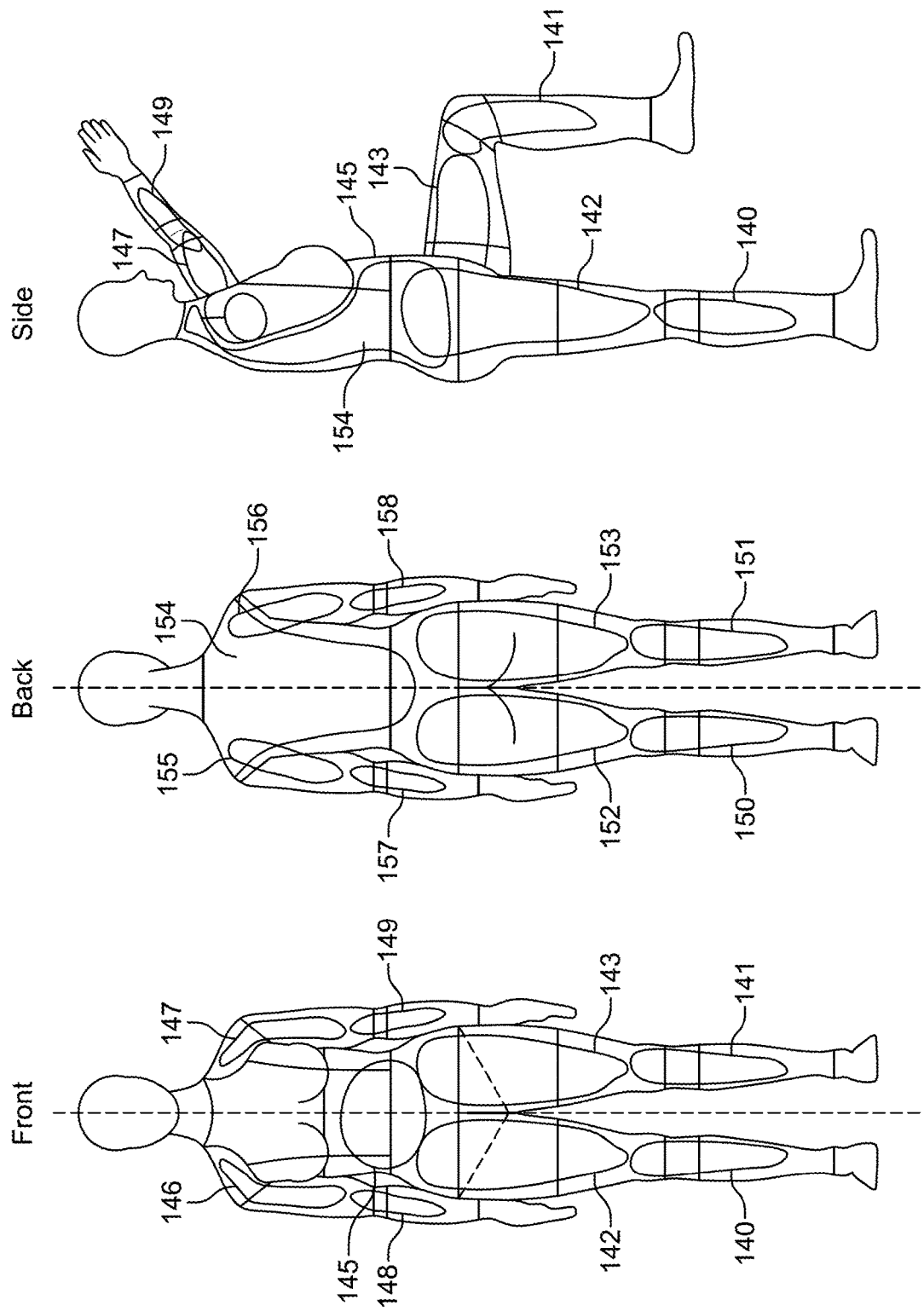

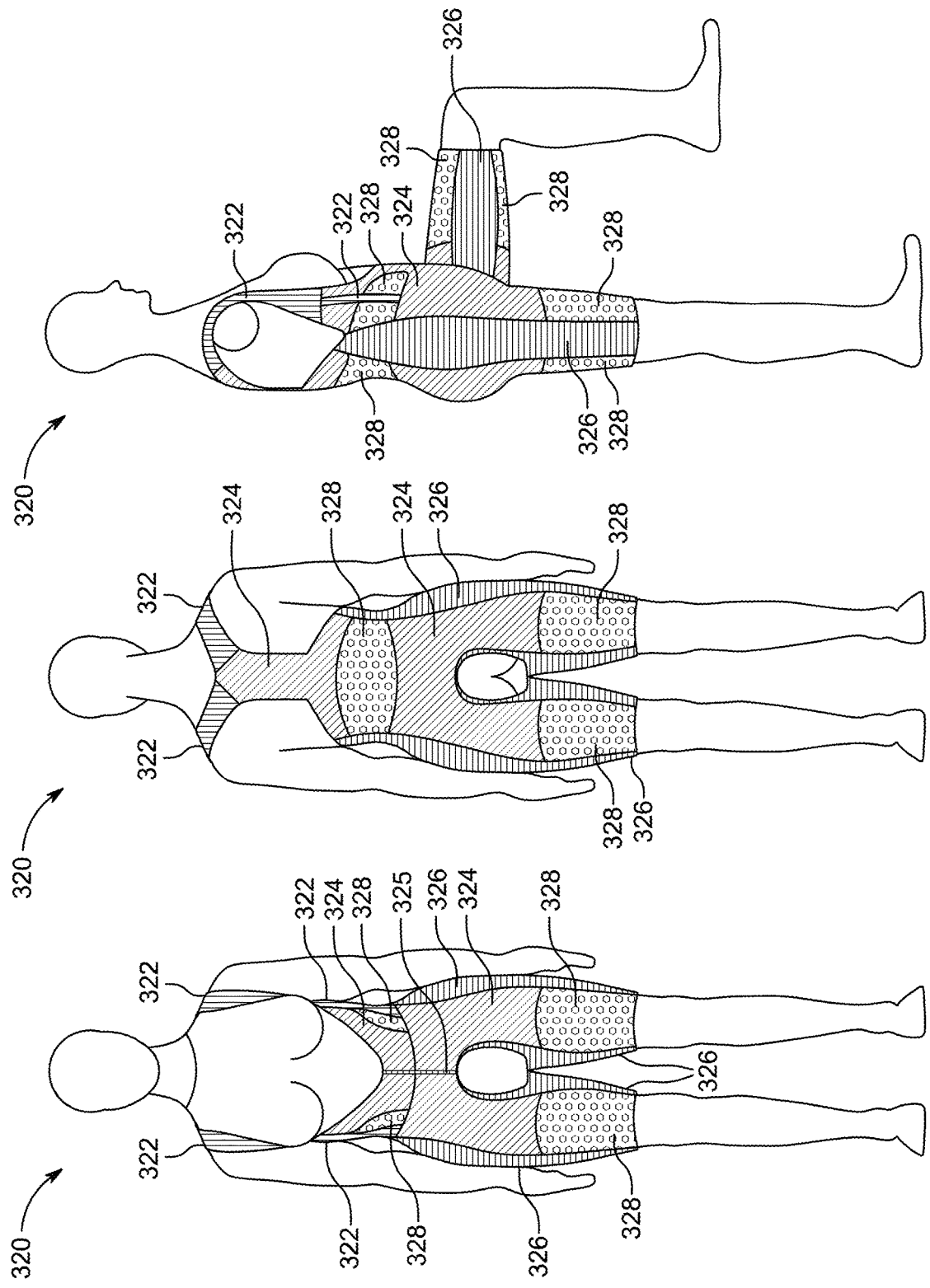

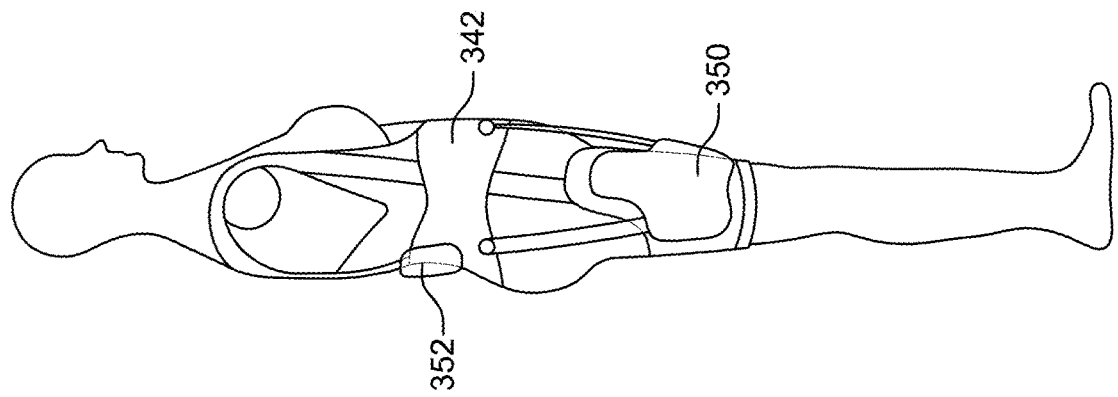
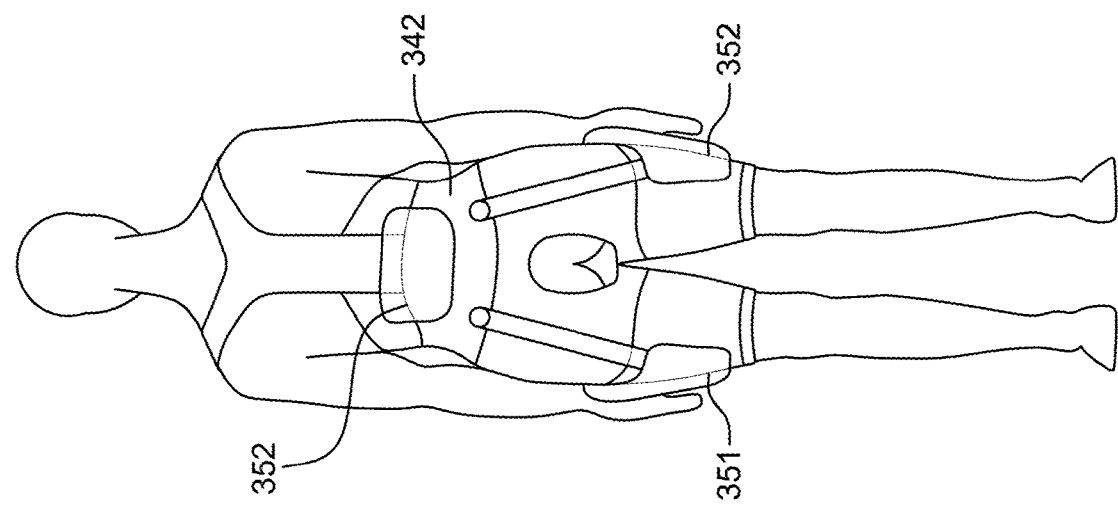
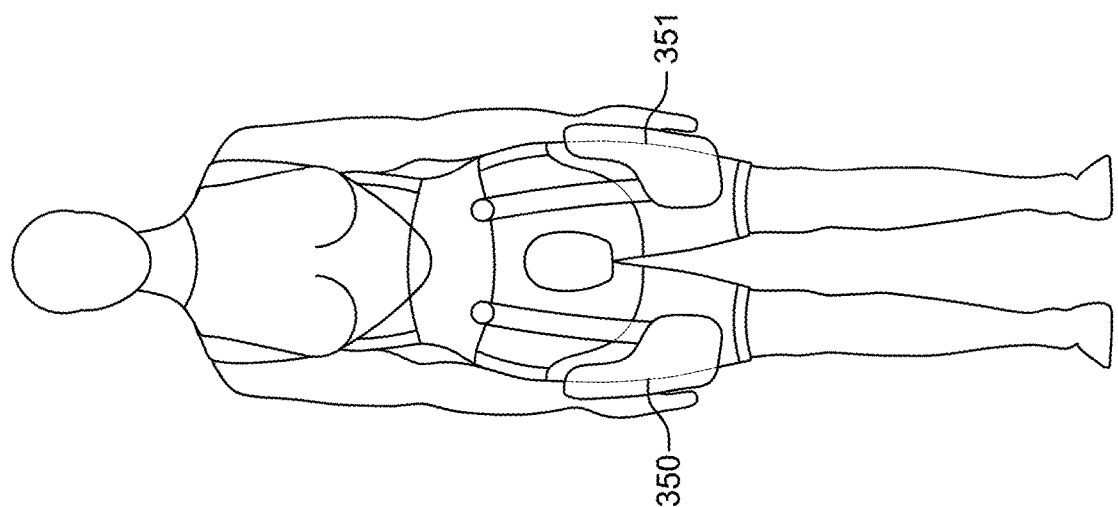

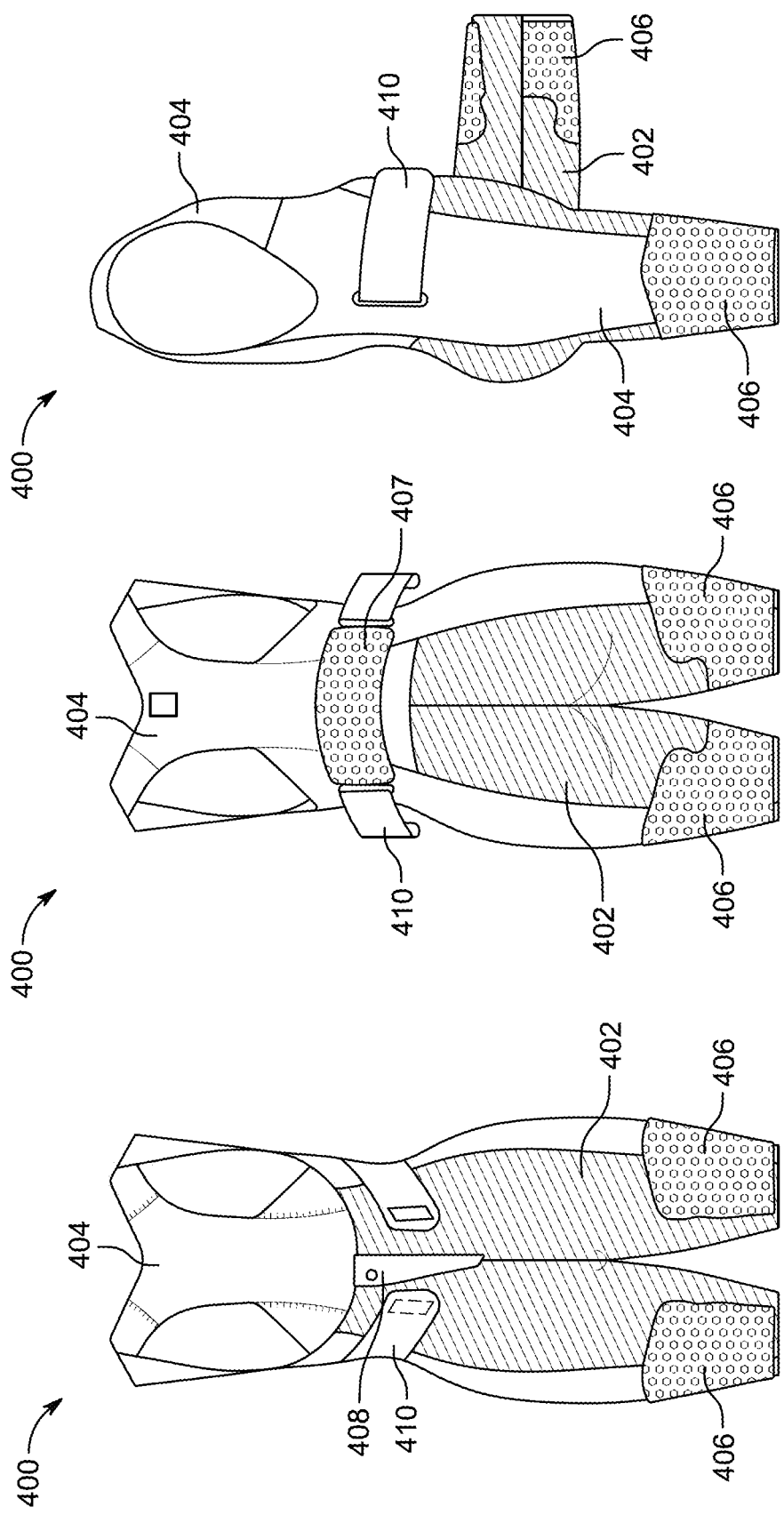

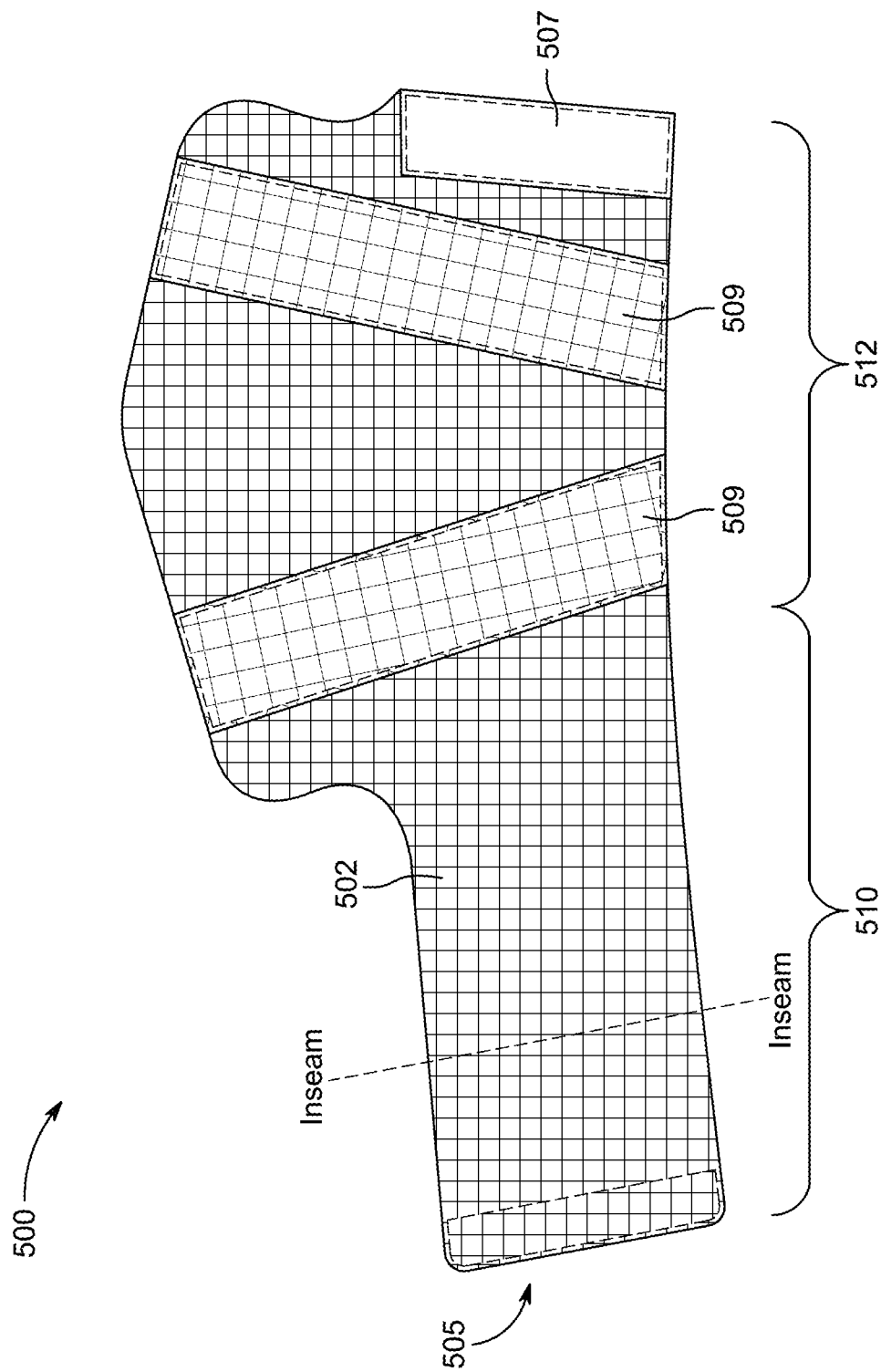

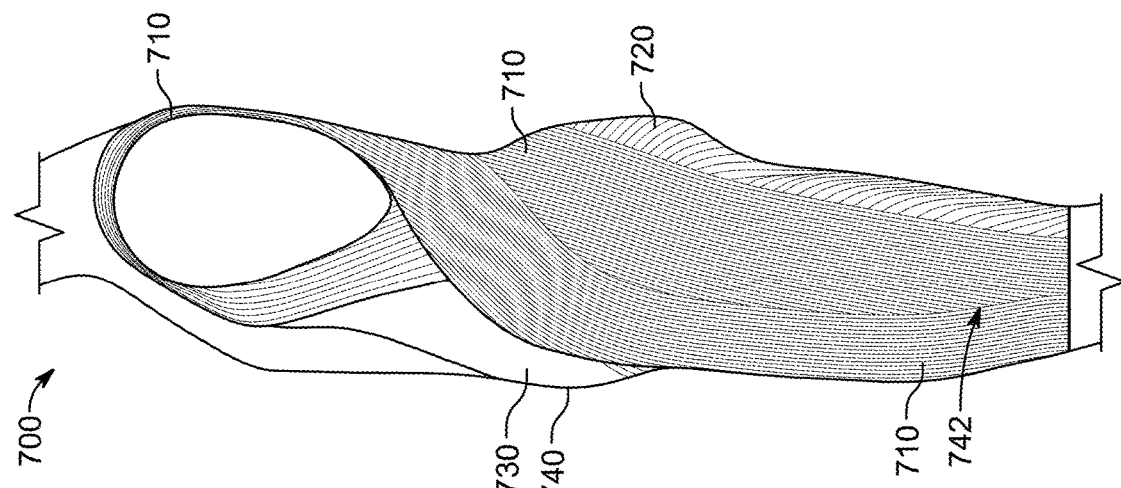
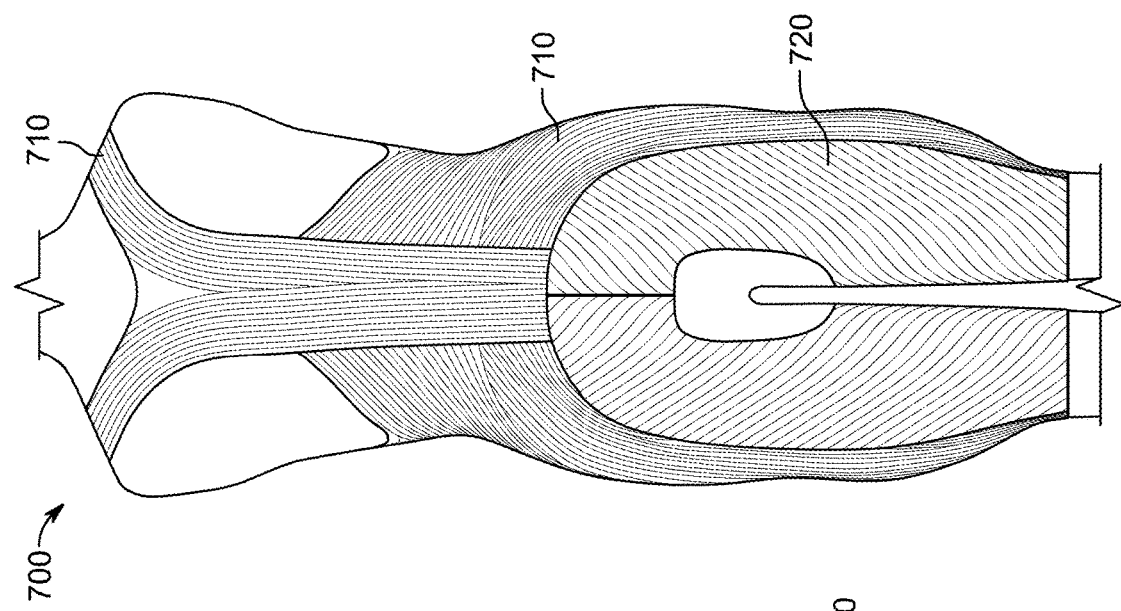
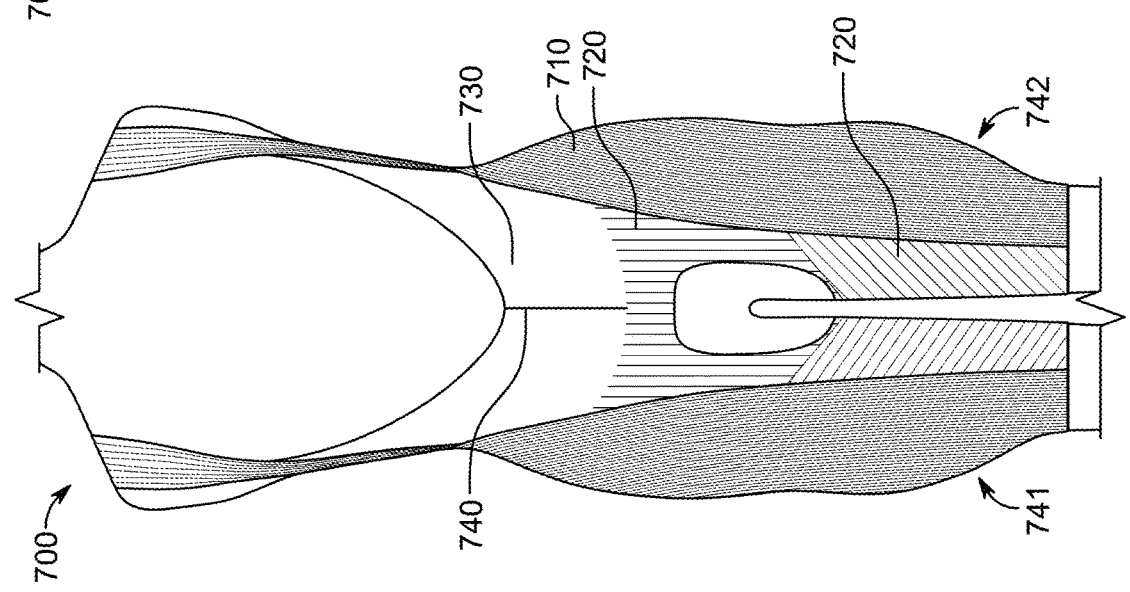

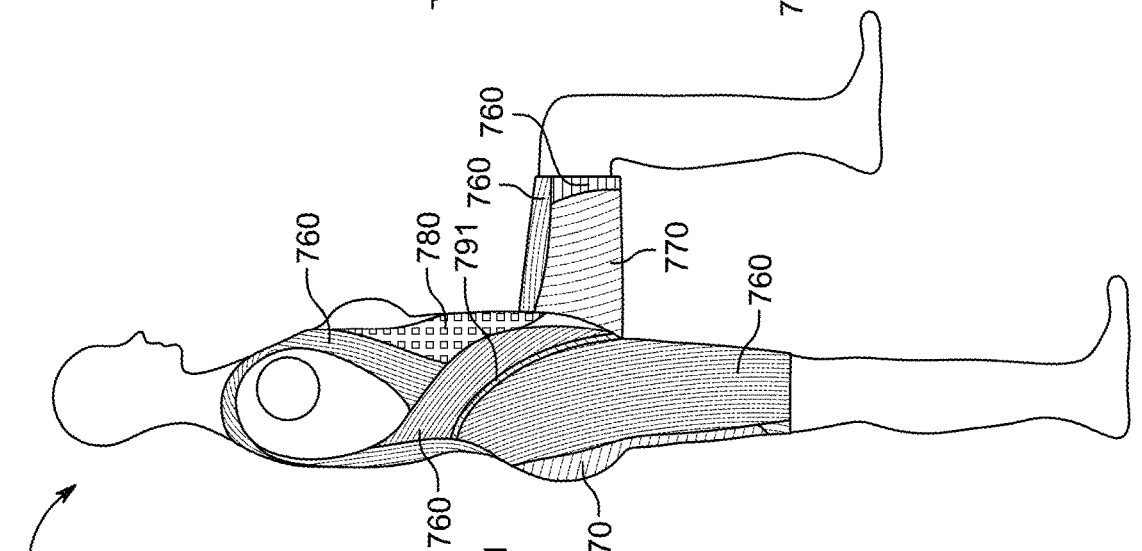

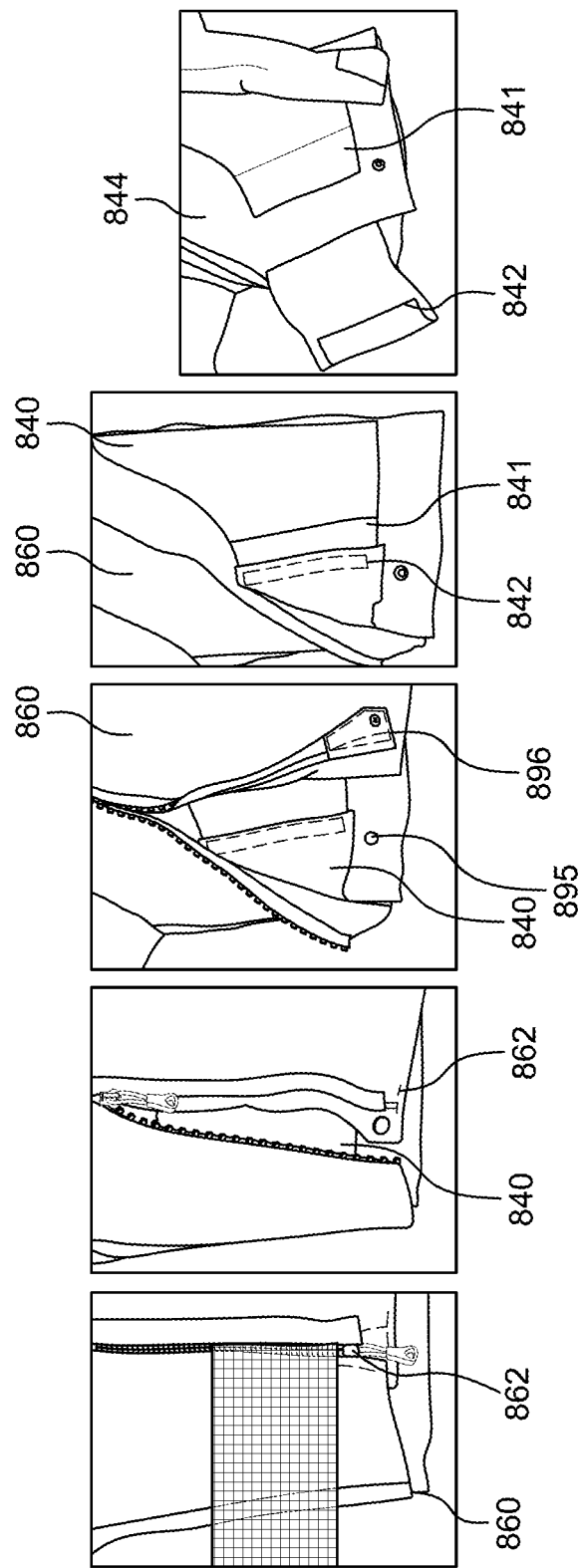

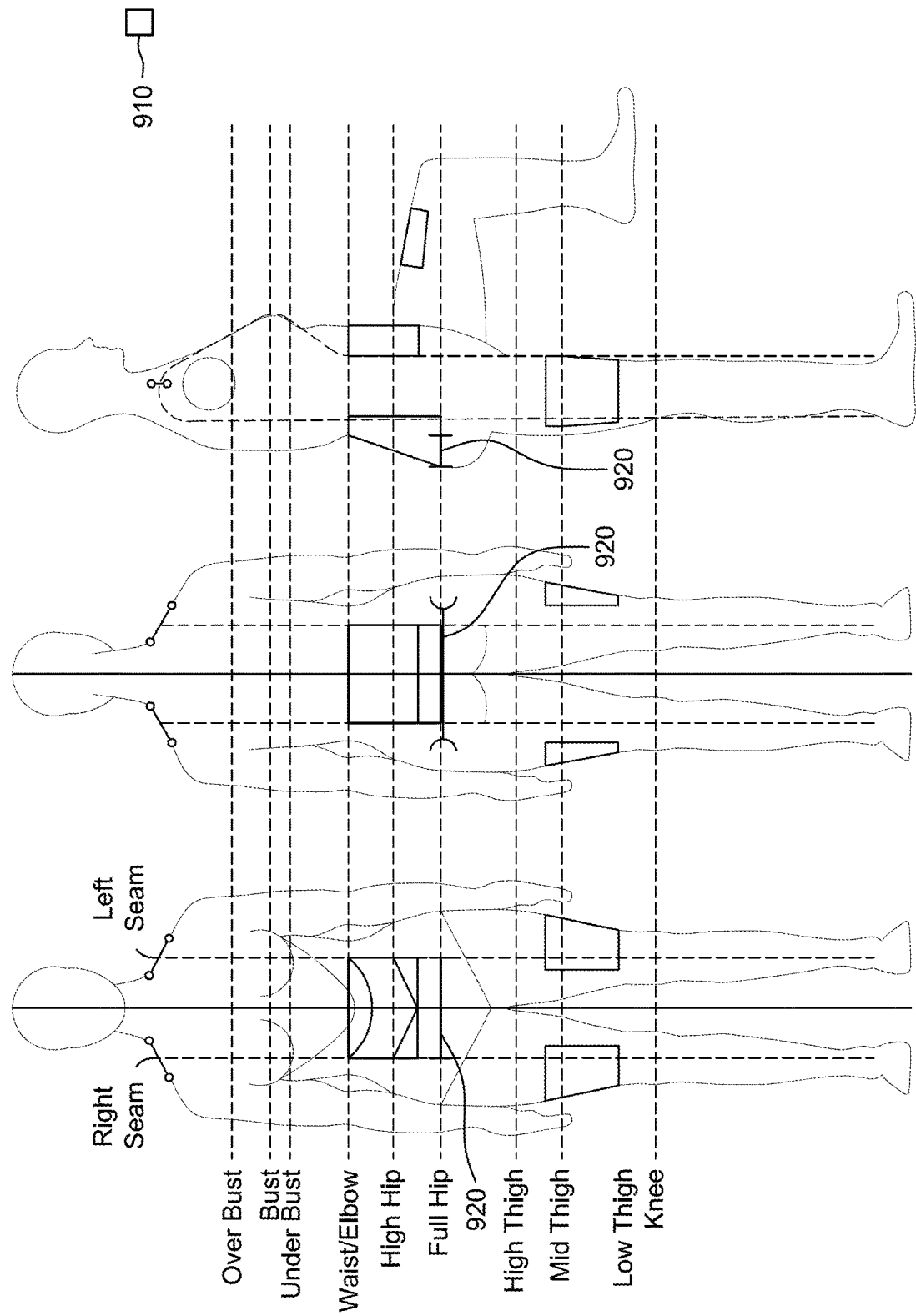

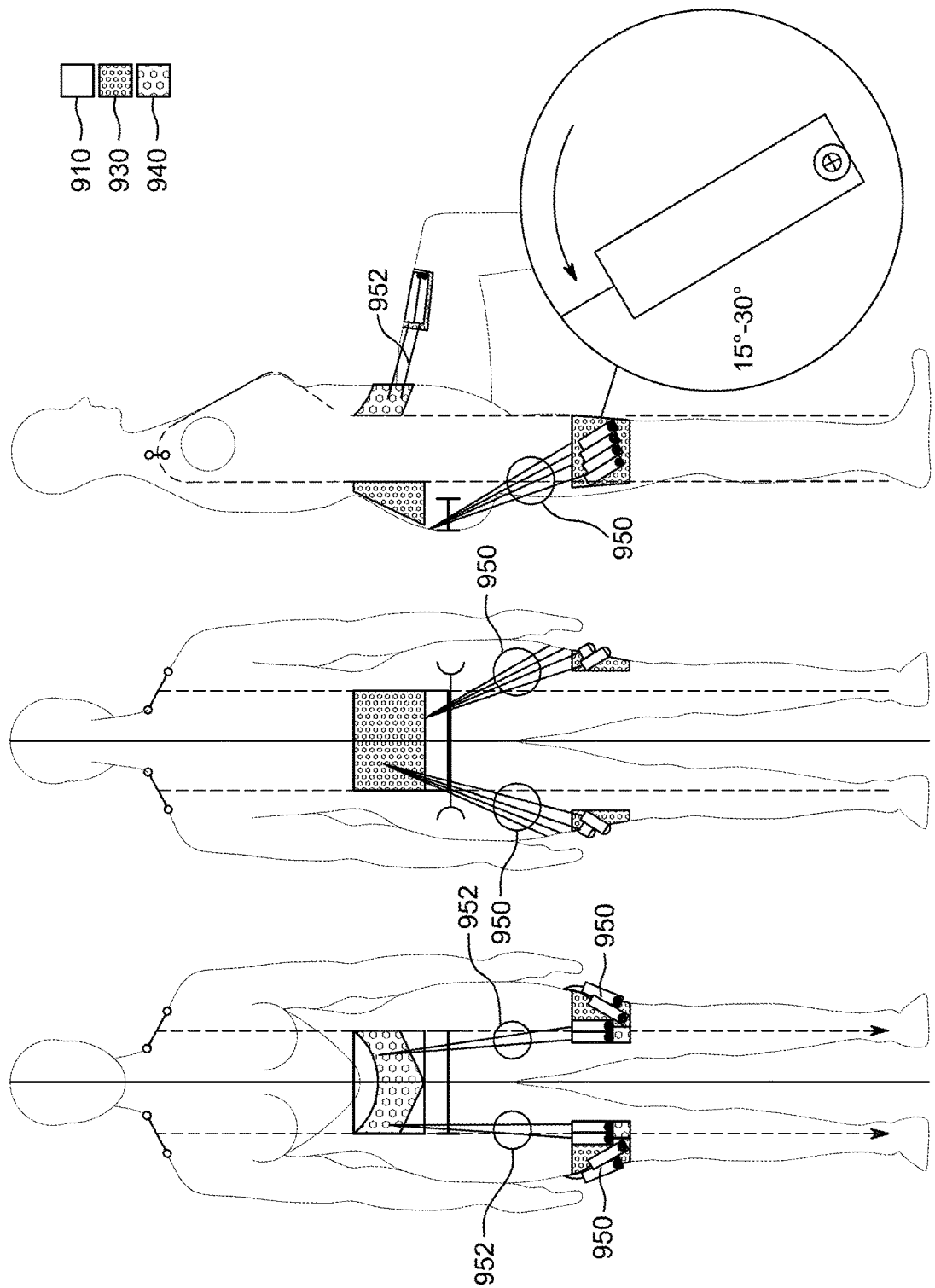

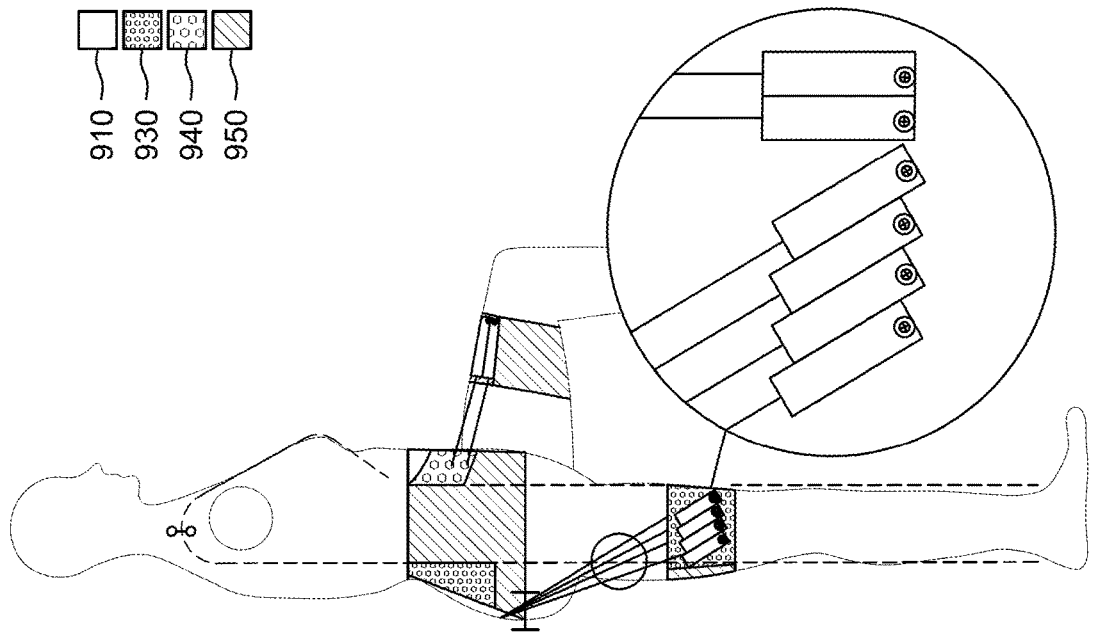
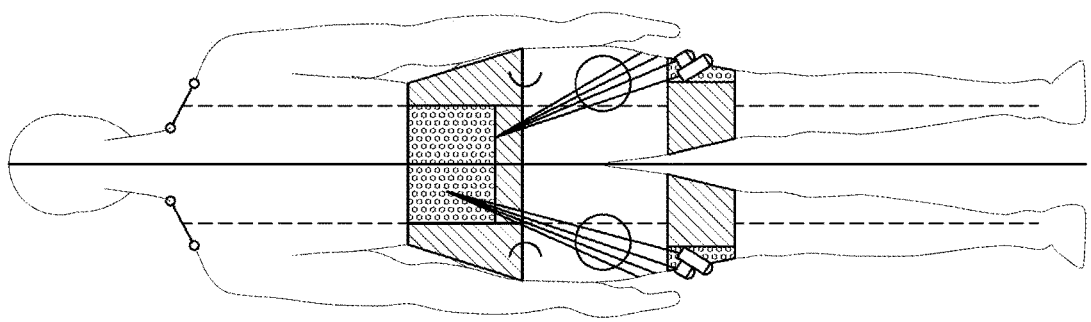
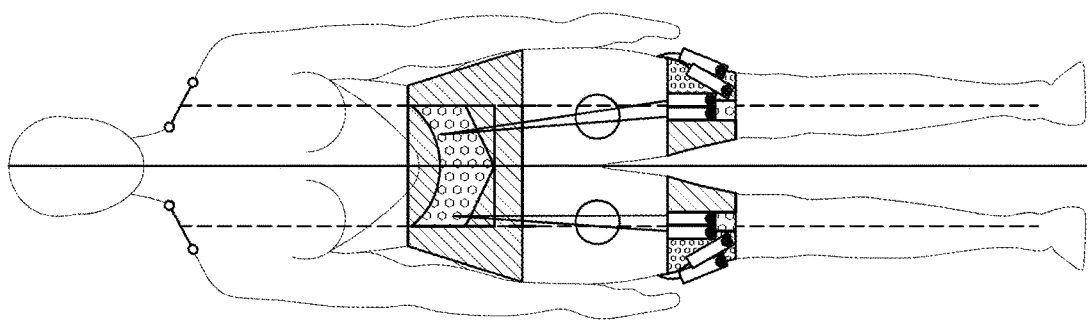
FIG. 9L
FIG. 9K
FIG. 9J

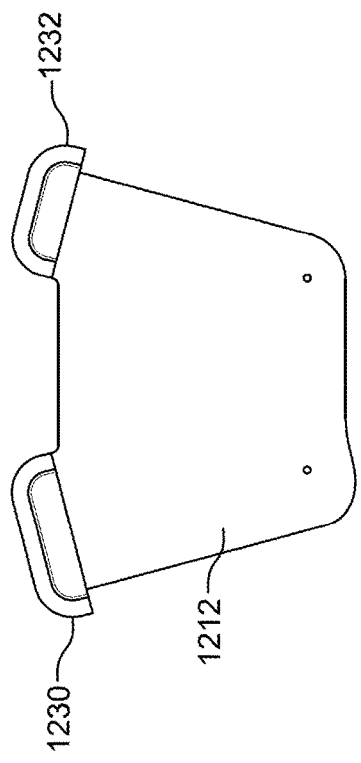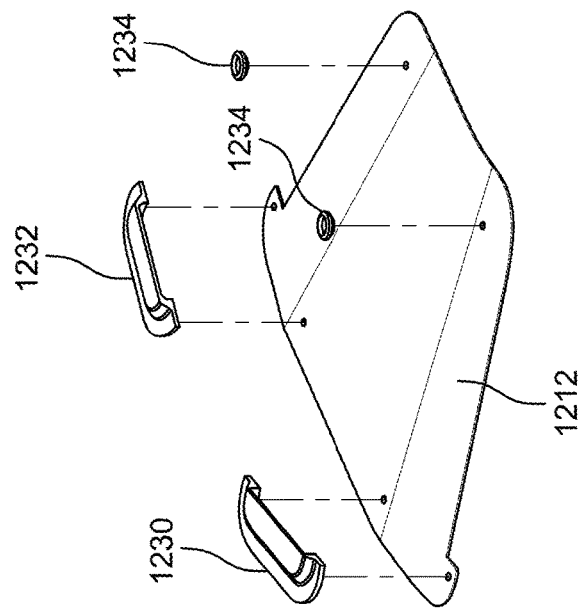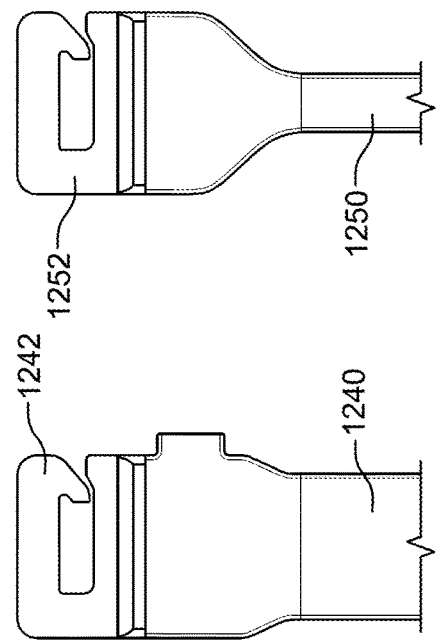

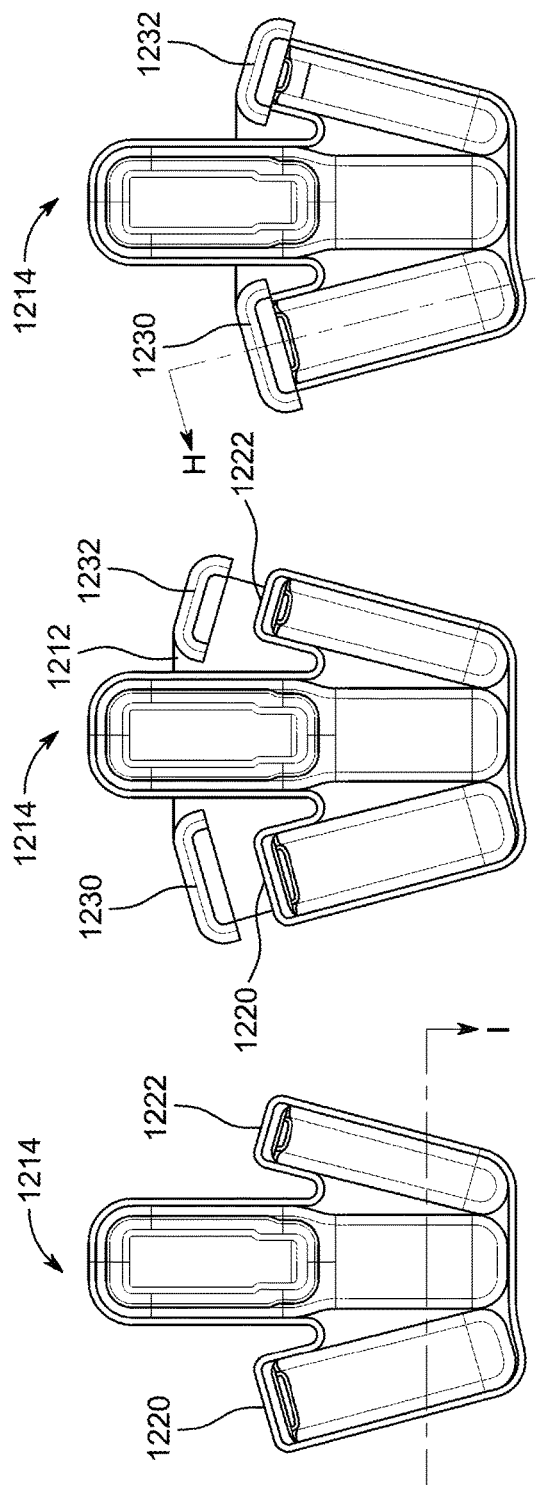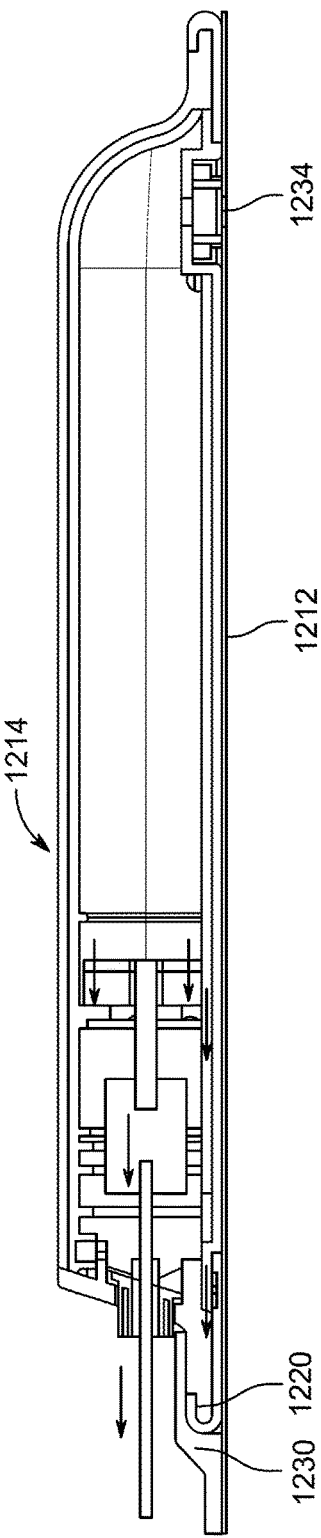

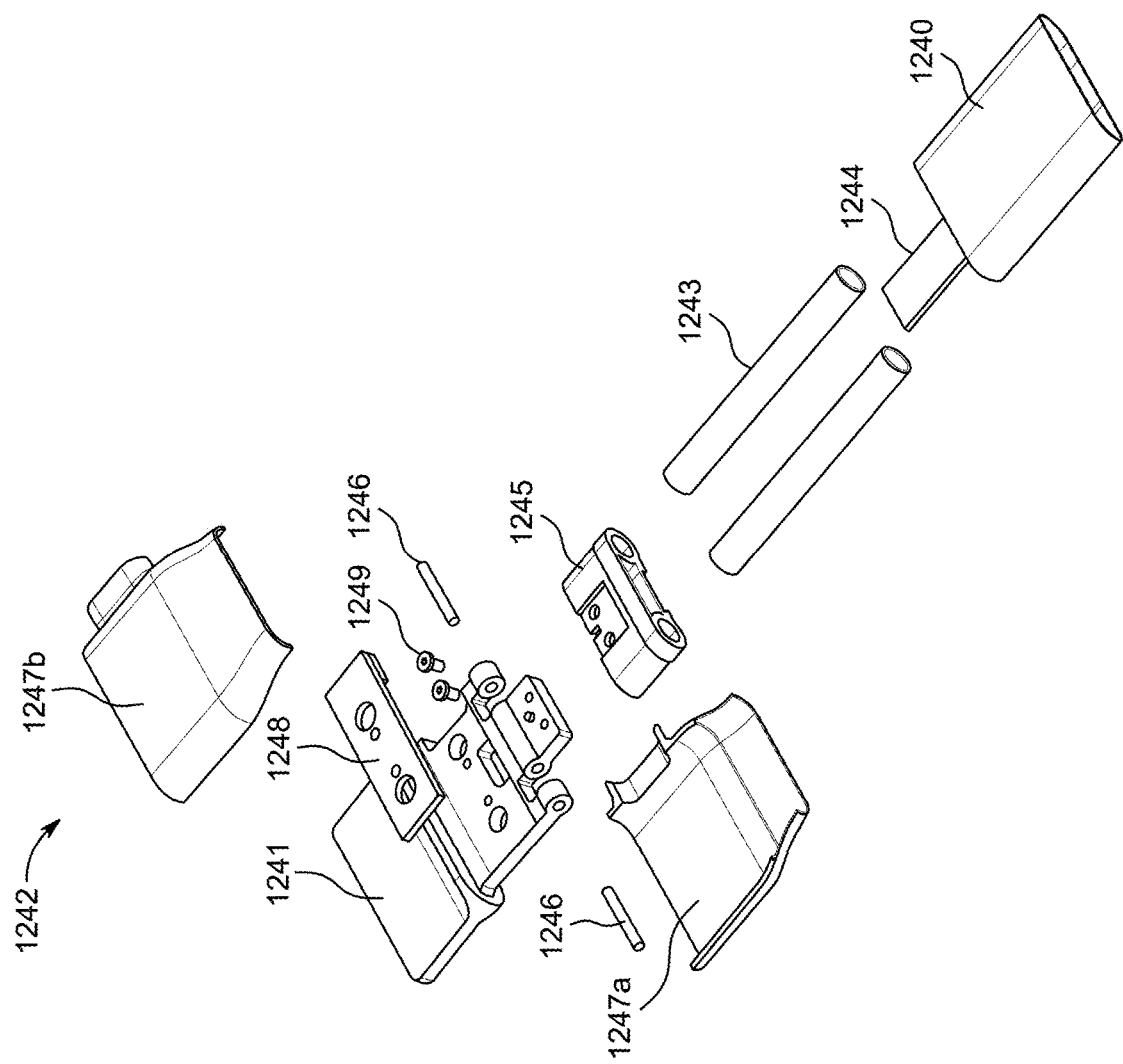

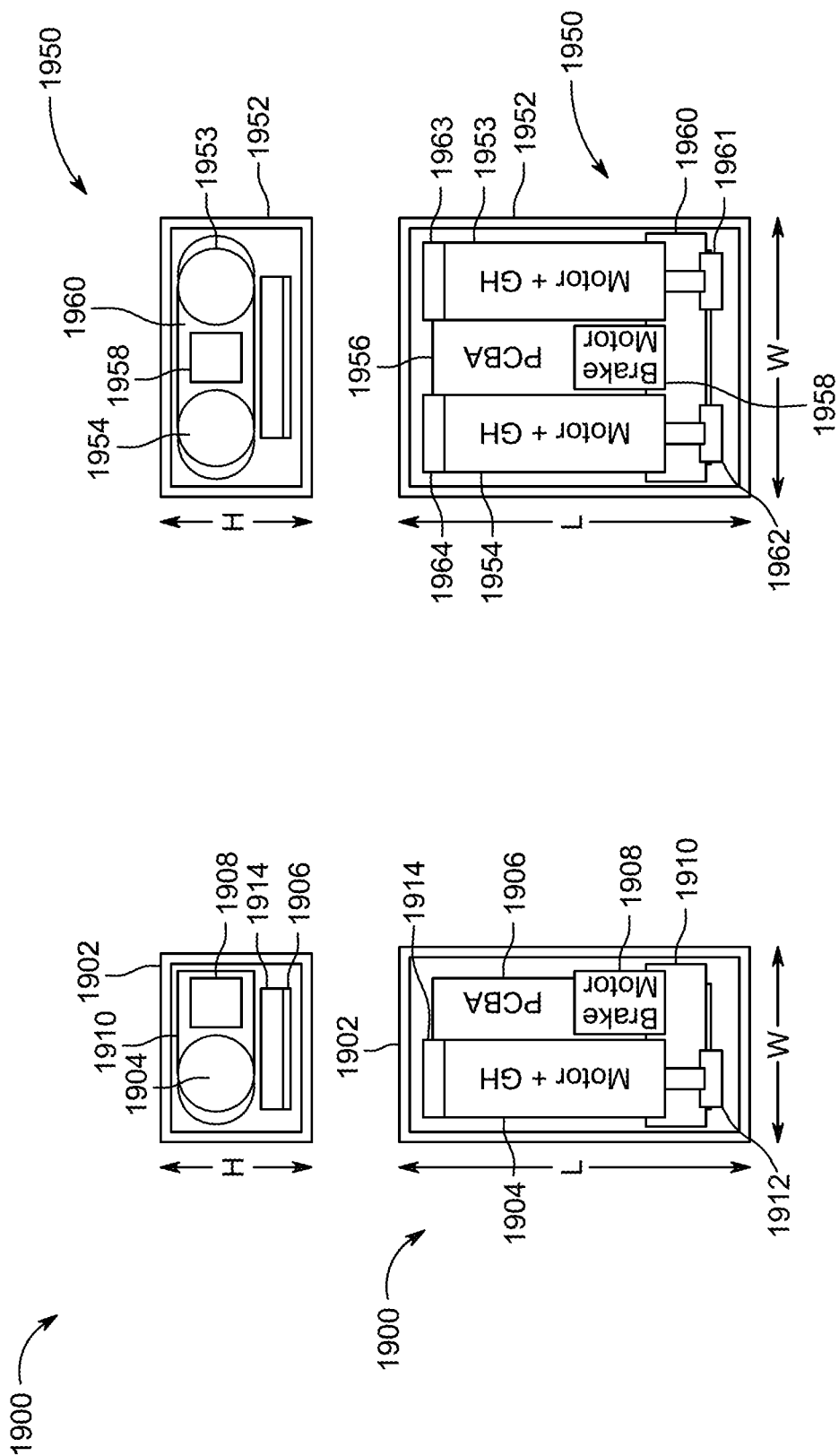

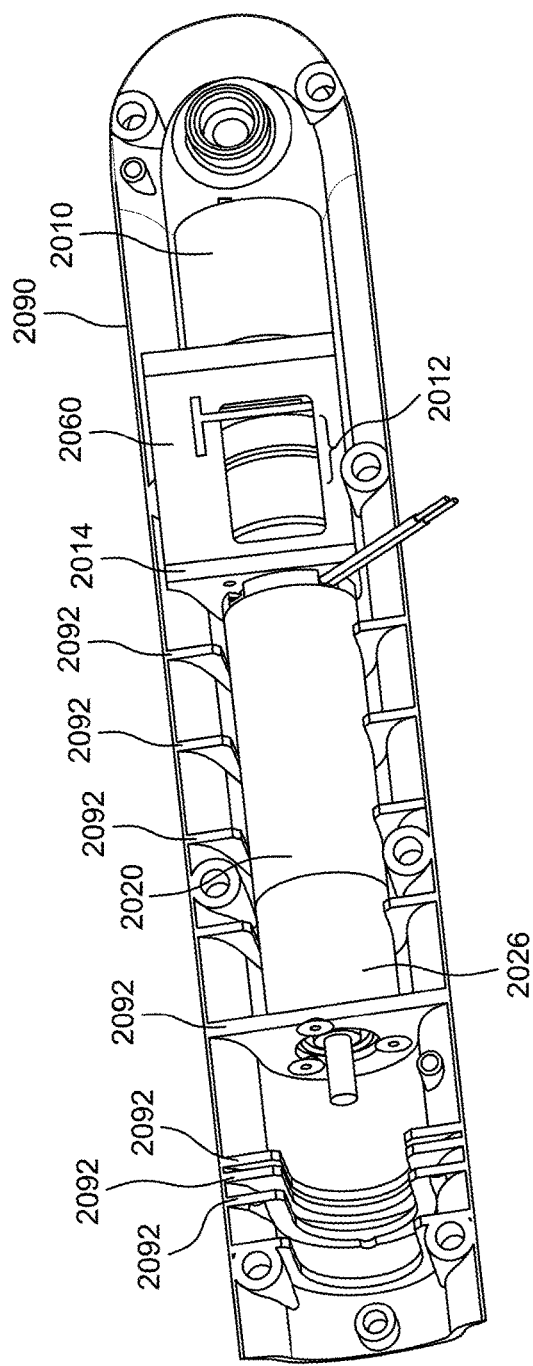
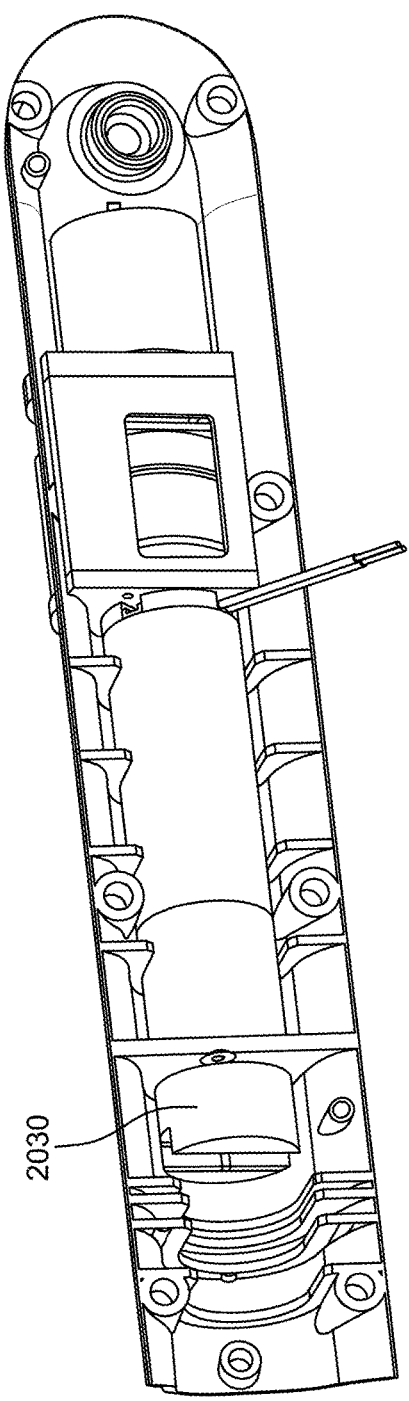
FIG. 20C
FIG. 20D

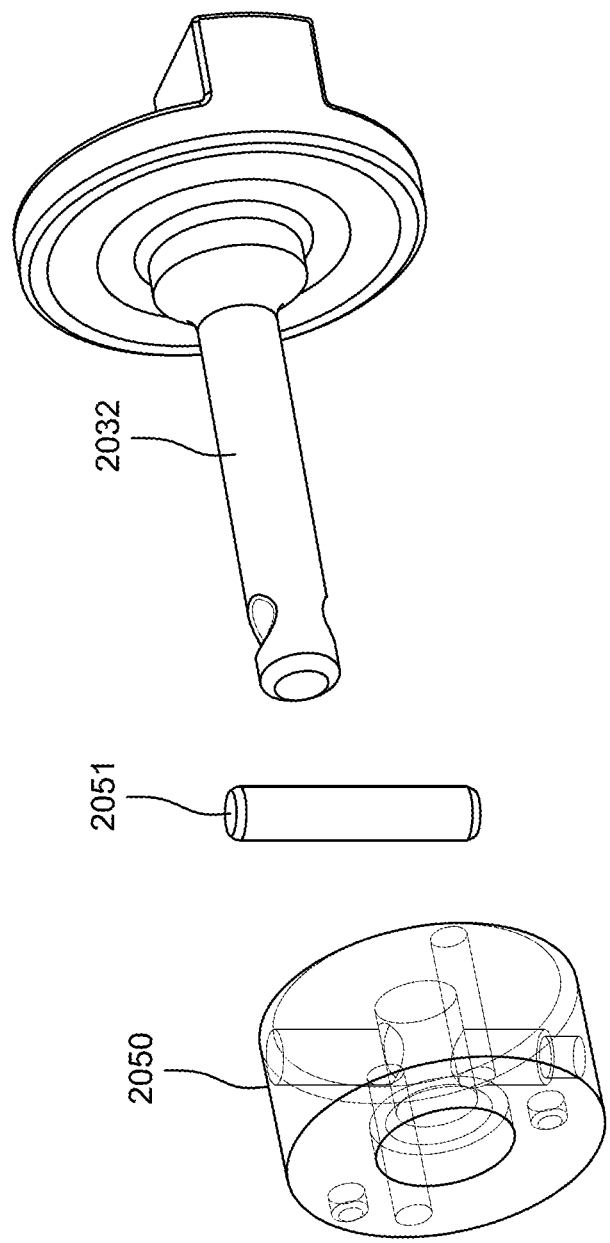

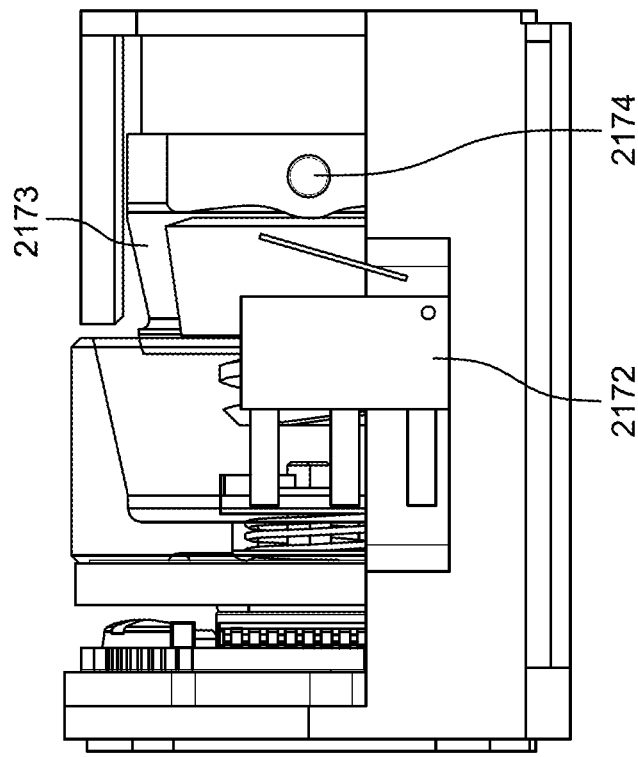
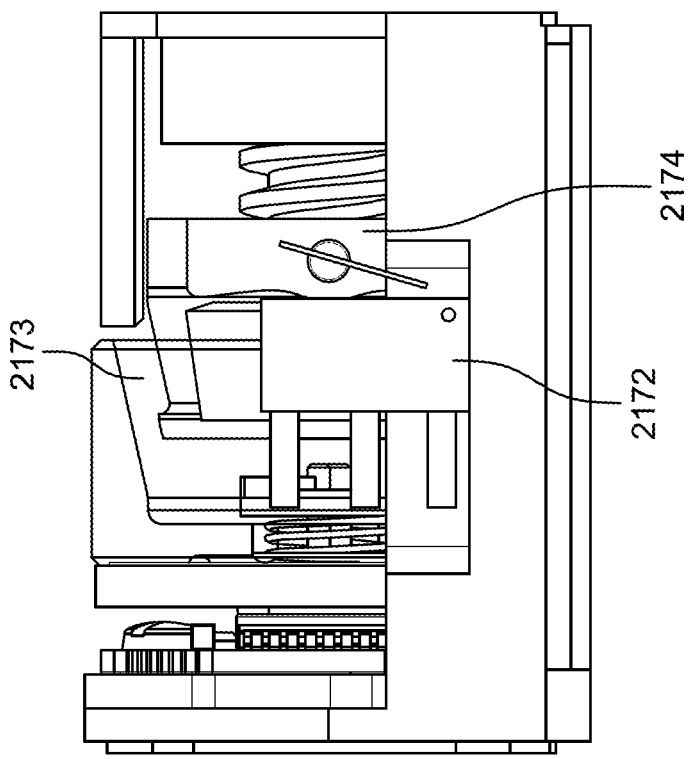
FIG. 21F

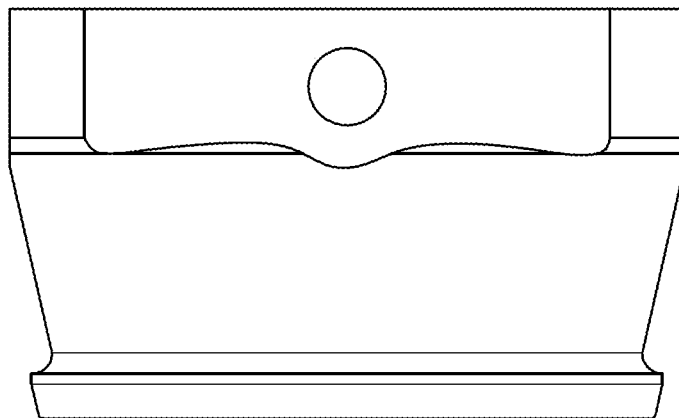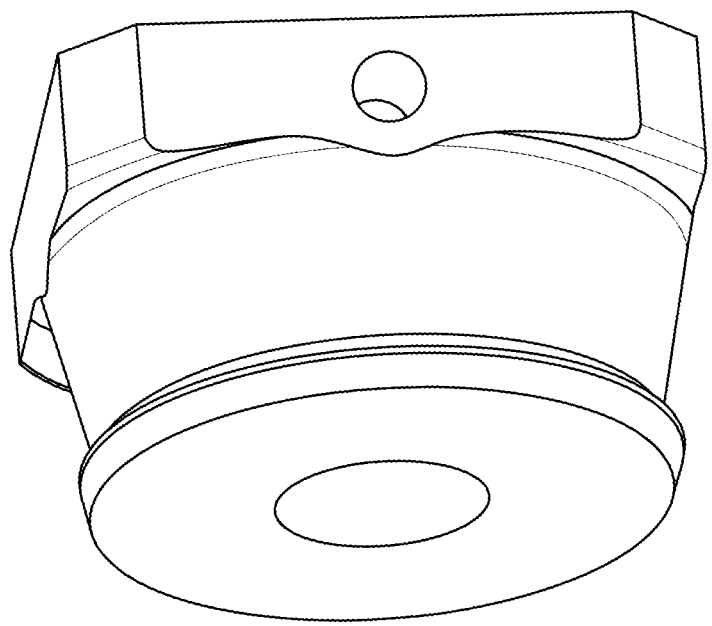
FIG. 21J

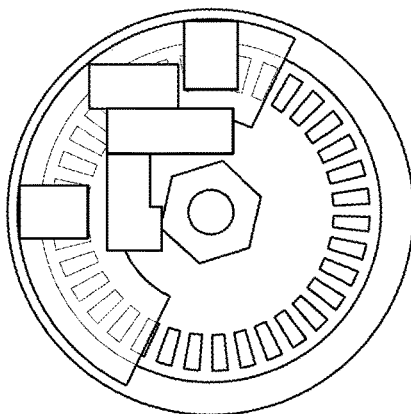
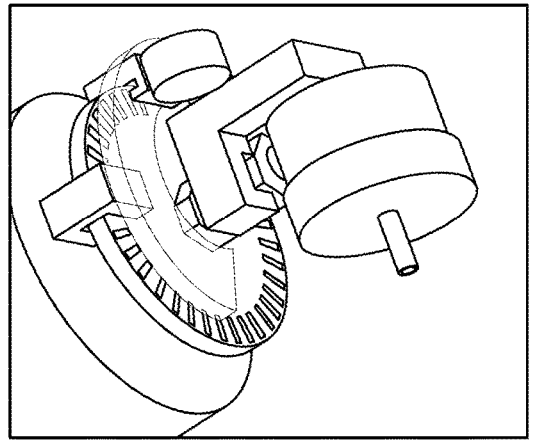
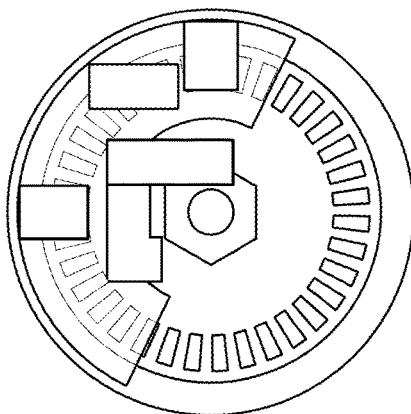
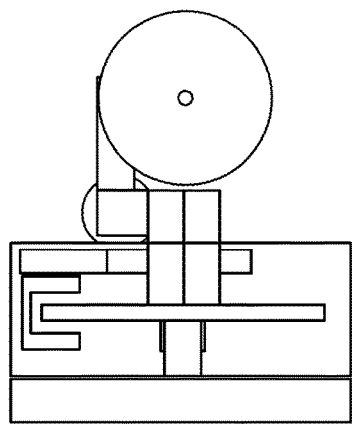
FIG. 26

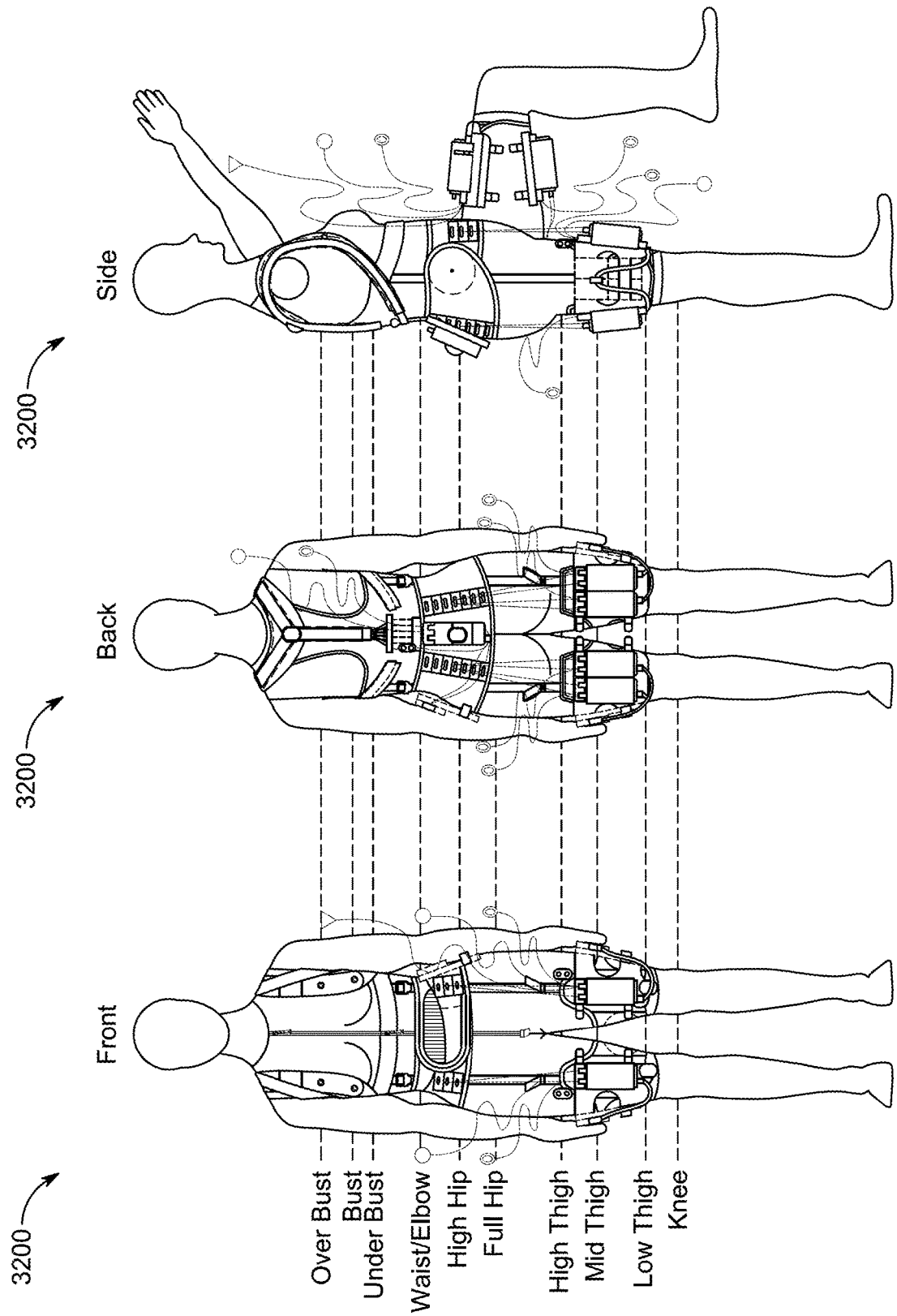

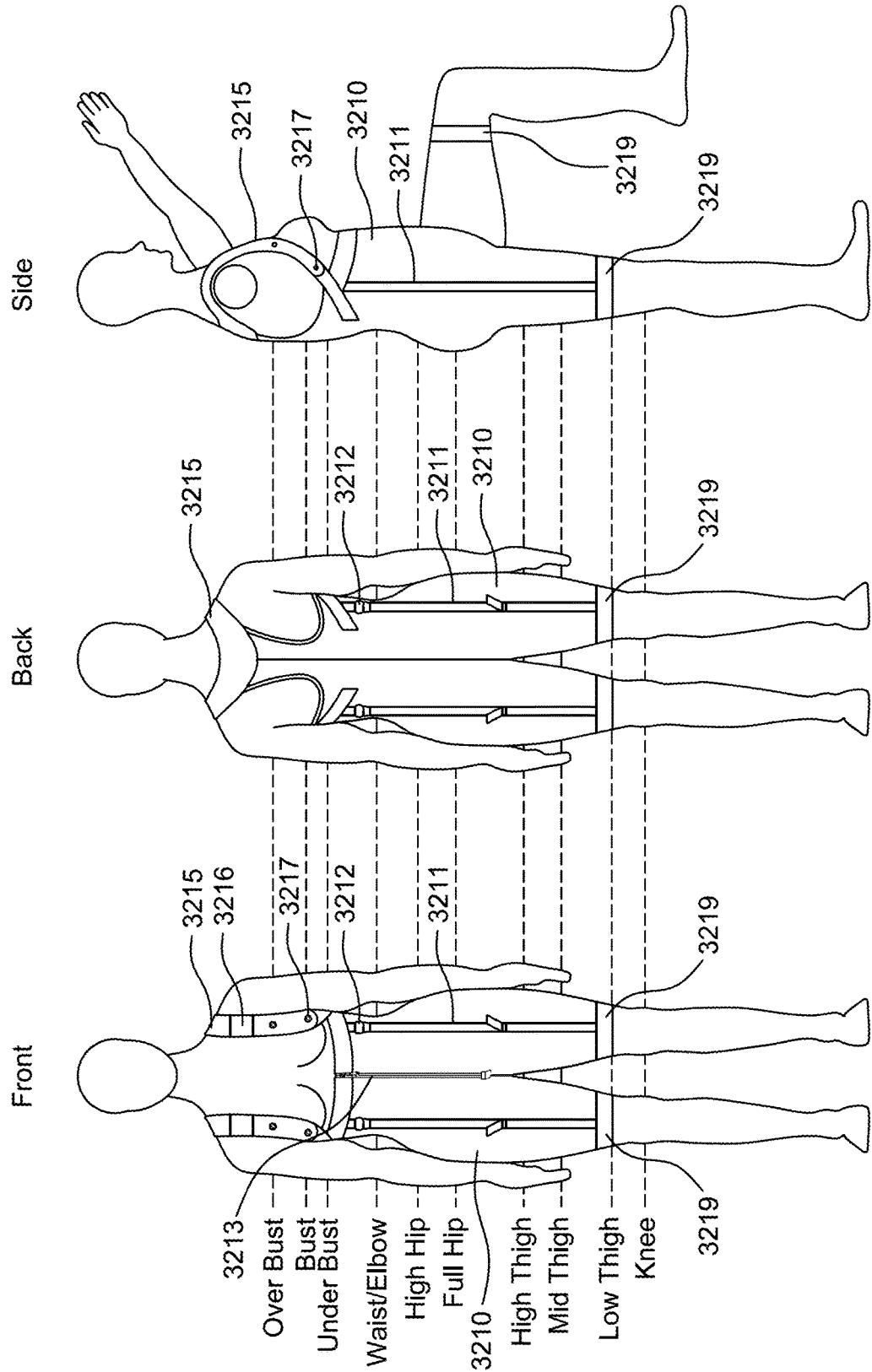

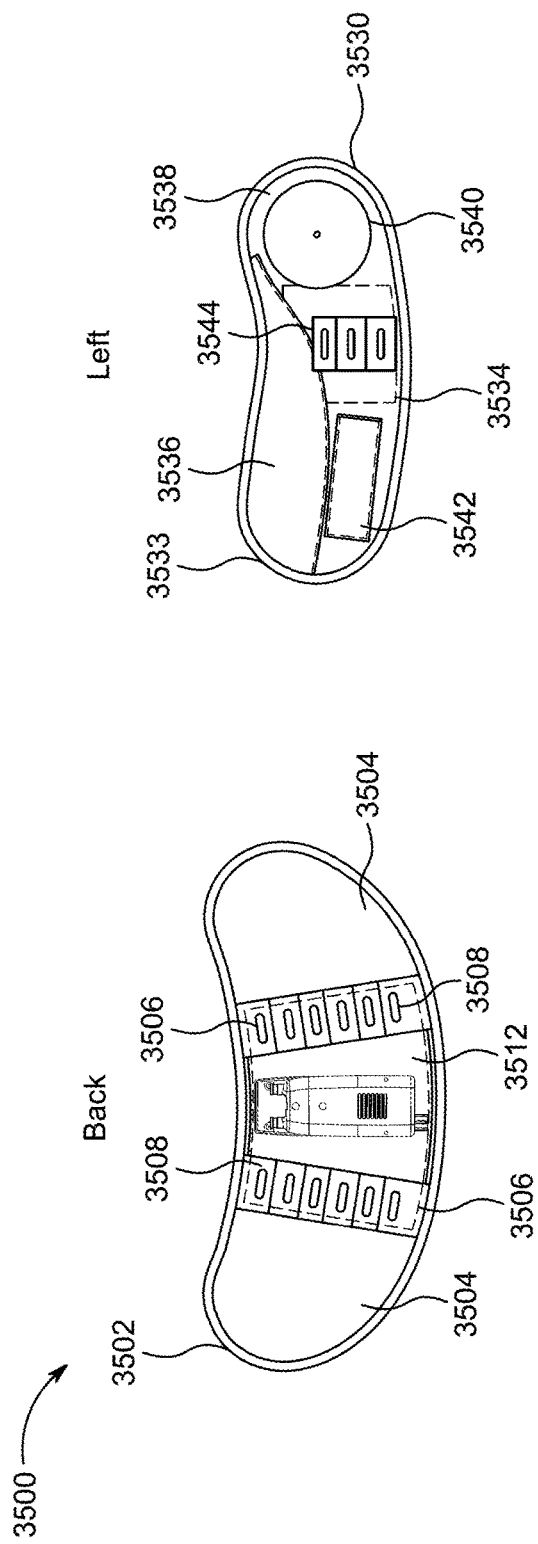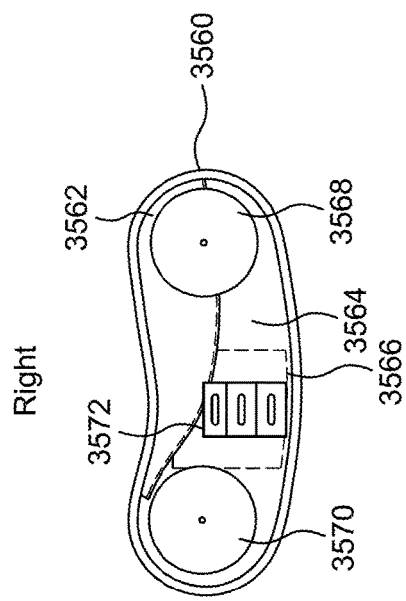
FIG. 35A
FIG. 35B
FIG. 35C

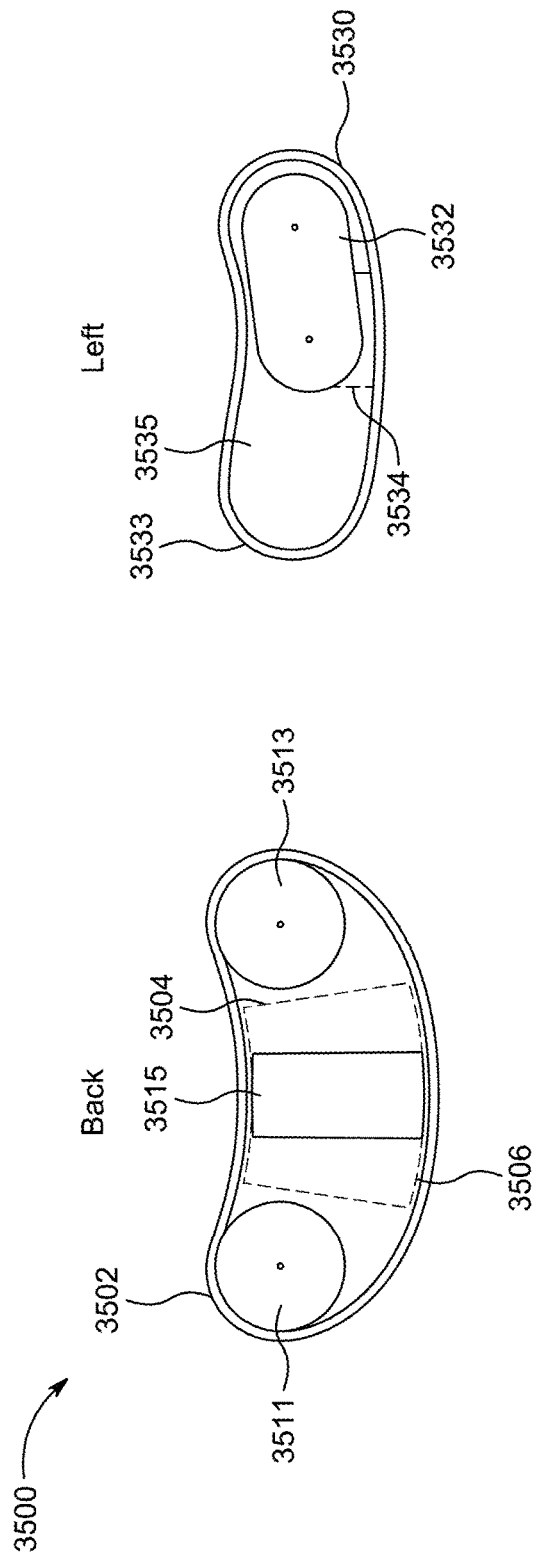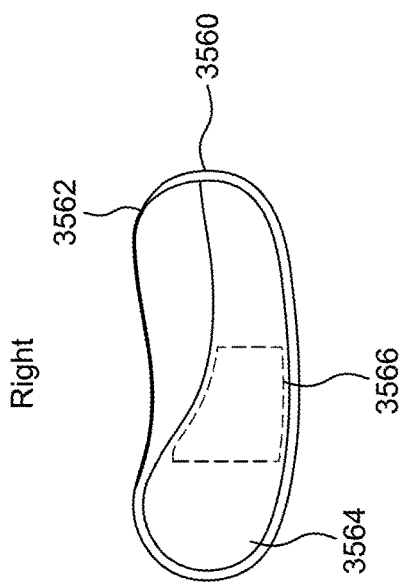
FIG. 35D
FIG. 35E
FIG. 35F

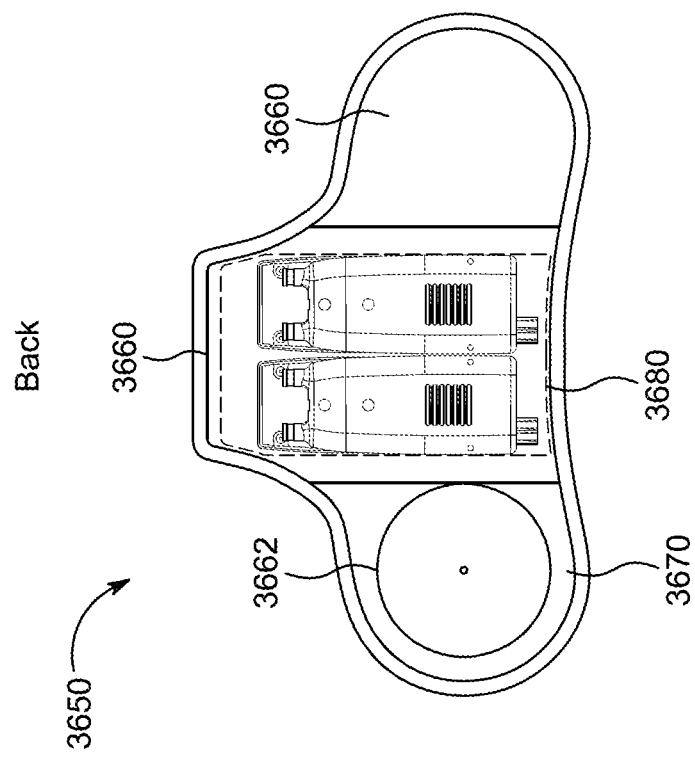
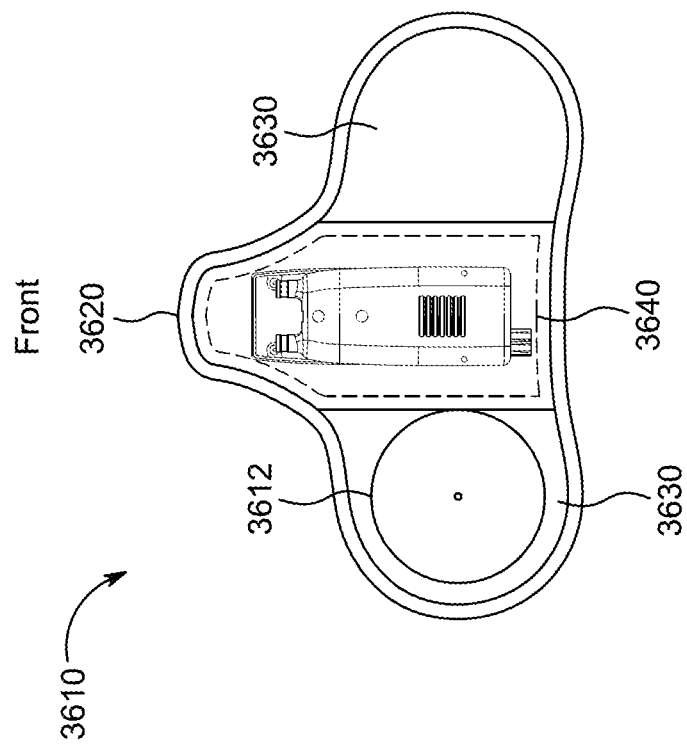

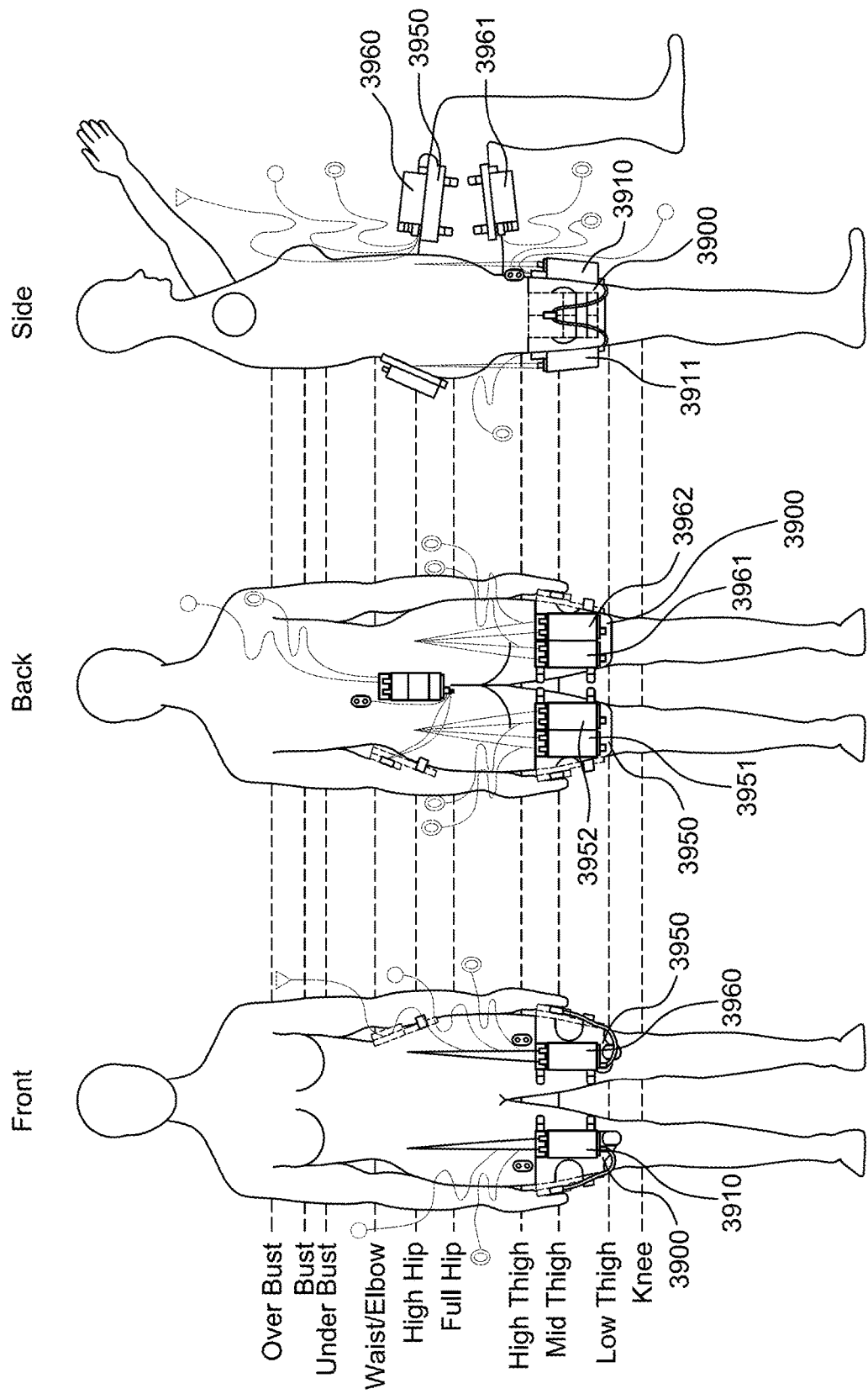

EXOSUIT LOAD BEARING DISTRIBUTION SYSTEMS

CROSS-REFERENCE TO RELATED APPLICATIONS

This application claims priority to U.S. Provisional Patent Application No. 62/591,739, filed Nov. 28, 2017, U.S. Provisional Patent Application No. 62/644,301, filed Mar. 16, 2018 and U.S. Provisional Patent Application No. 62/724,452, filed Aug. 29, 2018, the disclosures of which are incorporated by reference in their entireties.

BACKGROUND

Wearable robotic systems have been developed for augmentation of humans' natural capabilities, or to replace functionality lost due to injury or illness.

SUMMARY

Exosuit systems may be assistive, as it physically assists the wearer in performing particular activities, or can provide other functionality such as communication to the wearer through physical expressions to the body, engagement of the environment, or capturing of information from the wearer. In order to transmit assistance to the user of the exosuit, loads need to be translated by the exosuit. This is can be through the use of load distribution members. Load distribution members can be placed around the pelvis, waist, thighs, and other body parts.

In one embodiment, a pelvis load distribution system is provided that includes a first member comprising first and second interfacing regions, a first rigid member, and a first plurality of anchor stays mounted above the first rigid member; a second member comprising third and fourth interfacing regions, a second rigid member, and a second plurality of anchor stays mounted above the second rigid member; and a third member comprising fifth and sixth interfacing regions, a third rigid member, and a third plurality of anchor stays mounted above the third rigid member; wherein the first, second, and third members interconnect to form a three part loop having an adjustable fit that enables the three part loop to be secured around a pelvis of a human being.

In another embodiment, a thigh load distribution system is provided that includes a first member comprising first and second interfacing regions and a first stay region, wherein the first interface region is located on an exterior side of the first member and wherein the second interfacing region is located on an interior side of the first member; and a second member comprising third and fourth interfacing regions and a second stay region, wherein the third interface region is located on an exterior side of the second member and wherein the fourth interfacing region is located on an interior side of the first member; wherein the first and second members interconnect to form a two part loop having an adjustable fit that enables the two part loop to be secured around a thigh of a human being.

In yet another embodiment, a thigh load distribution system is provided that includes flange member; stay region secured to the flange member; first no stretch member secured on top of the stay region and the flange member; first and second interfacing regions secured on top of the first no stretch member; third interfacing region secured below the flange member; and adjustment member secured to the first no stretch member. The adjustment member includes a stretch member secured to the first no stretch member; a second no stretch member secured to the stretch member; and a fourth interfacing member secured to the second no stretch member; wherein the first and second interfacing members are coupled together to establish a first loop connection around a thigh of a human, and wherein the fourth and third interfacing members are coupled together to establish a second loop connection around the thigh

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIGS. 1A-1C show front, back, and side views of a base layer of an exosuit according to an embodiment;

FIGS. 1D-1F show front, back, and side views, respectively, of a power layer according to an embodiment;

FIGS. 1D-1F show front, back, and side views, respectively, of a power layer according to an embodiment;

FIGS. 3D-3F show illustrative front, back, and side views of next-to-skin (N2S) layer according to an embodiment;

FIGS. 3J-3L show illustrative front, back, and side views of power layer segments according to an embodiment;

FIGS. 4A-4C show illustrative front, back, and side views of a next-to-skin (N2S) layer according to an embodiment;

FIGS. 5A-5C show different views a thigh load distribution member according to an embodiment;

FIGS. 7A-7C show illustrative front, back, and side views of a cover layer according to an embodiment;

FIGS. 7D-7F show illustrative front, back, and side views of cover layer according to an embodiment;

FIG. 7G shows a close up of circle portion G of cover layer according to an embodiment;

FIGS. 8A-8E show a leg portion of an exosuit in various states according to an embodiment;

FIGS. 9A-9L show illustrative front, back, and side views of a human, with emphasis on different power layer segment anchoring locations, preferred anchoring locations, projected string transmission paths, and load distribution members, according to various embodiments;

FIGS. 12A-12L show different views of a leg patch assembly according to various embodiments;

FIGS. 19A-19B show different flexdrive modules according to various embodiments;

FIGS. 20B-20K shows different views of the module of FIG. 20A or portions thereof according to various embodiments;

FIGS. 21C-21J show views of an alternative flexdrive module according to an embodiment;

FIG. 26 shows a solenoid lock mechanism assembly according to an embodiment;

FIGS. 32A-32C show illustrative front, back, and side view of exosuit showing all layers but cover layer according to various embodiments;

FIG. 33A-33C show illustrative front, back, and side view of N2S layer according to various embodiments;

FIGS. 35A-35H show exterior and interior views of a back member, left member, and right member that collectively form pelvis LDM according to various embodiments;

FIGS. 36A-36F show different views of components of thigh load distribution members according to various embodiments;

FIGS. 39A-39C show illustrative front, back, and side of patch members according to various embodiments.

DETAILED DESCRIPTION

Figure 1J:
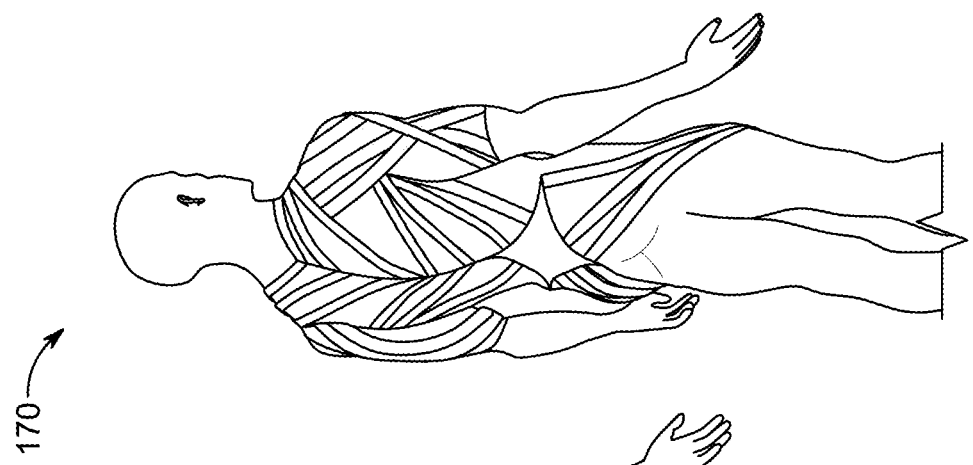
FIGS. 1I and 1J show front and side views of an illustrative exosuit having several power layer segments that approximate many of the muscles shown in FIGS. 1G and 1H, according to various embodiments.

In the following description, numerous specific details are set forth regarding the systems, methods and media of the disclosed subject matter and the environment in which such systems, methods and media may operate, etc., in order to provide a thorough understanding of the disclosed subject matter. It can be apparent to one skilled in the art, however, that the disclosed subject matter may be practiced without such specific details, and that certain features, which are well known in the art, are not described in detail in order to avoid complication of the disclosed subject matter. In addition, it can be understood that the examples provided below are exemplary, and that it is contemplated that there are other systems, methods and media that are within the scope of the disclosed subject matter.

In the descriptions that follow, an exosuit or assistive exosuit is a suit that is worn by a wearer on the outside of his or her body. It may be worn under the wearer's normal clothing, over their clothing, between layers of clothing, or may be the wearer's primary clothing itself. The exosuit may be supportive and/or assistive, as it physically supports or assists the wearer in performing particular activities, or can provide other functionality such as communication to the wearer through physical expressions to the body, engagement of the environment, or capturing of information from the wearer. In some embodiments, a powered exosuit system can include several subsystems, or layers. In some embodiments, the powered exosuit system can include more or less subsystems or layers. The subsystems or layers can include the base layer, stability layer, power layer, sensor and controls layer, a covering layer, and user interface/user experience (UI/UX) layer.

The base layer provides the interfaces between the exosuit system and the wearer's body. The base layer may be adapted to be worn directly against the wearer's skin, between undergarments and outer layers of clothing, over outer layers of clothing or a combination thereof, or the base layer may be designed to be worn as primary clothing itself. In some embodiments, the base layer can be adapted to be both comfortable and unobtrusive, as well as to comfortably and efficiently transmit loads from the stability layer and power layer to the wearer's body in order to provide the desired assistance. The base layer can typically comprise several different material types to achieve these purposes. Elastic materials may provide compliance to conform to the wearer's body and allow for ranges of movement. The innermost layer is typically adapted to grip the wearer's skin, undergarments or clothing so that the base layer does not slip as loads are applied. Substantially inextensible materials may be used to transfer loads from the stability layer and power layer to the wearer's body. These materials may be substantially inextensible in one axis, yet flexible or extensible in other axes such that the load transmission is along preferred paths. The load transmission paths may be optimized to distribute the loads across regions of the wearer's body to minimize the forces felt by the wearer, while providing efficient load transfer with minimal loss and not causing the base layer to slip. Collectively, this load transmission configuration within the base layer may be referred to as a load distribution member. Load distribution members refer to flexible elements that distribute loads across a region of the wearer's body. Examples of load distribution members can be found in International Application PCT/US16/19565, titled "Flexgrip," the contents of which are incorporated herein by reference.

The load distribution members may incorporate one or more catenary curves to distribute loads across the wearer's body. Multiple load distribution members or catenary curves may be joined with pivot points, such that as loads are applied to the structure, the arrangement of the load distribution members pivots tightens or constricts on the body to increase the gripping strength. Compressive elements such as battens, rods, or stays may be used to transfer loads to different areas of the base layer for comfort or structural purposes. For example, a power layer component may terminate in the middle back due to its size and orientation requirements, however the load distribution members that anchor the power layer component may reside on the lower back. In this case, one or more compressive elements may transfer the load from the power layer component at the middle back to the load distribution member at the lower back.

The load distribution members may be constructed using multiple fabrication and textile application techniques. For example, the load distribution member can be constructed from a layered woven 45°/90° with bonded edge, spandex tooth, organza (poly) woven 45°/90° with bonded edge, organza (cotton/silk) woven 45°/90°, and Tyvek (non-woven). The load distribution member may be constructed using knit and lacing or horse hair and spandex tooth. The load distribution member may be constructed using channels and/or laces.

The base layer may include a flexible underlayer that is constructed to compress against a portion of the wearer's body, either directly to the skin, or to a clothing layer, and also provides a relatively high grip surface for one or more load distribution members to attach thereto. The load distribution members can be coupled to the underlayer to facilitate transmission of shears or other forces from the members, via the flexible underlayer, to skin of a body segment or to clothing worn over the body segment, to maintain the trajectories of the members relative to such a body segment, or to provide some other functionality. Such a flexible underlayer could have a flexibility and/or compliance that differs from that of the member (e.g., that is less than that of the members, at least in a direction along the members), such that the member can transmit forces along their length and evenly distribute shear forces and/or pressures, via the flexible underlayer, to skin of a body segment to which a flexible body harness is mounted.

Further, such a flexible underlayer can be configured to provide additional functionality. The material of the flexible underlayer could include anti-bacterial, anti-fungal, or other agents (e.g., silver nanoparticles) to prevent the growth of microorganisms. The flexible underlayer can be configured to manage the transport of heat and/or moisture (e.g., sweat) from a wearer to improve the comfort and efficiency of activity of the wearer. The flexible underlayer can include straps, seams, hook-and-loop fasteners, clasps, zippers, or other elements configured to maintain a specified relationship between elements of the load distribution members and aspects of a wearer's anatomy. The underlayer can additionally increase the ease with which a wearer can don and/or doff the flexible body harness and/or a system (e.g., a flexible exosuit system) or garment that includes the flexible body harness. The underlayer can additionally be configured to protect the wearer from ballistic weapons, sharp edges, shrapnel, or other environmental hazards (by including, e.g., panels or flexible elements of para-aramid or other high-strength materials).

The base layer can additionally include features such as size adjustments, openings and electro-mechanical integration features to improve ease of use and comfort for the wearer.

Size adjustment features permit the exosuit to be adjusted to the wearer's body. The size adjustments may allow the suit to be tightened or loosened about the length or circumference of the torso or limbs. The adjustments may comprise lacing, the Boa system, webbing, elastic, hook-and-loop or other fasteners. Size adjustment may be accomplished by the load distribution members themselves, as they constrict onto the wearer when loaded. In one example, the torso circumference may be tightened with corset-style lacing, the legs tightened with hook-and-loop in a double-back configuration, and the length and shoulder height adjusted with webbing and tension-lock fasteners such as cam-locks, D-rings or the like. The size adjustment features in the base layer may be actuated by the power layer to dynamically adjust the base layer to the wearer's body in different positions, in order to maintain consistent pressure and comfort for the wearer. For example, the base layer may be required to tighten on the thighs when standing, and loosen when sitting such that the base layer does not excessively constrict the thighs when seated. The dynamic size adjustment may be controlled by the sensor and controls layer, for example by detecting pressures or forces in the base layer and actuating the power layer to consistently attain the desired force or pressure. This feature does not necessarily cause the suit to provide physical assistance, but can create a more comfortable experience for the wearer, or allow the physical assistance elements of the suit to perform better or differently depending on the purpose of the movement assistance.

Opening features in the base layer may be provided to facilitate donning (putting the exosuit on) and doffing (taking the exosuit off) for the wearer. Opening features may comprise zippers, hook-and-loop, snaps, buttons or other textile fasteners. In one example, a front, central zipper provides an opening feature for the torso, while hook-and-loop fasteners provide opening features for the legs and shoulders. In this case, the hook-and-loop fasteners provide both opening and adjustment features. In other examples, the exosuit may simply have large openings, for example around the arms or neck, and elastic panels that allow the suit to be donned and doffed without specific closure mechanisms. A truncated load distribution member may be simply extended to tighten on the wearer's body. Openings may be provided to facilitate toileting so the user can keep the exosuit on, but only have to remove or open a relatively small portion to use the bathroom.

Electro-mechanical integration features attach components of the stability layer, power layer and sensor and controls layer into the base layer for integration into the exosuit. The integration features may be for mechanical, structural, comfort, protective or cosmetic purposes. Structural integration features anchor components of the other layers to the base layer. For the stability and power layers, the structural integration features provide for load-transmission to the base layer and load distribution members, and may accommodate specific degrees of freedom at the attachment point. For example, a snap or rivet anchoring a stability or power layer element may provide both load transmission to the base layer, as well as a pivoting degree of freedom. Stitched, adhesive, or bonded anchors may provide load transmission with or without the pivoting degree of freedom. A sliding anchor, for example along a sleeve or rail, may provide a translational degree of freedom. Anchors may be separable, such as with snaps, buckles, clasps or hooks; or may be inseparable, such as with stitching, adhesives or other bonding. Size adjustment features as described above may allow adjustment and customization of the stability and power layers, for example to adjust the tension of spring or elastic elements in the passive layer, or to adjust the length of actuators in the power layer.

Other integration features such as loops, pockets, and mounting hardware may simply provide attachment to components that do not have significant load transmission requirements, such as batteries, circuit boards, sensors, or cables. In some cases, components may be directly integrated into textile components of the base layer. For example, cables or connectors may include conductive elements that are directly woven, bonded or otherwise integrated into the base layer.

Electromechanical integration features may also protect or cosmetically hide components of the stability, power or sensor and controls layers. Elements of the stability layer (e.g. elastic bands or springs), power layer (e.g. flexible linear actuators or twisted string actuators) or sensor and controls layer (e.g. cables) may travel through sleeves, tubes, or channels integrated into the base layer, which can both conceal and protect these components. The sleeves, tubes, or channels may also permit motion of the component, for example during actuation of a power layer element. The sleeves, channels, or tubes may comprise resistance to collapse, ensuring that the component remains free and uninhibited within.

Enclosures, padding, fabric coverings, or the like may be used to further integrate components of other layers into the base layer for cosmetic, comfort, or protective purposes. For example, components such as motors, batteries, cables, or circuit boards may be housed within an enclosure, fully or partially covered or surrounded in padded material such that the components do not cause discomfort to the wearer, are visually unobtrusive and integrated into the exosuit, and are protected from the environment. Opening and closing features may additionally provide access to these components for service, removal, or replacement.

In some cases—particularly for exosuits configurable for either provisional use or testing—a tether may allow for some electronic and mechanical components to be housed off the suit. In one example, electronics such as circuit boards and batteries may be over-sized, to allow for added configurability or data capture. If the large size of these components makes it undesirable to mount them on the exosuit, they could be located separately from the suit and connected via a physical or wireless tether. Larger, over-powered motors may be attached to the suit via flexible drive linkages that allow actuation of the power layer without requiring large motors to be attached to the suit. Such over-powered configurations allow optimization of exosuit parameters without constraints requiring all components to be attached or integrated into the exosuit.

Electro-mechanical integration features may also include wireless communication. For example, one or more power layer components may be placed at different locations on the exosuit. Rather than utilizing physical electrical connections to the sensors and controls layer, the sensor and controls layer may communicate with the one or more power layer components via wireless communication protocols such as Bluetooth, ZigBee, ultrawide band, or any other suitable communication protocol. This may reduce the electrical interconnections required within the suit. Each of the one or more power layer components may additionally incorporate a local battery such that each power layer component or group of power layer components are independently powered units that do not require direct electrical interconnections to other areas of the exosuit.

The stability layer provides passive mechanical stability and assistance to the wearer. The stability layer comprises one or more passive (non-powered) spring or elastic elements that generate forces or store energy to provide stability or assistance to the wearer. An elastic element can have an un-deformed, least-energy state. Deformation, e.g. elongation, of the elastic element stores energy and generates a force oriented to return the elastic element toward its least-energy state. For example, elastic elements approximating hip flexors and hip extensors may provide stability to the wearer in a standing position. As the wearer deviates from the standing position, the elastic elements are deformed, generating forces that stabilize the wearer and assist maintaining the standing position. In another example, as a wearer moves from a standing to seated posture, energy is stored in one or more elastic elements, generating a restorative force to assist the wearer when moving from the seated to standing position. Similar passive, elastic elements may be adapted to the torso or other areas of the limbs to provide positional stability or assistance moving to a position where the elastic elements are in their least-energy state.

Elastic elements of the stability layer may be integrated to parts of the base layer or be an integral part of the base layer. For example elastic fabrics containing spandex or similar materials may serve as a combination base/stability layer. Elastic elements may also include discrete components such as springs or segments of elastic material such as silicone or elastic webbing, anchored to the base layer for load transmission at discrete points, as described above.

The stability layer may be adjusted as described above, both to adapt to the wearer's size and individual anatomy, as well as to achieve a desired amount of pre-tension or slack in components of the stability layer in specific positions. For example, some wearers may prefer more pre-tension to provide additional stability in the standing posture, while others may prefer more slack, so that the passive layer does not interfere with other activities such as ambulation.

The stability layer may interface with the power layer to engage, disengage, or adjust the tension or slack in one or more elastic elements. In one example, when the wearer is in a standing position, the power layer may pre-tension one or more elastic elements of the stability layer to a desired amount for maintaining stability in that position. The pre-tension may be further adjusted by the power layer for different positions or activities. In some embodiments, the elastic elements of the stability layer should be able to generate at least 5 lbs force; preferably at least 50 lbs force when elongated.

The power layer can provide active, powered assistance to the wearer, as well as electromechanical clutching to maintain components of the power or stability layers in a desired position or tension. The power layer can include one or more flexible linear actuators (FLA). An FLA is a powered actuator capable of generating a tensile force between two attachment points, over a give stroke length. An FLA is flexible, such that it can follow a contour, for example around a body surface, and therefore the forces at the attachment points are not necessarily aligned. In some embodiments, one or more FLAs can include one or more twisted string actuators. In the descriptions that follow, FLA refers to a flexible linear actuator that exerts a tensile force, contracts or shortens when actuated. The FLA may be used in conjunction with a mechanical clutch that locks the tension force generated by the FLA in place so that the FLA motor does not have to consume power to maintain the desired tension force. Examples of such mechanical clutches are discussed below. In some embodiments, FLAs can include one or more twisted string actuators or flexdrives, as described in further detail in U.S. Pat. No. 9,266,233, titled "Exosuit System," the contents of which are incorporated herein by reference. FLAs may also be used in connection with electrolaminate clutches, which are also described in the U.S. Pat. No. 9,266,233. The electrolaminate clutch (e.g., clutches configured to use electrostatic attraction to generate controllable forces between clutching elements) may provide power savings by locking a tension force without requiring the FLA to maintain the same force.

The powered actuators, or FLAs, are arranged on the base layer, connecting different points on the body, to generate forces for assistance with various activities. The arrangement can often approximate the wearer's muscles, in order to naturally mimic and assist the wearer's own capabilities. For example, one or more FLAs may connect the back of the torso to the back of the legs, thus approximating the wearer's hip extensor muscles. Actuators approximating the hip extensors may assist with activities such as standing from a seated position, sitting from a standing position, walking, or lifting. Similarly, one or more actuators may be arranged approximating other muscle groups, such as the hip flexors, spinal extensors, abdominal muscles or muscles of the arms or legs.

The one or more FLAs approximating a group of muscles are capable of generating at least 10 lbs over at least a ½ inch stroke length within 4 seconds. In some embodiments, one or more FLAs approximating a group of muscles may be capable of generating at least 250 lbs over a 6-inch stroke within ½ second. Multiple FLAs, arranged in series or parallel, may be used to approximate a single group of muscles, with the size, length, power, and strength of the FLAs optimized for the group of muscles and activities for which they are utilized.

The sensor and controls layer captures data from the suit and wearer, utilizes the sensor data and other commands to control the power layer based on the activity being performed, and provides suit and wearer data to the UX/UI layer for control and informational purposes.

Sensors such as encoders or potentiometers may measure the length and rotation of the FLAs, while force sensors measure the forces applied by the FLAs. Inertial measurement units (IMUs) measure and enable computation of kinematic data (positions, velocities and accelerations) of points on the suit and wearer. These data enable inverse dynamics calculations of kinetic information (forces, torques) of the suit and wearer. Electromyographic (EMG) sensors may detect the wearer's muscle activity in specific muscle groups. Electronic control systems (ECSs) on the suit may use parameters measured by the sensor layer to control the power layer. Data from the IMUs may indicate both the activity being performed, as well as the speed and intensity. For example, a pattern of IMU or EMG data may enable the ECS to detect that the wearer is walking at a specific pace. This information then enables the ECS, utilizing the sensor data, to control the power layer in order to provide the appropriate assistance to the wearer. Stretchable sensors may be used as a strain gauge to measure the strain of the elements in the stability layer, and thereby predict the forces in the elastic elements of the stability layer. Stretchable sensors may be embedded in the base layer or grip layer and used to measure the motion of the fabrics in the base layer and the motion of the body.

Data from the sensor layer may be further provided to the UX/UI layer, for feedback and information to the wearer, caregivers or service providers.

The UX/UI layer comprises the wearer's and others' interaction and experience with the exosuit system. This layer includes controls of the suit itself such as initiation of activities, as well as feedback to the wearer and caregivers. A retail or service experience may include steps of fitting, calibration, training and maintenance of the exosuit system. Other UX/UI features may include additional lifestyle features such as electronic security, identity protection and health status monitoring.

The assistive exosuit can have a user interface for the wearer to instruct the suit which activity is to be performed, as well as the timing of the activity. In one example, a user may manually instruct the exosuit to enter an activity mode via one or more buttons, a keypad, or a tethered device such as a mobile phone. In another example, the exosuit may detect initiation of an activity from the sensor and controls layer, as described previously. In yet another example, the user may speak a desired activity mode to the suit, which can interpret the spoken request to set the desired mode. The suit may be pre-programmed to perform the activity for a specific duration, until another command is received from the wearer, or until the suit detects that the wearer has ceased the activity. The suit may include cease activity features that, when activated, cause the suit to cease all activity. The cease activity features can take into account the motion being performed, and can disengage in a way that takes into account the user's position and motion, and safely returns the user to an unloaded state in a safe posture.

The exosuit may have a UX/UI controller that is defined as a node on another user device, such as a computer or mobile smart phone. The exosuit may also be the base for other accessories. For example, the exosuit may include a cell phone chip so that the suit may be capable of receiving both data and voice commands directly similar to a cell phone, and can communicate information and voice signals through such a node. The exosuit control architecture can be configured to allow for other devices to be added as accessories to the exosuit. For example, a video screen may be connected to the exosuit to show images that are related to the use of the suit. The exosuit may be used to interact with smart household devices such as door locks or can be used to turn on smart televisions and adjust channels and other settings. In these modes, the physical assist of the suit can be used to augment or create physical or haptic experiences for the wearer that are related to communication with these devices. For instance, an email could have a pat on the back as a form of physical emoji that when inserted in the email causes the suit to physically tap the wearer or perform some other type of physical expression to the user that adds emphasis to the written email.

The exosuit may provide visual, audio, or haptic feedback or cues to inform the user of various exosuit operations. For example, the exosuit may include vibration motors to provide haptic feedback. As a specific example, two haptic motors may be positioned near the front hip bones to inform the user of suit activity when performing a sit-to-stand assistive movement. In addition, two haptic motors may be positioned near the back hip bones to inform the user of suit activity when performing a stand-to-sit assistive movement. The exosuit may include one or more light emitting diodes (LEDs) to provide visual feedback or cues. For example, LEDS may be placed near the left and/or right shoulders within the peripheral vision of the user. The exosuit may include a speaker or buzzer to provide audio feedback or cues.

In other instances, the interaction of the FLA's with the body through the body harness and otherwise can be used as a form of haptic feedback to the wearer, where changes in the timing of the contraction of the FLA's can indicate certain information to the wearer. For instance, the number or strength of tugs of the FLA on the waist could indicate the amount of battery life remaining or that the suit has entered a ready state for an impending motion.

The control of the exosuit may also be linked to the sensors that are measuring the movement of the wearer, or other sensors, for instance on the suit of another person, or sensors in the environment. The motor commands described herein may all be activated or modified by this sensor information. In this example, the suit can exhibit its own reflexes such that the wearer, through intentional or unintentional motions, cues the motion profile of the suit. When sitting, for further example, the physical movement of leaning forward in the chair, as if to indicate an intention to stand up, can be sensed by the suit IMU's and be used to trigger the sit to stand motion profile. In one embodiment, the exosuit may include sensors (e.g., electroencephalograph (EEG) sensor) that are able to monitor brain activity may be used to detect a user's desire to perform a particular movement. For example, if the user is sitting down, the EEG sensor may sense the user's desire to stand up and cause the exosuit to prime itself to assist the user in a sit-to-stand assistive movement.

The suit may make sounds or provide other feedback, for instance through quick movements of the motors, as information to the user that the suit has received a command or to describe to the user that a particular motion profile can be applied. In the above reflex control example, the suit may provide a high pitch sound and/or a vibration to the wearer to indicate that it is about to start the movement. This information can help the user to be ready for the suit movements, improving performance and safety. Many types of cues are possible for all movements of the suit.

Control of the suit includes the use of machine learning techniques to measure movement performance across many instances of one or of many wearers of suits connected via the internet, where the calculation of the best control motion for optimizing performance and improving safety for any one user is based on the aggregate information in all or a subset of the wearers of the suit. The machine learning techniques can be used to provide user specific customization for exosuit assistive movements. For example, a particular user may have an abnormal gait (e.g., due to a car accident) and thus is unable to take even strides. The machine learning may detect this abnormal gait and compensate accordingly for it.

FIGS. 1A-1C show front, back, and side views of a base layer 100 of an exosuit according to an embodiment. Base layer 100 may be worn as a single piece or as multiple pieces. As shown, base layer 100 is shown to represent multiple pieces that can serve as load distribution members (LDMs) for the power layer (shown in FIGS. ID-1F). Base layer 100 and any LDMs thereof can cover or occupy any part of the human body as desired. The LDMs shown in FIGS. 1A-1C are merely illustrative of a few potential locations and it should be appreciated that additional LDMs may be added or certain LDMs may be omitted.

Base layer 100 can include calf LDMs 102 and 104 that are secured around the calf region or lower leg portion of the human. Calf LDMs 102 and 104 are shown to be positioned between the knees and the ankles, but this is merely illustrative. If desired, calf LDM 102 and 104 can also cover the foot and ankle and/or the knee.

Base layer 100 can include thigh LDMs 106 and 108 that are secured around the thigh region of the human. Thigh LDMs 106 and 108 are shown to be positioned between the knees and an upper region of the thighs. In some embodiments, thigh LDMs 106 and 108 and calf LDMs 102 and 104, respectively, may be merged together to form leg LDMs that cover the entirety of the legs and/or feet.

Base layer 100 can include hip LDM 110 that is secured around a hip region of the human. LDM 110 may be bounded such that it remains positioned above the toileting regions of the human. Such bounding may make toileting relatively easy for the human as he or she would be not be required to remove base layer 100 to use the bathroom. In some embodiments, LDM 110 may be attached to thigh LDMs 106 and 108, but the toileting regions may remain uncovered. In another embodiment, a removable base layer portion may exist between LDM 100 and thigh LDMS 106 and 108.

Base layer 100 can include upper torso LDM 112 that is secured around an upper torso region of the human. Upper torso LDM 112 may include waist LDM 113, back LDM 114, shoulder LDM 115, and shoulder strap LDMs 116. Waist LDM 113, back LDM 114, shoulder LDM 115, and shoulder strap LDMs 116 may be integrally formed to yield upper torso LDM 112. In some embodiments, a chest LDM (not shown) may also be integrated into upper torso LDM 112. Female specific exosuits may have built in bust support for the chest LDM.

Base layer 100 can include upper arm LDMs 120 and 122 and lower arm LDMs 124 and 126. Upper arm LDMs 120 and 122 may be secured around bicep/triceps region of the arm and can occupy space between the shoulder and the elbow. Lower arm LDMs 124 and 126 may be secured around the forearm region of the arm and can occupy the space between the elbow and the wrist. If desired, upper arm LDM 120 and lower arm LDM 124 may be integrated to form an arm LDM, and upper arm LDM 122 and lower arm LDM 126 may be integrated to form another arm LDM. In some embodiments, arm LDMS 120, 122, 124, and 126 may form part of upper torso LDM 112.

Base layer 100 can include gluteal/pelvic LDM 128 that is secured the gluteal and pelvic region of the human. LDM 128 may be positioned between thigh LDMs 106 and 108 and hip LDM 110. LDM 128 may have removable portions such as buttoned or zippered flaps that permit toileting. Although not shown in FIGS. 1A-1C, LDMs may exist for the feet, toes, neck, head, hands, fingers, elbows, or any other suitable body part.

As explained above, the LDMs may serve as attachment points for components of the power layer. In particular, the components that provide muscle assistance movements typically need to be secured in at least two locations on the body. This way, when the flexible linear actuators are engaged, the contraction of the actuator can apply a force between the at least two locations on the body. With LDMs strategically placed around the body, the power layer can also be strategically placed thereon to provide any number of muscle assistance movements. For example, the power layer may be distributed across different LDMs or within different regions of the same LDM to approximate any number of different muscles or muscle groups. The power layer may approximate muscle groups such as the abdominals, adductors, dorsal muscles, shoulders, arm extensors, wrist extensors, gluteals, arm flexors, wrist flexors, scapulae fixers, thigh flexors, lumbar muscles, surae, pectorals, quadriceps, and trapezii.

The LDMs may be designed so that they can accommodate different sizes of individuals who don the exosuit. For example, the LDMs may be adjusted to achieve the best fit. In addition the LDMs are designed such that the location of the end points and the lines of action are co-located with the bone structure of the user in such a way that the flexdrive placement on the exosuit system are aligned with the actual muscle structure of the wearer for comfort, and the moment arms and forces generated by the flexdrive/exosuit system feel aligned with the forces generated by the wearer's own muscles.

FIGS. 1D-1F show front, back, and side views, respectively, of a power layer according to an embodiment. The power layer is shown as multiple segments distributed across and within the various LDMs. As shown, the power layer can include power layer segments 140-158. Each of power layer segments can include any number of flexible linear actuators. Some of the power layer segments may exist solely on the anterior side of the body, exist solely on the posterior side, start on the anterior side and wrap around to the posterior side, start on the posterior side and wrap around to the anterior side, or wrap completely around a portion of the body. Power layer segment (PLS) 140 may be secured to LDM 102 and LDM 106, and PLS 141 may be secured to LDM 104 and LDM 108. PLS 142 may be secured to LDM 106 and LDM 110 and/or LDM 114, and PLS 143 may be secured to LDM 108 and LDM 110 and/or LDM 114. PLS 145 may be secured to LDM 110 and LDM 113 and/or to LDM 114 or LDM 128. PLS 146 may be secured to LDM 115 and LDM 120, and PLS 147 may be secured to LDM 115 and LDM 122. PLS 148 may be secured to LDM 120 and LDM 124, and PLS 149 may be secured to LDM 122 and LDM 126.

PLS 150 may be secured to LDM 104 and LDM 108, and PLS 151 may be secured to LDM 102 and LDM 106. PLS 152 may be secured to LDM 106 and LDM 110 and/or to LDM 113, and PLS 153 may be secured to LDM 108 and LDM 110 and/or LDM 113. PLS 154 may be secured to LDM 112 and LDM 110. PLS 155 may be secured to LDM 112 and LDM 120, and PLS 156 may be secured to LDM 112 and LDM 122. PLS 157 may be secured to LDM 120 and LDM 124, and PLS 158 may be secured to LDM 122 and LDM 126.

It should be appreciated that the power layer segments are merely illustrative and that additional power layer segments may be added or that some segments may be omitted. In addition, the attachment points for the power layer segments are merely illustrative and that other attachment points may be used.

The human body has many muscles, including large and small muscles that are arranged in all sorts of different configuration. For example, FIGS. 1G and 1H show respective front and back views of a human male's musculature anatomy, which shows many muscles. In particular, the abdominals, adductors, dorsal muscles, shoulders, arm extensors, wrist extensors, gluteals, arm flexors, wrist flexors, scapulae fixers, thigh flexors, lumbar muscles, pectorals, quadriceps, and trapezii are all shown.

Figure 1I:
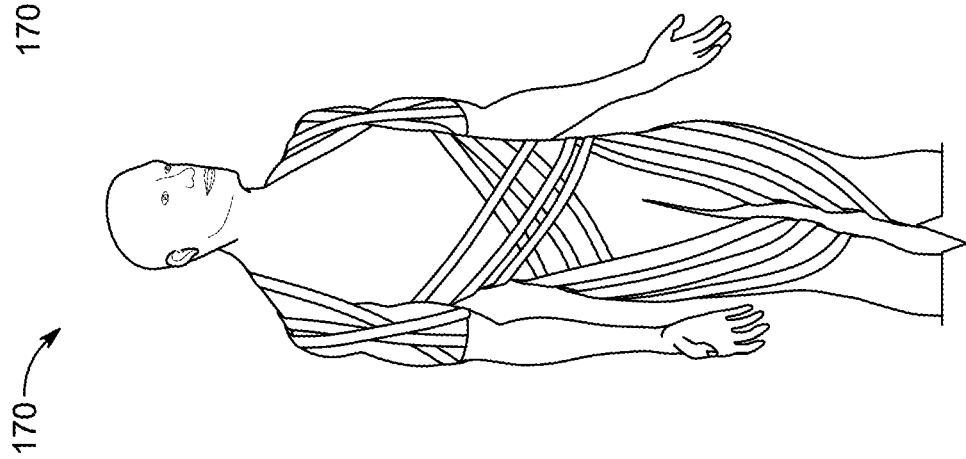
Figure 1H:
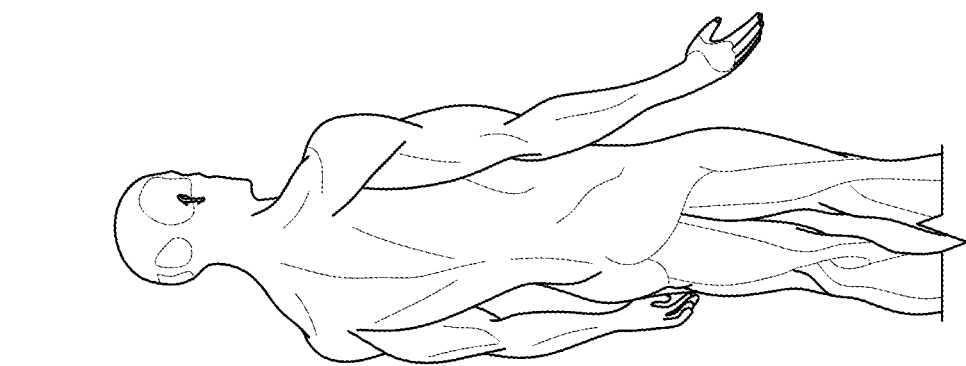
FIGS. 1G and 1H show respective front and back views of a human male's musculature anatomy, according to an embodiment.
Figure 1G:
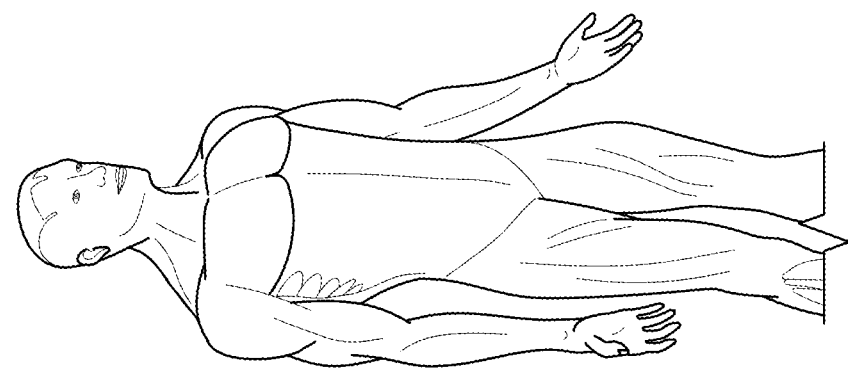

FIGS. 1I and 1J show front and side views of illustrative exosuit 170 having several power layer segments that approximate many of the muscles shown in FIGS. 1G and 1H. The power layer segments are represented by the individual lines that span different parts of the body. These lines may represent specific flexible linear actuators or groups thereof that work together to form the power layer segments that are secured to the LDMs (not shown). As shown, the FLAs may be arrayed to replicate at least a portion of each of the abdominal muscles, dorsal muscles, shoulder muscles, arm extensor and flexor muscles, gluteal muscles, quadriceps muscles, thigh flexor muscles, and trapezii muscles. Thus, exosuit 170 exemplifies one of many possible different power layer segment arrangements that may be used in exosuits in accordance with embodiments discussed herein. Other possible power layer segment arrangements are illustrated and discussed below.

The power layer segments may be arranged such that they include opposing pairs or groups, similar to the way human muscles are arranged in opposing pairs or groups of muscles. That is, for a particular movement, the opposing pairs or groups can include protagonist and antagonist muscles. While performing the movement, protagonist muscles may perform the work, whereas the antagonist muscles provide stabilization and resistance to the movement. As a specific example, when a user is performing a curl, the biceps muscles may serve as the protagonist muscles and the triceps muscles may serve as the antagonist muscles. In this example, the power layer segments of an exosuit may emulate the biceps and triceps. When the biceps human muscle is pulling to bend the elbow, the exosuit triceps power layer segment can pull on the other side of the joint to resist bending of the elbow by attempting to extend it. The power layer segment can be, for example, either be a FLA operating alone to apply the force and motion, or a FLA in series with an elastic element. In the latter case, the human biceps would be working against the elastic element, with the FLA adjusting the length and thereby the resistive force of the elastic element.

Thus, by arranging the power layer segments in protagonist and antagonist pairs, the power layers segments can mimic or emulate any protagonist and antagonist pairs of the human anatomy musculature system. This can be used to enable exosuits to provide assistive movements, alignment movements, and resistive movements. For example, for any exercise movement requires activation of protagonist muscles, a subset of the power layer segments can emulate activation of antagonist muscles associated with that exercise movement to provide resistance.

The design flexibility of the LDMs and PLSs can enable exosuits to be constructed in accordance with embodiments discussed herein. Using exosuits, the power layer segments can be used to resist motion, assist motion, or align the user's form.

Figure 2A:
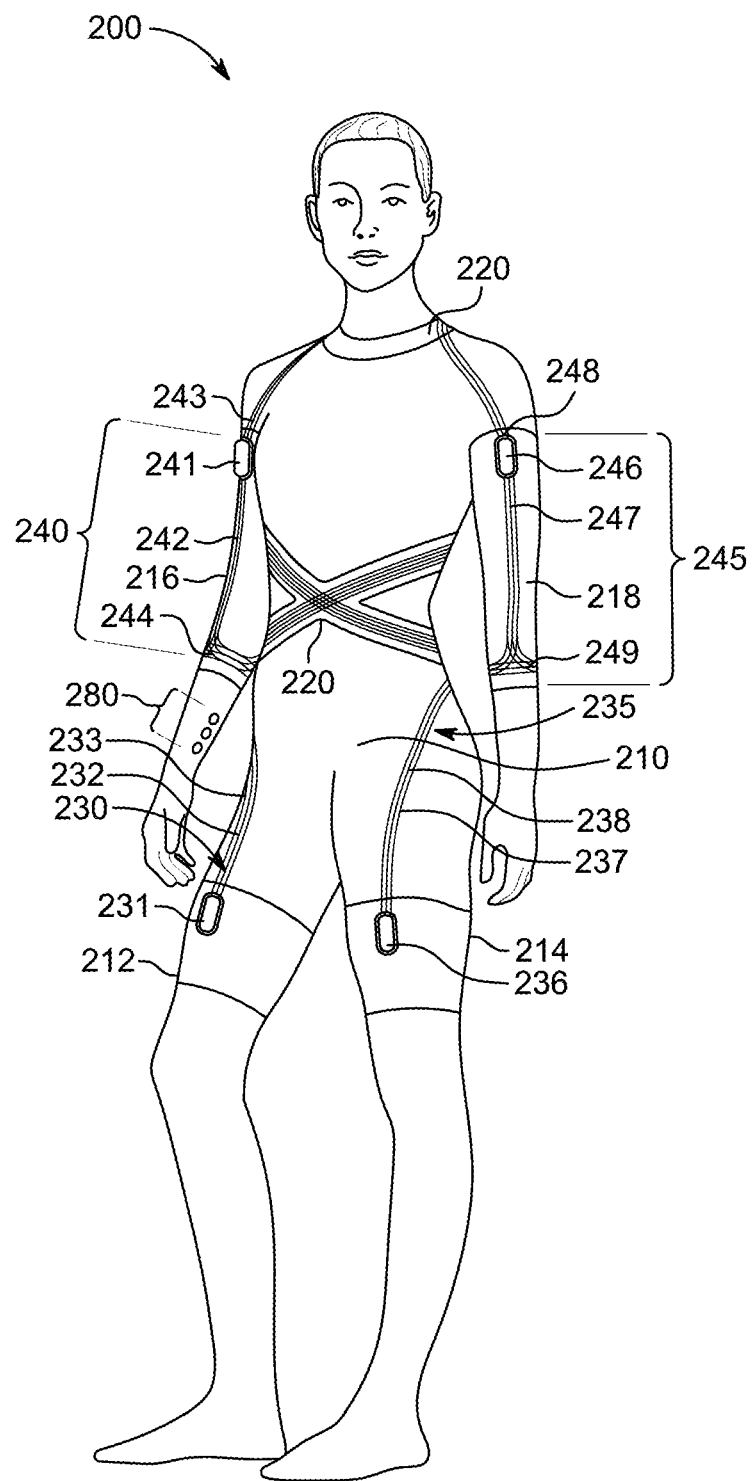
FIGS. 2A and 2B show front and back view of illustrative exosuit according to an embodiment.
Figure 2B:
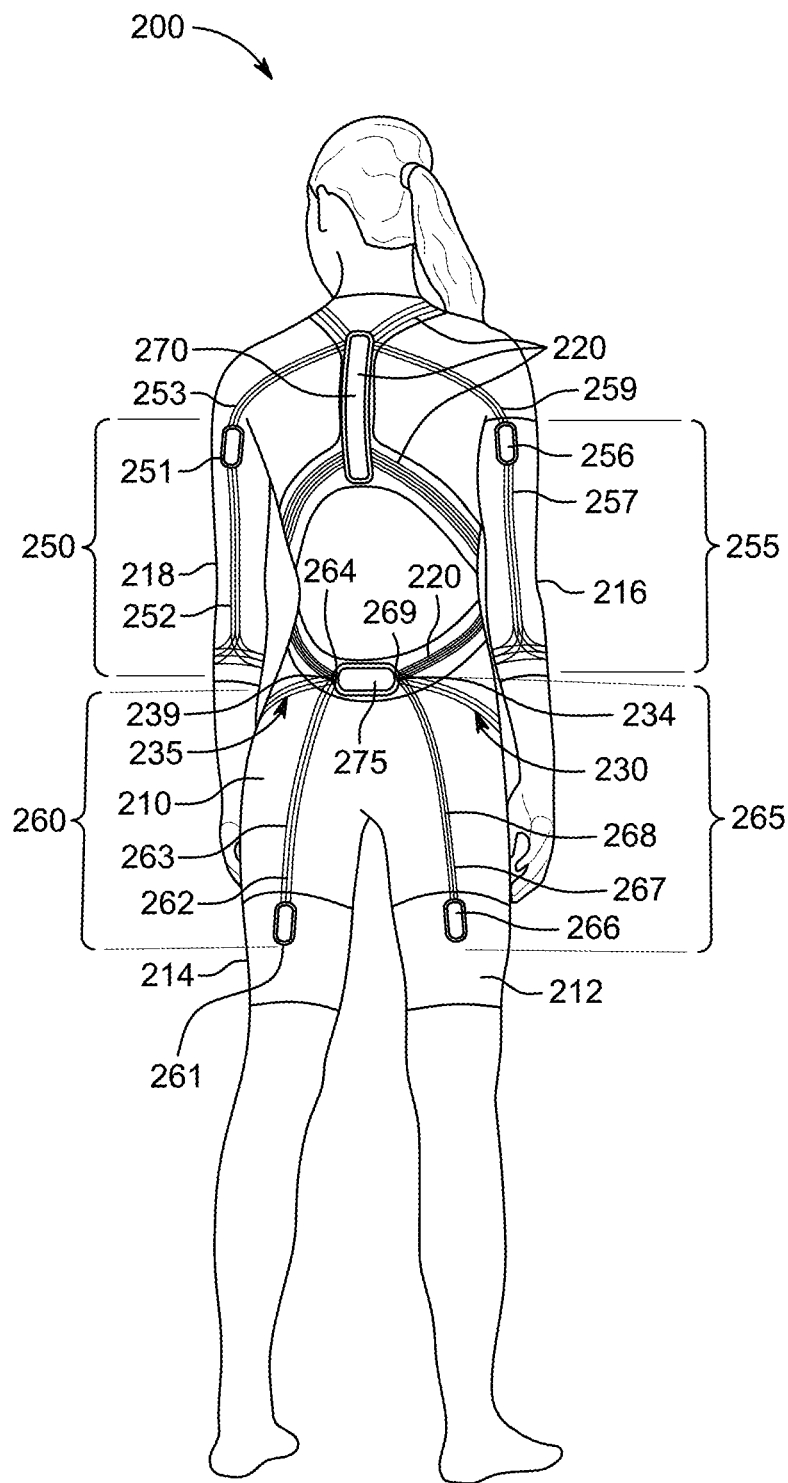

FIGS. 2A and 2B show front and back view of illustrative exosuit 200 according to an embodiment. Exosuit 200 may embody some or all of the base layer, stability layer, power layer, sensor and controls layer, a covering layer, and user interface/user experience (UI/UX) layer, as discussed above. In addition, exosuit 200 may represent one of many different specification implementations of the exosuit shown in FIGS. 1A-1F. Exosuit 200 can include base layer 210 with thigh LDMs 212 and 214, arm LDMs 216 and 218, and upper torso LDM 202. Thigh LDMs 212 and 214 may wrap around the thigh region of the human, and arm LDMs 216 and 218 may wrap around arm region (including the elbow) of the human. Upper torso LDM 220 may wrap around the torso and neck of the human as shown. In particular, LDM 220 may cross near the abdomen, abut the sacrum, cover a portion of the back, and extend around the neck.

Exosuit 200 can include extensor PLSs 230 and 235 secured to thigh LDM 212 and 214 and upper torso LDM 220. Extensor PLSs 230 and 235 may provide leg muscle extensor movements. Extensor PLS 230 may include flexdrive subsystem 231, twisted string 232, and power/communication lines 233. Flexdrive subsystem 231 may include a motor, sensors, a battery, communications circuitry, and/or control circuitry. Twisted string 232 may be attached to flexdrive subsystem 231 and an attachment point 234 on LDM 220. Power/communications lines 233 may convey control signals and/or power to flexdrive subsystem 231. Extensor PLS 235 may include flexdrive subsystem 236, twisted string 237, and power/communication lines 238. Twisted string 237 may be attached to flexdrive subsystem 236 and attachment point 239.

Exosuit 200 can include flexor PLSs 240 and 245 and extensor PLSs 250 and 255 that are secured to LDMs 216, 218, and 220 (as shown). Flexor PLSs 240 and 245 may provide arm muscle flexor movements, and extensor PLSs 250 and 255 may provide arm muscle extensor movements. Flexor PLS 240 may include flexdrive subsystem 241, twisted string 242, and power/communication lines 243. Twisted string 242 may be attached to flexdrive subsystem 241 and attachment point 244. Power/communication lines 243 may be coupled to power and communications module 270. Flexor PLS 245 may include flexdrive subsystem 246, twisted string 247, and power/communication lines 248. Twisted string 247 may be attached to flexdrive subsystem 246 and attachment point 249. Power/communication lines 248 may be coupled to power and communications module 270. Extensor PLS 250 may include flexdrive subsystem 251, twisted string 252, and power/communication lines 253. Twisted string 252 may be attached to flexdrive subsystem 251 and attachment point 254. Power/communication lines 253 may be coupled to power and communications module 270. Extensor PLS 250 may include flexdrive subsystem 256, twisted string 257, and power/communication lines 258. Twisted string 256 may be attached to flexdrive subsystem 256 and attachment point 259. Power/communication lines 258 may be coupled to power and communications module 270.

Exosuit 200 can include flexor PLS 260 and 265 that are secured to thigh LDMs 212 and 214 and LDM 220. Flexor PLSs 260 and 265 may provide leg muscle flexor ARA movements. Flexor PLS 260 may include flexdrive subsystem 261, twisted string 262, and power/communication lines 263. Twisted string 262 may be attached to flexdrive subsystem 261 and attachment point 264. Power/communication lines 263 may be coupled to power and communications module 275. Flexor PLS 266 may include flexdrive subsystem 266, twisted string 267, and power/communication lines 268. Twisted string 267 may be attached to flexdrive subsystem 266 and attachment point 269. Power/communication lines 263 may be coupled to power and communications module 275

Exosuit 200 is designed to assist, resist, and align movements being performed by the user of the suit. Exosuit 200 may include many sensors in various locations to provide data required by control circuitry to provide such movements. These sensors may be located anywhere on base layer 210 and be electrically coupled to power and communications lines (e.g., 233, 237, 243, 247, 253, 257, 263, 267, or other lines). The sensors may provide absolute position data, relative position data, accelerometer data, gyroscopic data, inertial moment data, strain gauge data, resistance data, or any other suitable data.

Exosuit 200 may include user interface 280 that enables the user to control the exosuit. For example, user interface 280 can include several buttons or a touch screen interface. User interface 280 may also include a microphone to receive user spoken commands. User interface 280 may also include a speaker that can be used to playback voice recordings. Other user interface element such as buzzers (e.g., vibrating elements) may be strategically positioned around exosuit 200.

Exosuit 200 can include communications circuitry such as that contained in power and communications module 270 or 275 to communicate directly with a user device (e.g., a smartphone) or with the user device via a central sever. The user may use the user device to select one or more movements he or she would like to perform, and upon selection of the one or more movements, exosuit 200 can the assist, resist, or align movement. The user device or exosuit 200 may provide real-time alignment guidance as to the user's performance of the movement, and exosuit 200 may provide resistance, alignment, or assistance to the movement.

Figure 3C:
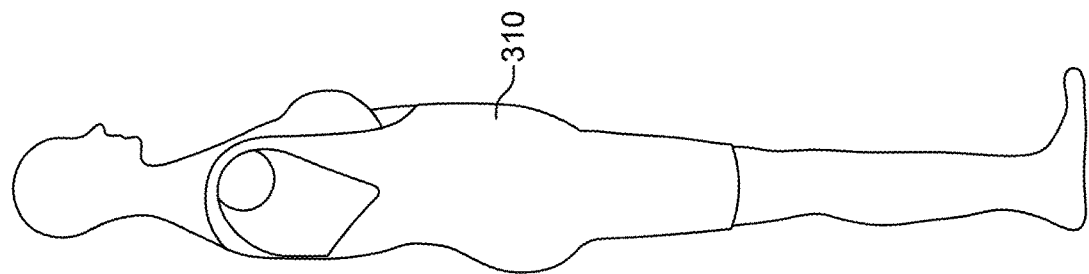
FIGS. 3A-3C show illustrative front, back, and side views of next-to-skin (N2S) layer according to an embodiment.
Figure 3B:
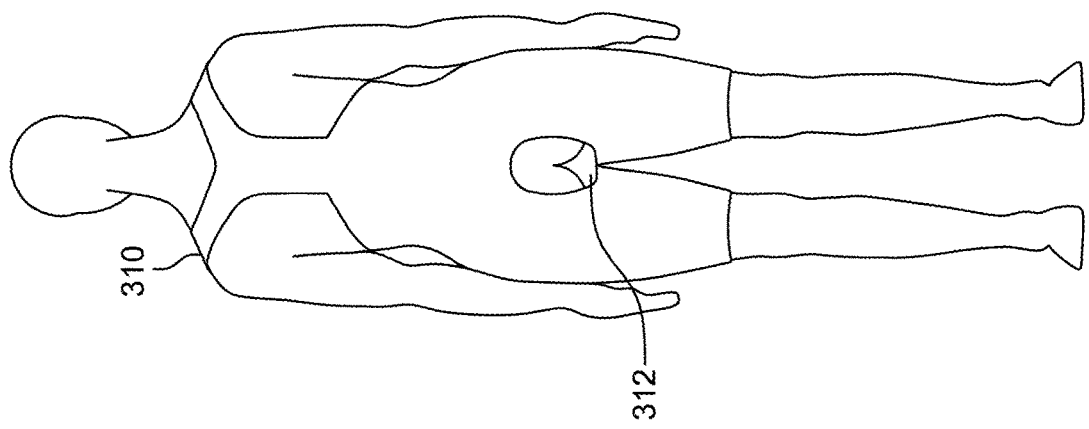
Figure 3A:
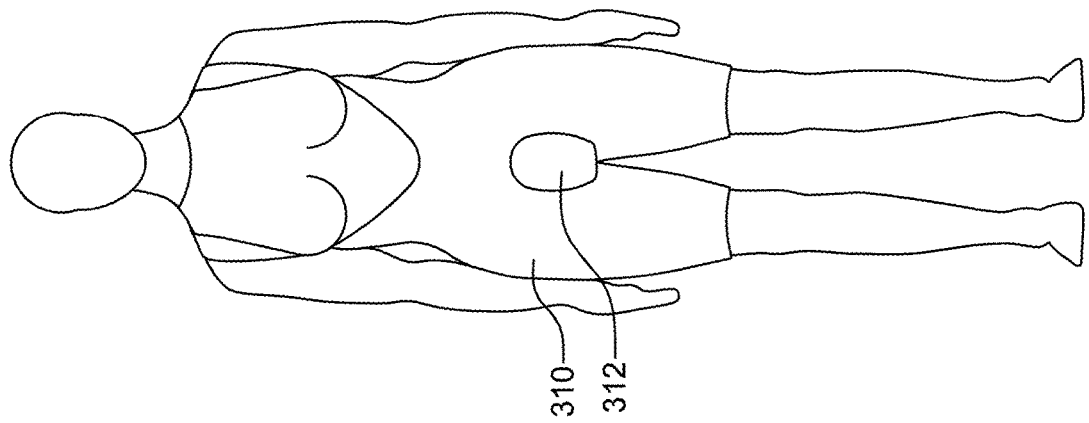

FIGS. 3A-3C show illustrative front, back, and side views of next-to-skin (N2S) layer 310 according to an embodiment. N2S layer 310 may be the inner most layer of an exosuit that makes contact with the user's body. N2S layer 310 may be constructed to cover different parts of the user and leave certain parts uncovered. For example, as shown, the arms, part of the shoulders, the lower part of the legs, chest region, and neck are not covered. In addition, toileting region 312 may also be uncovered or may include a removable material.

N2S 310 may be constructed from any suitable material. N2S 310 may be constructed from only one material type or from a combination of different material types. For example, the material types can be polyester or nylon. In some embodiments, even if N2S 310 is constructed from only one material type, that material type may be woven to exhibit different stretch profiles. For example, the stretch profiles can include little or no stretch, stretch in first, second, third, or any other desired directions, where each stretch direction is different relative to another stretch direction. N2S 310 may be constructed to have a combination of different stretch profiles. For example, a first portion of N2S 310 may include minimal stretch material, a second portion may include material that stretches in a first direction, and third portion may include material that stretches in a second direction. The material types can also exhibit different friction coefficients. Some materials may have a relatively high friction coefficient relative to human skin (to increase adherence thereto) or a relatively low friction coefficient relative to human skin (to permit relative ease in stretching against the skin and/or donning and doffing). Some portions of N2S 310 may be constructed to have a relatively high coefficient of friction with respect to load distribution members and/or power layer segments.

FIGS. 3D-3F show illustrative front, back, and side views of next-to-skin (N2S) layer 320 according to an embodiment. N2S layer 320 may be constructed to include different functional performance aspects as applied to different parts of the user. For example, functional performance can be achieved with different amounts and directional orientations of stretch, as well as adding different amounts of friction surfaces. Illustrated in FIGS. 1D-1F is N2S layer 320 having four different material types. These different materials are illustrated with cross-hatchings, dots, or solid patterns. First material 322 may be a polyester or nylon woven that has little or no stretch. First material 322 may have a relatively low profile to hide beneath clothing. Second material 324 may be a polyester or nylon stretch woven that is constructed to stretch along a first direction. Second material 324 may distribute load from the lower extremities upwards while allowing some stretch for movement and fit. Third material 326 may be another polyester or nylon woven that is constructed to stretch along a second direction. Third material 326 may be sized to allow for expansion around the circumference of the thighs and hips. Fourth material 328 may be relatively high coefficient woven or knit material that may or may not stretch. Fourth material 328 may have a relatively high amount of friction on both sides, and may be intended support a load distribution member or a power layer segment.

N2S 310 is constructed such that different material types or stretch profiles are arranged such that each material type of stretching profile is aligned with a particular portion of the user. That is, even though N2S 310 exhibits a one piece construction, the multiplicity of different stretching profiles is such that each portion of the user's body is specifically addressed to maximize comfort of fit, suitability for load distribution members, suitability for power layer support, and/or exosuit functionality. For example, as shown in FIGS. 3D-3F, third material 326 is shown to run along the sides of the body (e.g., legs, hips, and abdomen), whereas fourth material 328 is shown to be positioned adjacent to the third material 326 (e.g., in the abdomen, back, and thighs), and second material 324 occupies a remainder of the space not covered by third and fourth materials 326 and 328. First material 322 is shown to wrap around the shoulders.

Figure 3I:
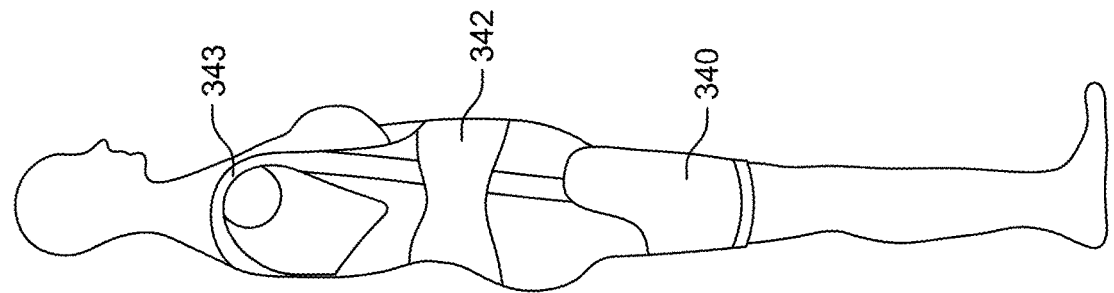
FIGS. 3G-3I show illustrative front, back, and side views of load distribution members according to an embodiment.
Figure 3H:
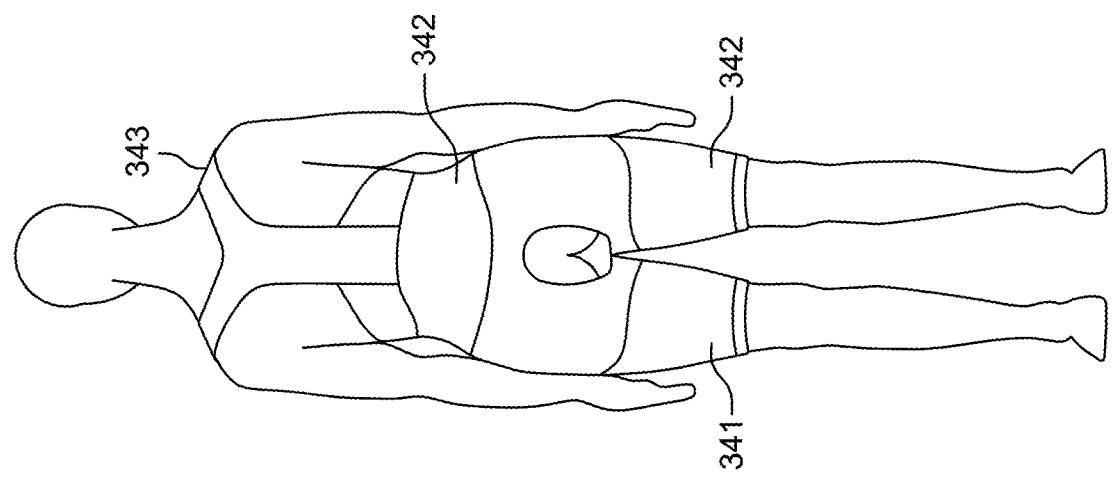
Figure 3G:
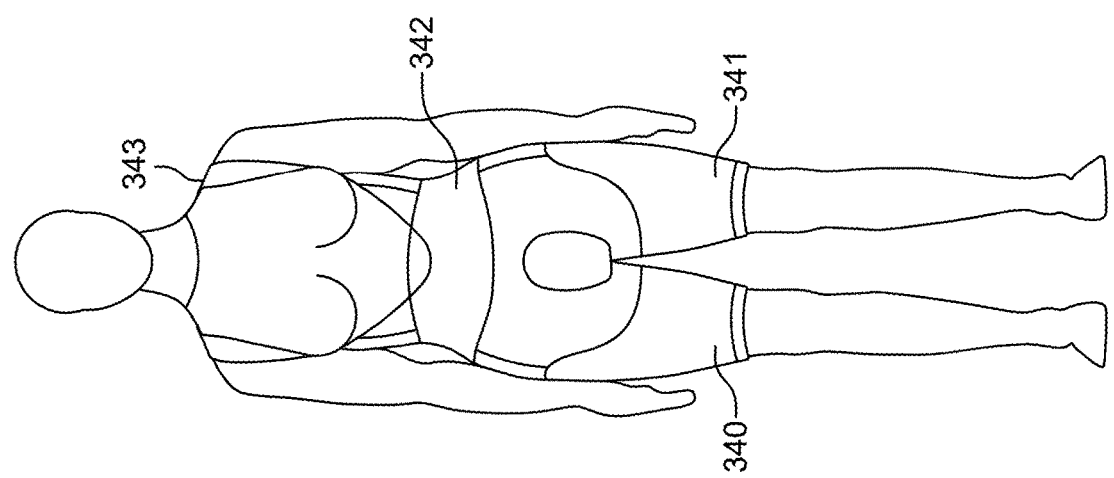

FIGS. 3G-3I show illustrative front, back, and side views of load distribution members according to an embodiment. FIGS. 3G-3I shows LDMs 340, 341, 342, and 343 positioned on top of the base layer. LMDs 340 and 341 may be associated with the thighs, LDM 342 may be associated with the core, and LDM 343 may be associated with the shoulders and back. In some embodiments, LDM 342 may be connected to LDMs 340 and 341 via a coupling member.

FIGS. 3J-3L show illustrative front, back, and side views of power layer segments according to an embodiment. FIGS. 3J-3L can include PLSs 350, 351, and 352 that are positioned on top of LDMs. PLSs 350 and 351 may be associated the thighs and are coupled to LDMS 340, 341, and 342. PLS 352 may be coupled to LDM 342.

Figure 3O:
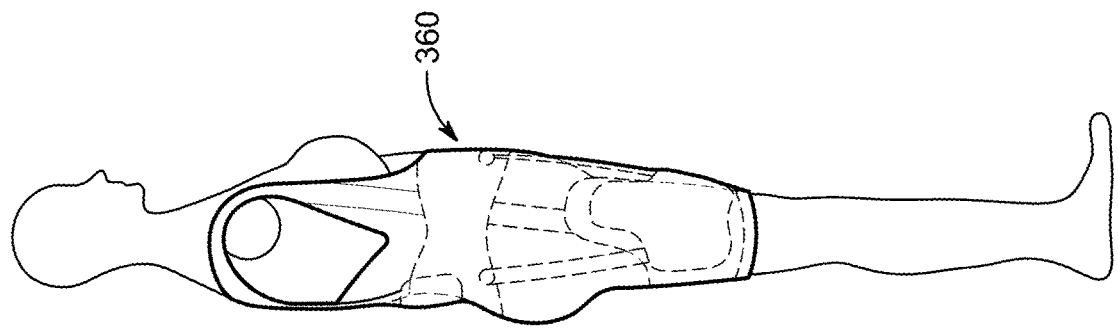
FIGS. 3M-3O show illustrative front, back, and side views of cover layer according to an embodiment.
Figure 3N:
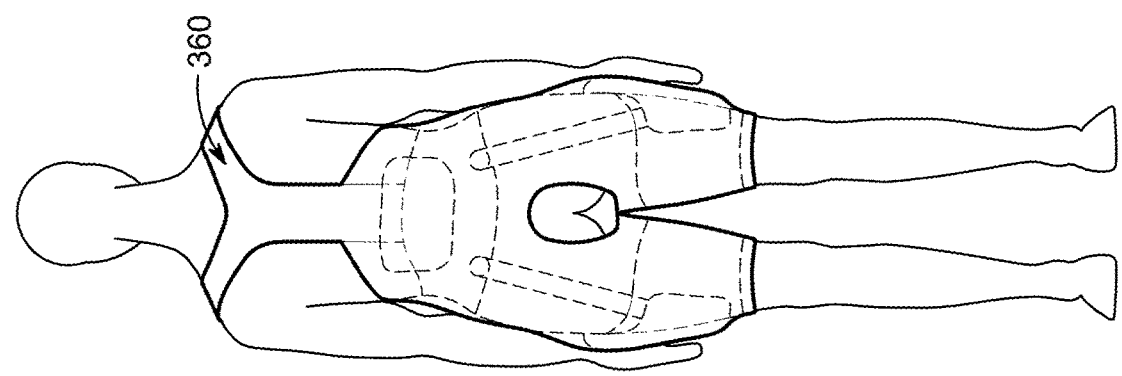
Figure 3M:
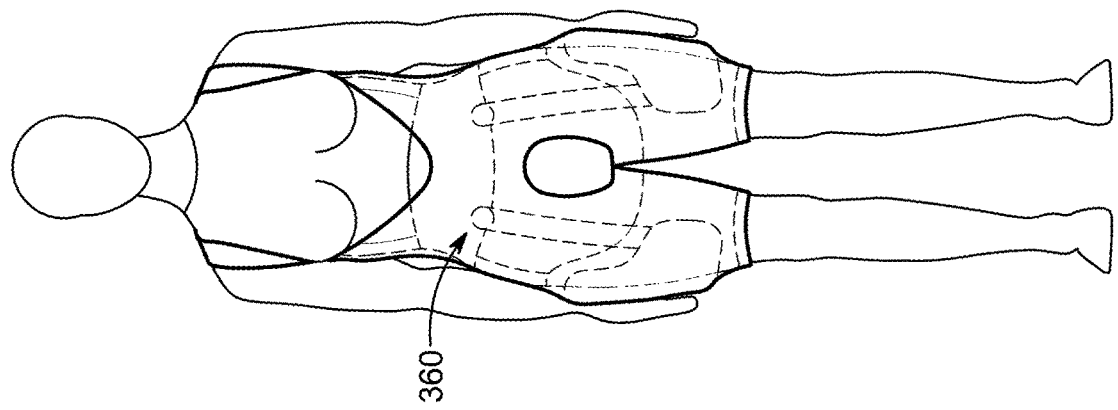

FIGS. 3M-3O show illustrative front, back, and side views of cover layer 360 according to an embodiment. Cover layer 360 may be a top layer that overlays the base layer, load distribution members, and power layer segments. Cover layer 360 may provide an aesthetic look that tastefully covers the load distribution members and power layer segments. In some embodiments, cover layer 360 may be constructed to have ribbing or knit patterns that emulate muscles of the human body.

Figure 3P:
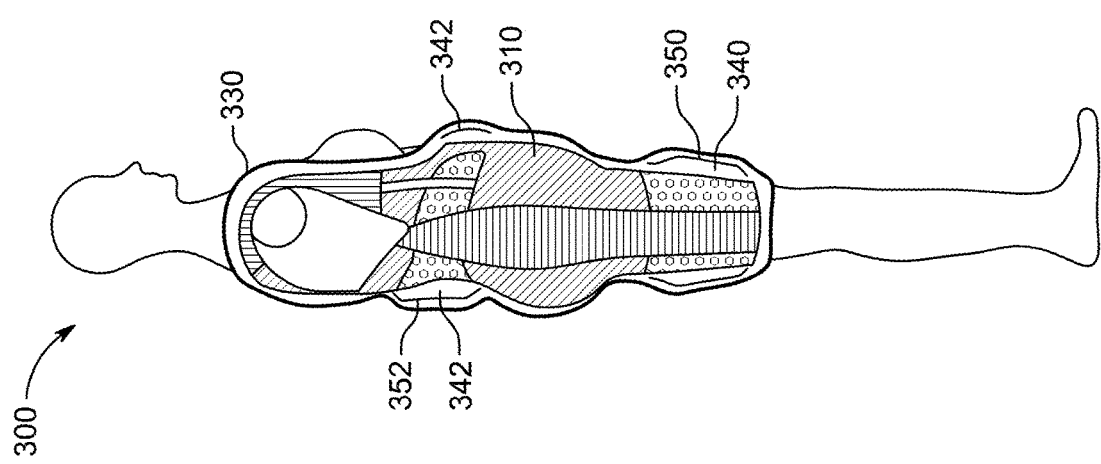
FIG. 3P shows an illustrative cross-sectional view of an exosuit according to an embodiment.

FIG. 3P shows an illustrative cross-sectional view of exosuit 300 according to an embodiment. In particular, FIG. 3P shows N2S layer 320, load distribution members 740 and 742, power layers segments 350 and 352, and cover layer 370.

FIGS. 4A-4C show illustrative front, back, and side views of next-to-skin (N2S) layer 400 according to an embodiment. N2S layer 400 may embody some of the general concepts of NS2 layer 320 (discussed above). N2S layer 400 may be constructed with first material type 402 (which is shown by the cross-hatchings), second material type 404 (which is shown by the solid texture), and friction patches 406 and 407 (which is shown by a dotted pattern). As explained in connection NS2 layer 320, the different material types may exhibit different weave patterns, material properties, friction coefficients, etc. Friction patches 406 are associated with the thighs and friction patch 407 is associated with a portion of the back. Load distribution members (not shown) may be constructed and sized to adhere to friction patches 406 and 407. N2S layer 400 may also include flap 408 and core support belt 410. Flap 408 may be button/zipper combination to promote donning and doffing. Core support belt 410 may loop around the torso region of the user and can be connected together on the front side of the wearer. Core support belt 410 may pass behind friction pad 407.

Figure 4D:
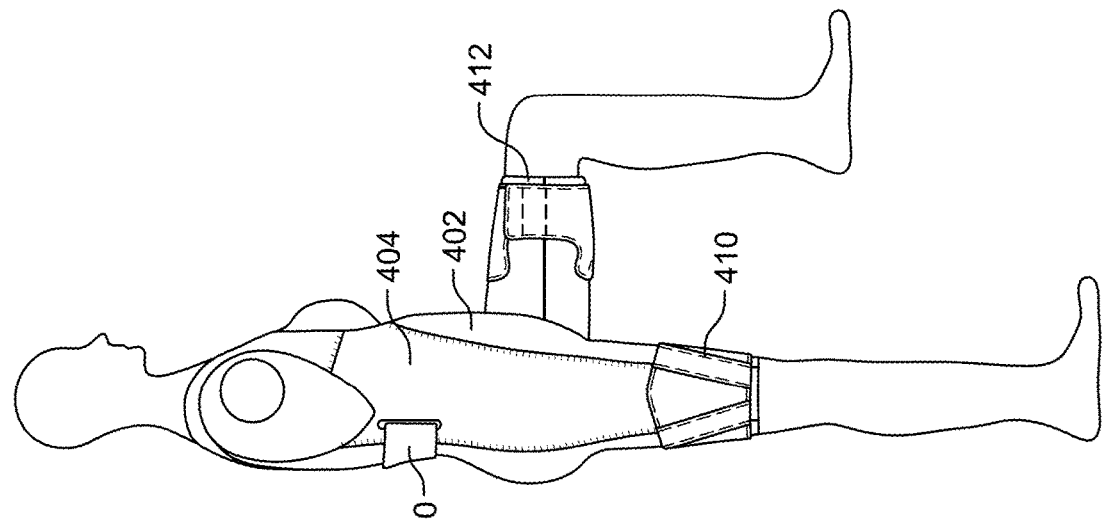
FIGS. 4D-4F show additional illustrative front, back, and side views of a N2S layer according to an embodiment.
Figure 4E:
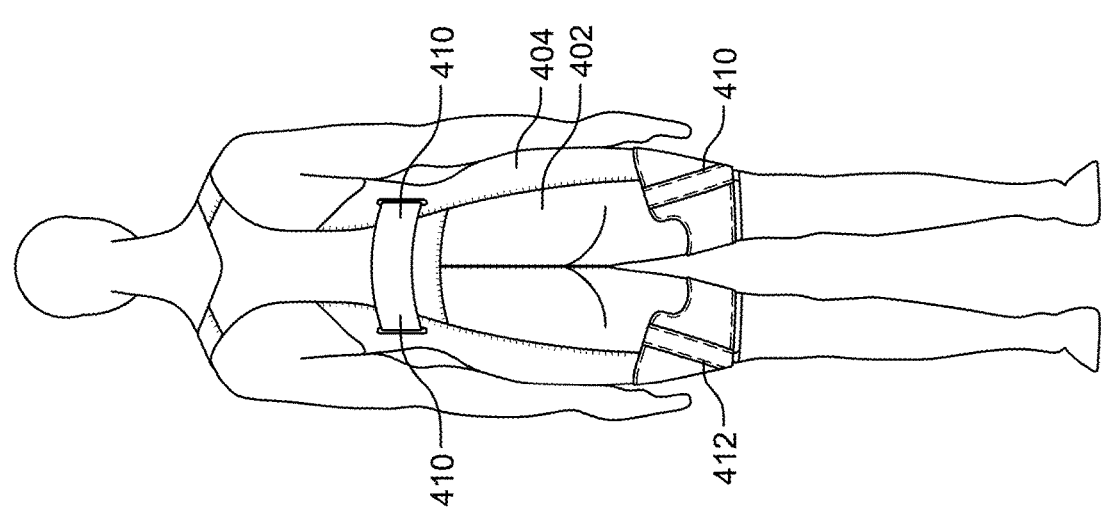
Figure 4F:
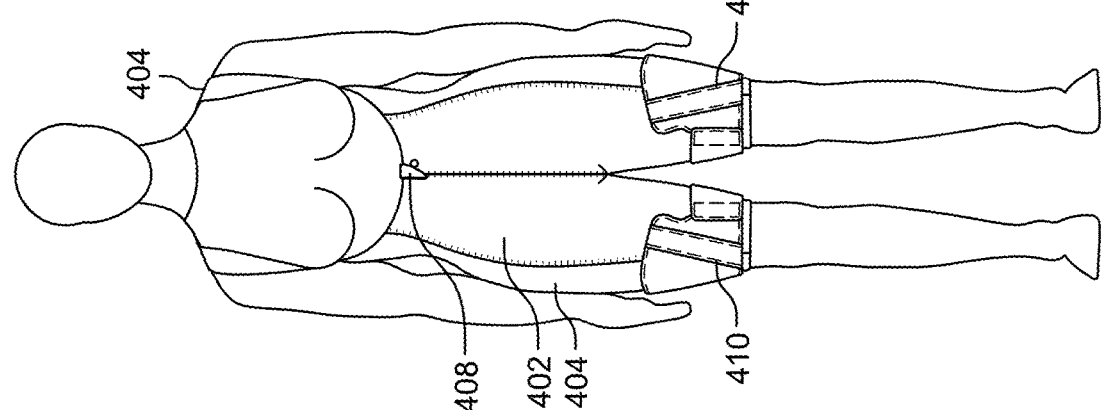

FIGS. 4D-4F show illustrative front, back, and side views of next-to-skin (N2S) layer 400 of FIGS. 4A-4C, but with the addition of load distribution members 410 and 412 according to an embodiment. Load distribution members 410 and 412 may be removable items that can wrap around friction patches 406 (not shown). LDMs 410 and 412 may be user adjustable in that the user can adjust how tightly the LDMs are wrapped around the thighs. For example, LDMs 410 and 412 may have a tensioning system the enable the user to control how tight the LDM is wrapped around the thigh. Different tensioning systems for a thigh LDM are discussed below in connection with FIGS. 5A-5C and 6A-6D. It should be appreciated that in some embodiments, friction patches may not exist and that LDMs 410 and 412 may be integrally formed components of layer 400 or may reside on top of layer 400.

Figure 5A:
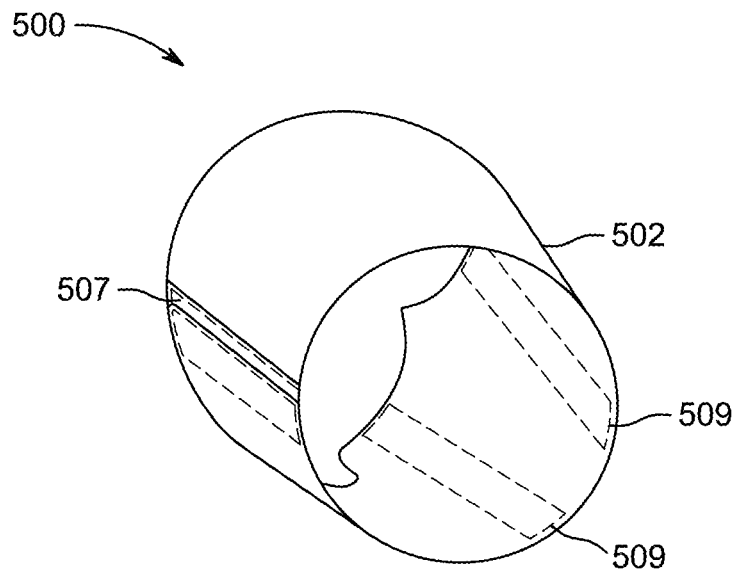
Figure 5B:
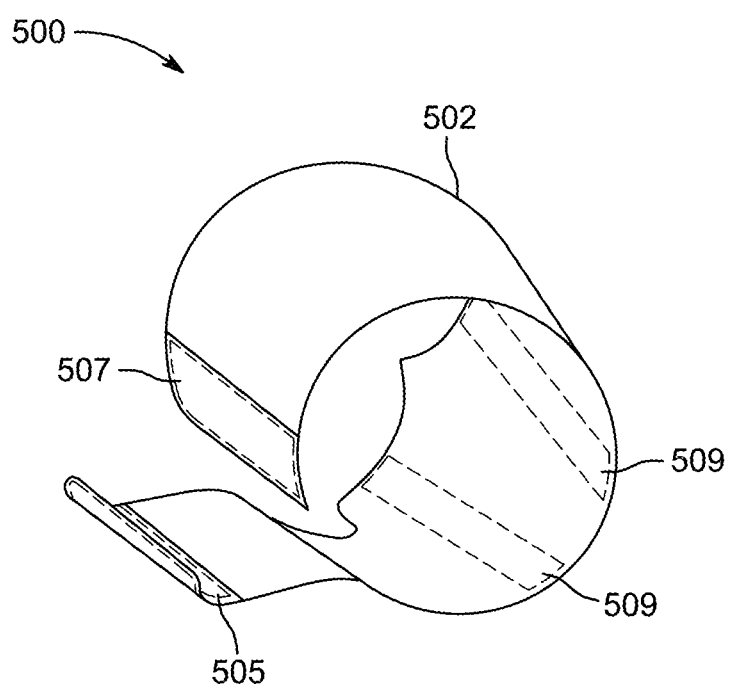

FIGS. 5A-5C show different views a thigh load distribution member 500 according to an embodiment. In particular, FIG. 5A shows LDM 500 in a closed position, FIG. 5B shows LDM 500 in an open position, and FIG. 5C shows a plan view of LDM 500. LDM 500 may be used in place of LDM 410, for example. LDM 500 can include extension portion 510 and power layer portion 512. Extension portion 510 may align with the inseam of the user wearing LDM 500. Power layer portion 512 may represent the portion of LDM 500 that can support a power layer segment (not shown). LDM 500 can include hook region 505 and loop region 507. Hook and loop regions 505 and 507 may couple together to secure LDM 500 around the thigh. LDM 500 can include a base material 502 that forms the general shape of LDM 500 and may also have loop and hook regions 505 and 507 incorporated therein. In addition, reinforcement regions 509 may be overlaid on top of base material 502. Reinforcement regions 509 may add structural support to LDM 500 and may be used to buttress power layer segments (not shown) that can be attached to LDM 500.

Figure 6A:
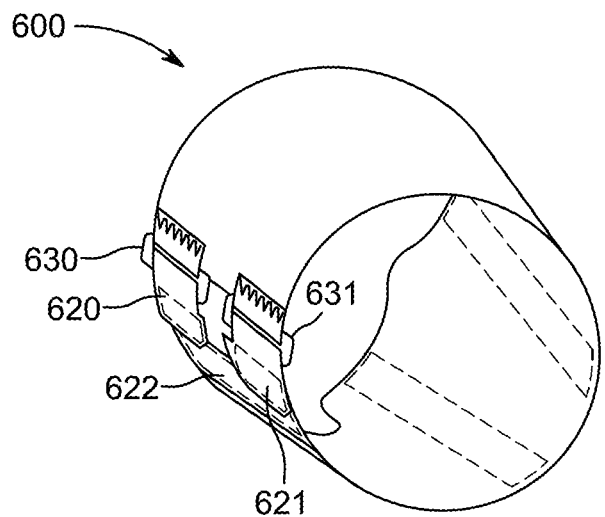
FIGS. 6A-6D show different views of a thigh load distribution member according to an embodiment.
Figure 6B:
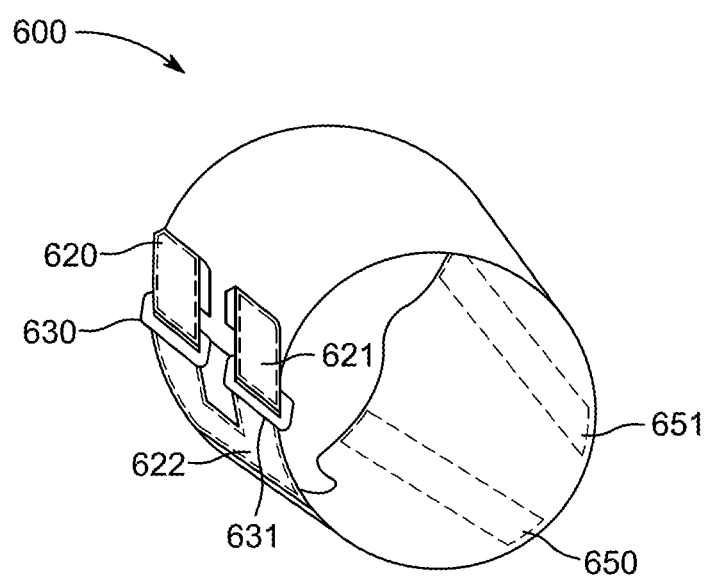
Figure 6C:
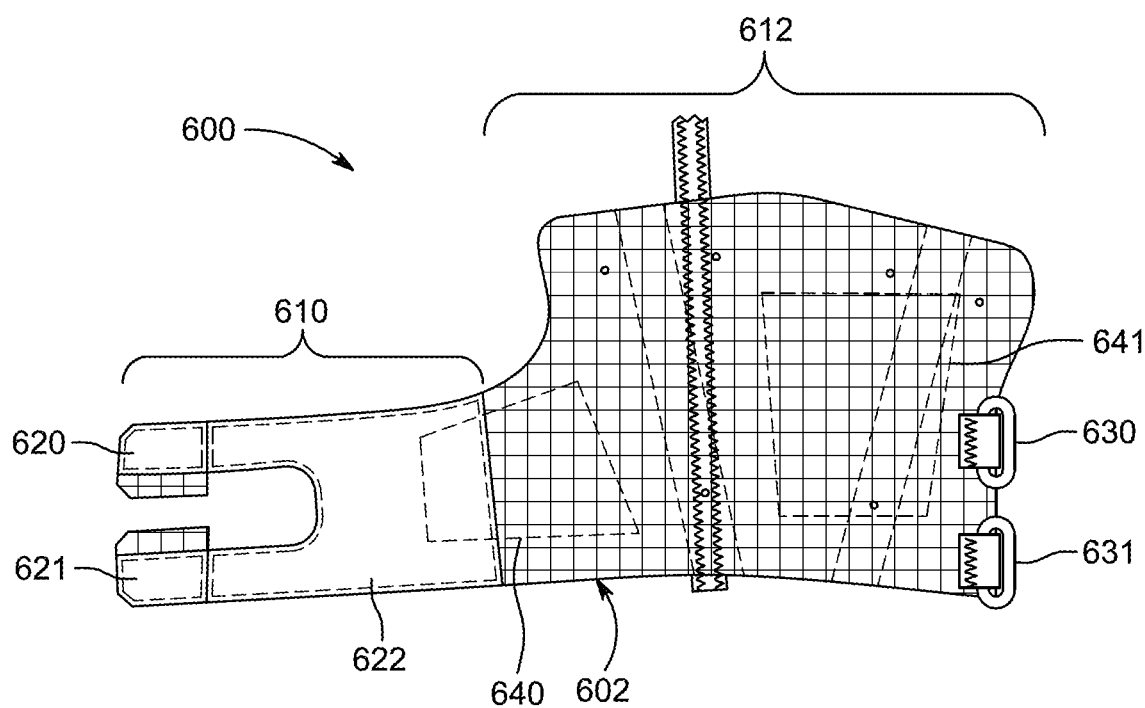
Figure 6D:
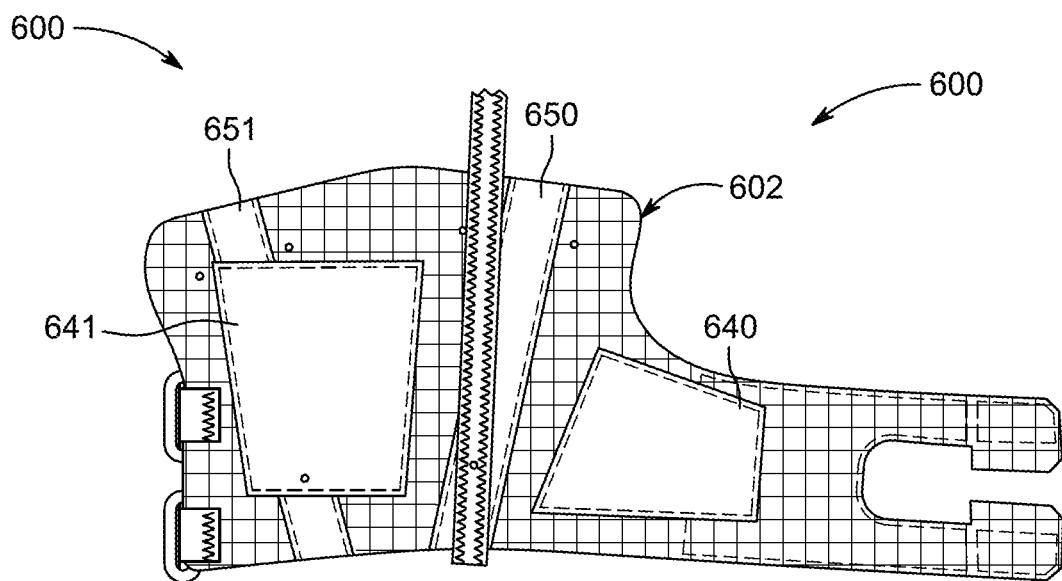

FIGS. 6A-6D show different views of a thigh load distribution member 600 according to an embodiment. In particular, FIG. 6A shows LDM 600 in a closed position, FIG. 6B shows LDM 600 in an open position, FIG. 6C shows a first plan view of LDM 600, and FIG. 6D shows a second plan view of LDM 600. LDM 600 may be used in place of LDM 410, for example. LDM 600 can include base material 602 that can logically be divided into extension portion 610 and power layer portion 612. Extension portion 610 may align with the inseam of the user wearing LDM 600. Power layer portion 612 may represent the portion of LDM 500 that can support a power layer segment (not shown).

Extension portion 610 can include hook regions 620 and 621 and loop region 622. Hook regions 620 and 621 may each be inserted through loop members 630 and 631, which are both part of power layer portion 612, and be releasably coupled to loop region 622. That is, when a user dons LDM 600, he or she may string hook regions 620 and 621 through loop members 630 and 631 and fold hook regions 620 and 621 back on top of loop region 622 to secure them place, thereby fixing LDM 600 around the thigh. LDM 600 may include stability patches 640 and 641 and reinforcement ribs 650 and 651. Stability patches 640 and 641 and reinforcement ribs 650 and 651 may provide enhanced structural stability to base material 602.

FIGS. 7A-7C show illustrative front, back, and side views of cover layer 700 according to an embodiment. Cover layer 700 may include a multi-piece construction of different structures that are designed to comfortably cover the power layer segments and next to skin layer. For example, cover layer 700 can include ribbed structures 710, knit structures 720, and mesh/perforation panels 730. Ribbed structures 710 can include array of columns stacked next to each other such that valleys exist between any two columns. The columns and valleys may be color coded to enhance visual appeal of cover layer. For example, the columns may be a first color and the valleys may be a second color. Knit structures 720 may be a plain knit material that is knitted to have, for example, a jacquard striped appearance. In some embodiments, the cover layer can be ordinary clothing such a shirt, blouse, pants, or a dress.

Cover layer 700 can also include zippers 740, 741, and 742. Zipper 740 may promote donning and doffing. Zippers 741 and 742 may be partially hidden (e.g., by fabric) and may provide access to power layer segments contained beneath cover layer 700.

FIGS. 7D-7F show illustrative front, back, and side views of cover layer 750 according to an embodiment. Cover layer 750 may include a multi-piece construction of different structures that are designed to comfortably cover the power layer segments and next to skin layer. For example, cover layer 750 can include ribbed structures 760, stripped structures 770, and mesh structures 780. Cover layer 750 can include zippers 790, 791, and 792. Zipper 790 may promote donning and doffing. Zippers 791 and 792 may provide access to power layers contained beneath cover layer 750. FIG. 7G shows a close up of circle portion G of cover layer 750. Snap 795 may attach to a reciprocal snap of a next to skin layer (e.g., N2S 310).

FIGS. 8A-8E show a leg portion of an exosuit in various states according to an embodiment. FIG. 8A shows a cover layer 860 having zipper 862 in a closed position. FIG. 8B shows zipper 862 partially open to show load distribution member 840. FIG. 8C shows snap features 895 and 896 to secure cover layer 860 to LDM 840. FIG. 8D shows hook region 841 and loop region 842 of LDM 840. FIG. 8E shows hook region 841 decoupled from loop region 842. Also shown in FIG. 8E is power layer portion 844.

FIGS. 9A-9L show illustrative front, back, and side views of a human, with emphasis on different power layer segment anchoring locations, preferred anchoring locations, projected string transmission paths, and load distribution members. Moreover, FIGS. 9A-9L may represent a more specific illustration of power layer segments and load distribution members of FIGS. 1A-1F. Starting with FIGS. 9A-9C, a human female is shown with anatomical demarcations such as over bust, bust, under bust, waist/elbow, high hip, full hip, high thigh, mid thigh, low thigh, knee, left side seam, and right side seam. Left and right side seams originate at the half way point between the neck and the shoulder bone and extend to heel when the feet are placed shoulder width apart. These anatomical demarcations provide guidepost to illustrate where different anchor locations 910 can be on the human body. Anchor locations 910 may represent locations where the power layer segment (e.g., flexible linear actuator) can be secured. Anchor locations 910 are shown by shaded areas. String zones 920 different regions through which the twisted strings associated with power layer segments should pass. The string zone in on the front of the human can exist at the full hip demarcation and in between the left and right seams. The string on the back of the human may exist at the full hip demarcation and extends slightly beyond the left and right seams. Abdomen and back based anchor locations can exist in the region bounded by the left and right seams and the waist and full hip demarcations. Thigh based anchor locations can exist between the knee and high thigh demarcations.

The combination of the anchor locations 910 and string zones 920 define lines of action. Each line of action can represent a power layer path that originates a first load distribution member, passes through a string zone, and terminates at a second load distribution member. The power layer provides an exosuit assistance movement, such as, for example, hip flexor or hip extensor movement. The actual lines of action may vary from one person to the next, such as length and angles, but the general principles remain the same.

Figure 9D:
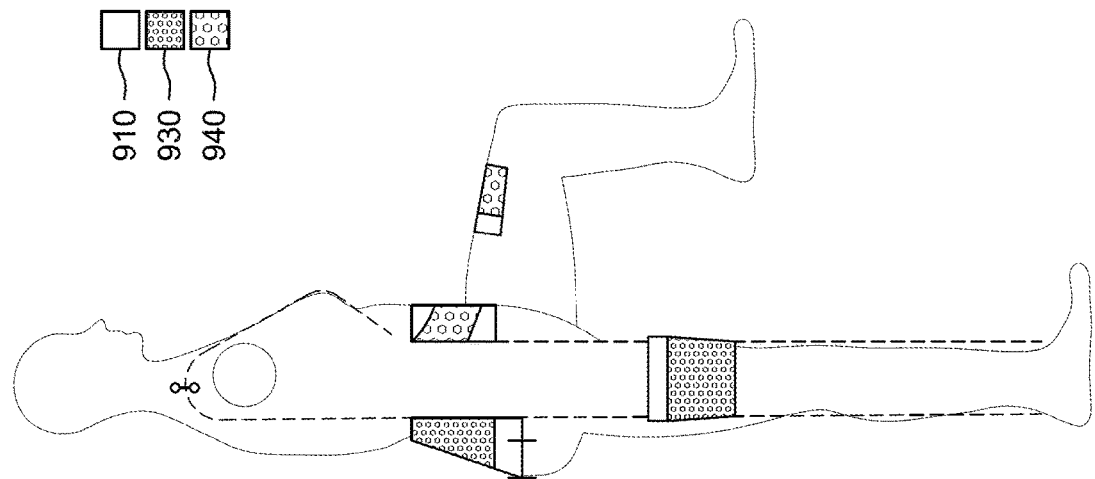
Figure 9E:
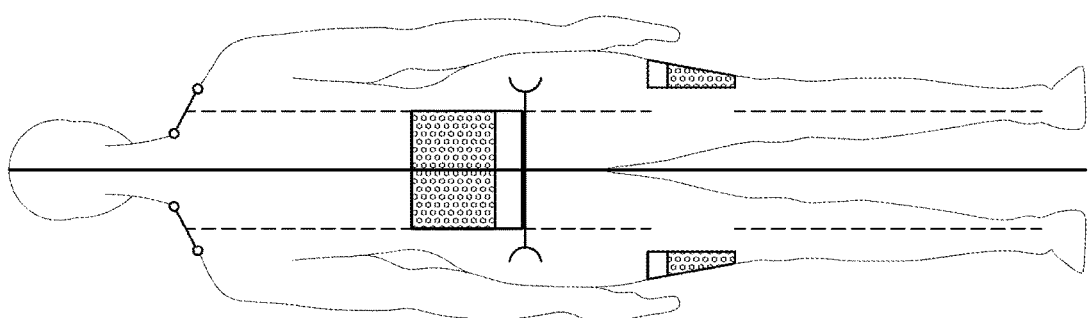
Figure 9F:
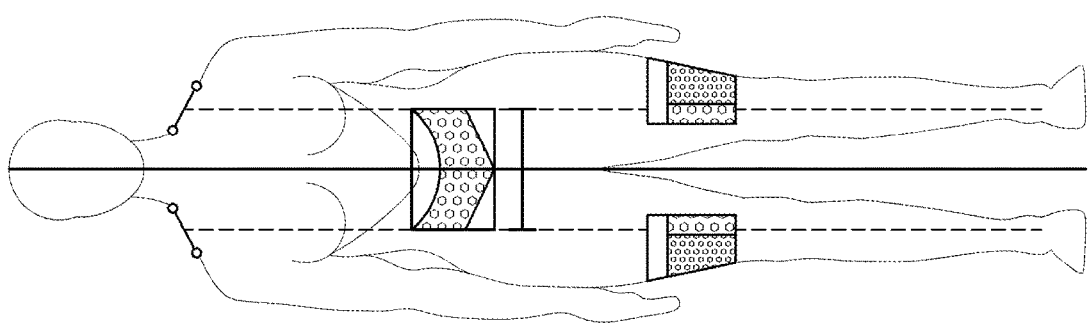
Figure 10A:
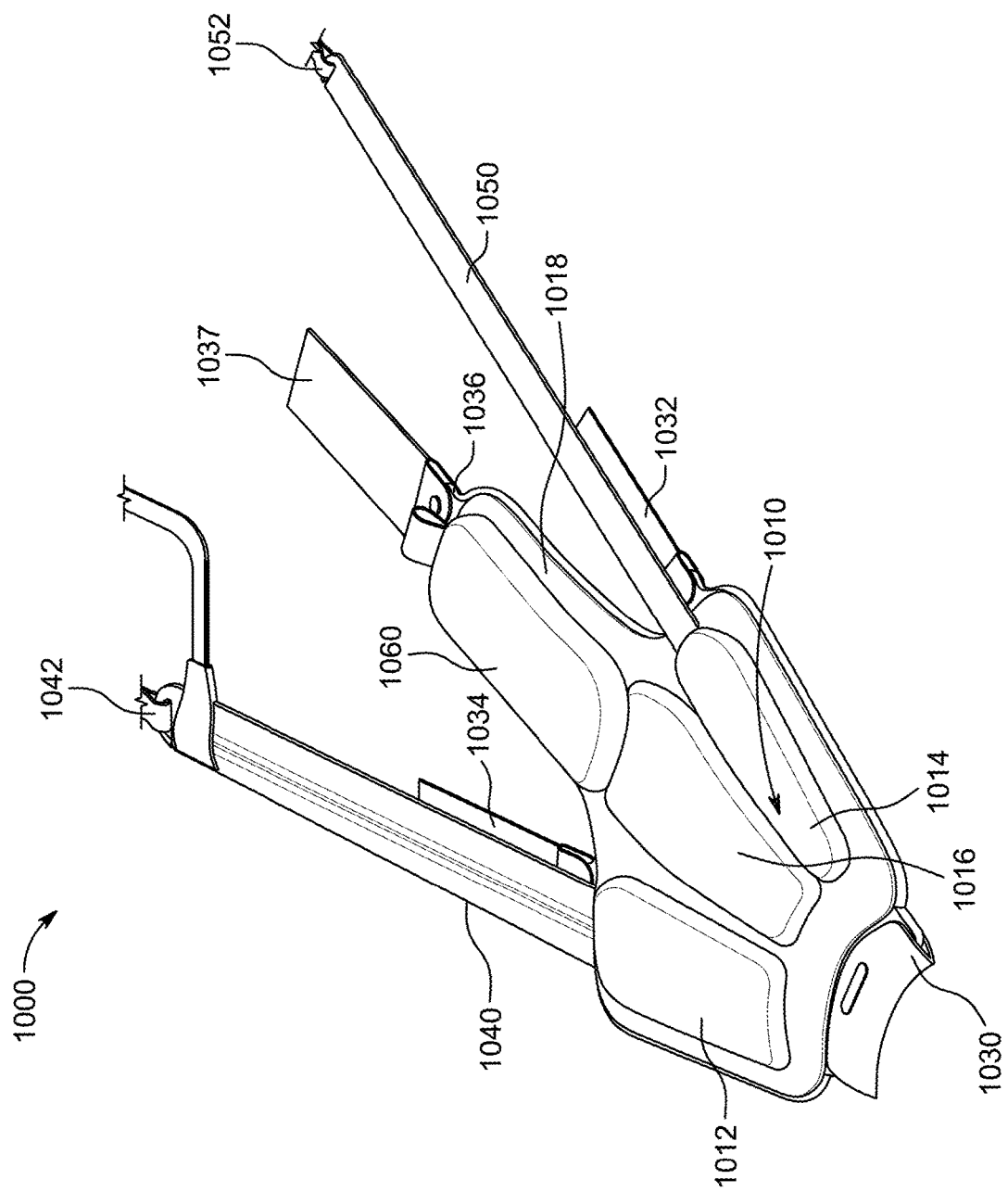
FIG. 10A-10D show an illustrative leg patch assembly according to an embodiment.
Figure 10B:
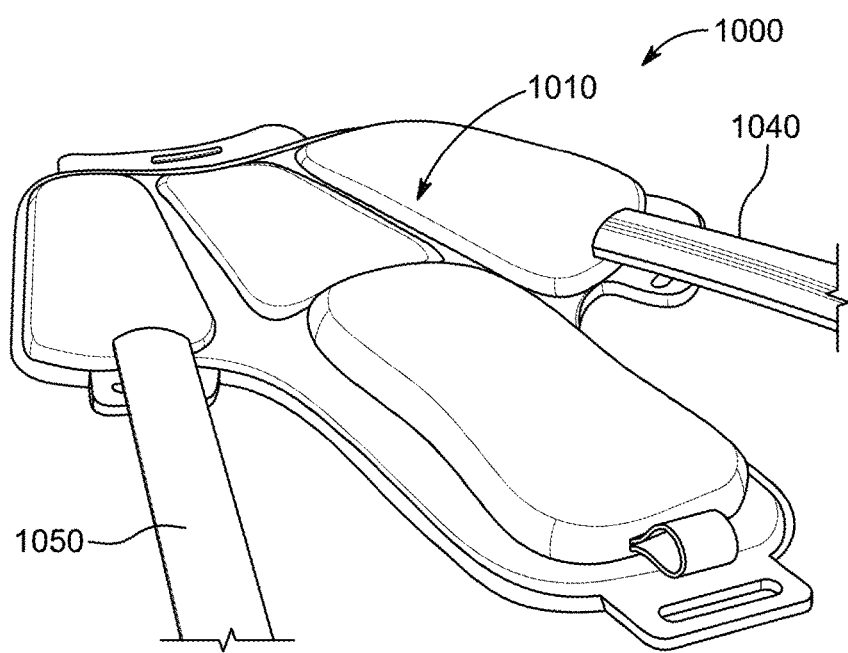
Figure 10C:
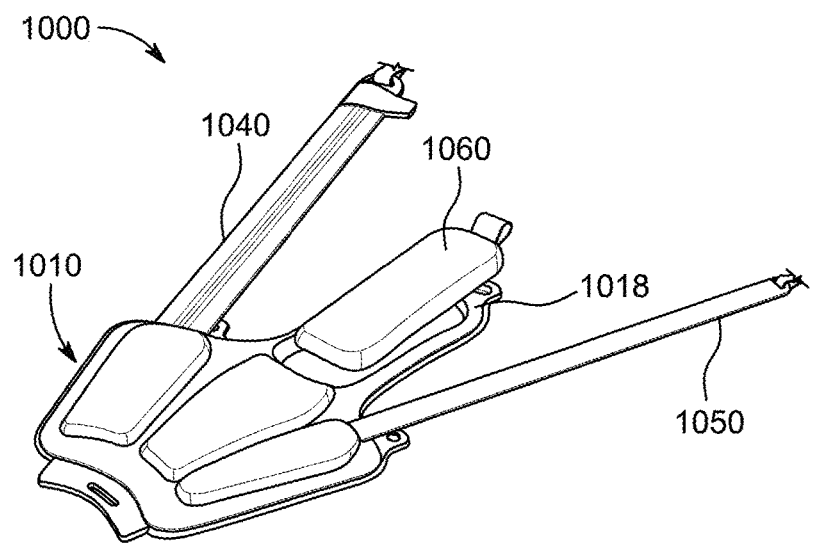
Figure 10D:
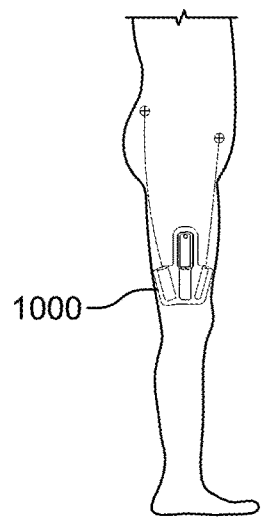

FIGS. 9D-9F show extensor anchor points 930 and flexor anchor points 940. Extensor anchor points 930 are represented by small dots, and flexor anchor points 940 are represented by big dots. Note that anchor points 930 and 940 are overlaid over anchor point locations 910.

FIGS. 9G-9I show power segments and their respective twisted strings 950 and 952. Twisted strings 950 may be associated with extensor power layer segments and twisted strings 952 may be associated with flexor power layer segments. Note that each of twisted strings 950 and 952 can serve as a line of action.

FIGS. 9J-9L show load distribution members 950 (as illustrated by shading), which are overlaid by extensor anchor points 930, flexor anchor points 940, and the twisted strings.

FIG. 10A-10D show an illustrative leg patch assembly 1000 according to an embodiment. Leg patch assembly 1000 may represent a power layer segment that is attached to a load distribution member associated with a thigh and at least one other load distribution member associated with the core region or hips. Leg patch assembly 1000 is designed to be easily secured to and removed from the load distribution members. In addition, sub-components within assembly 1000 such as, for example, a battery pack may be removed from assembly 1000 and replaced with a fully charged battery pack. Leg patch assembly 1000 can include housing 1010, base anchor 1030, first anchor 1032, second anchor 1034, suspension anchor 1036, extensor sleeve 1040, extensor anchor 1044, flexor sleeve 1050, and flexor anchor 1054. Base anchor 1030, first anchor 1032, second anchor 1034, suspension anchor 1036, extensor sleeve 1040, extensor anchor 1044, flexor sleeve 1050, and flexor anchor 1054 may take any suitable configuration for interfacing with a load distribution member. For example, in some embodiments, the anchors can be hook and loop attachments, clip attachments, button attachments, zipper attachments, buckle attachments, cord attachments, self-arresting attachments, bungee cord attachments, tongue and groove attachments, clip attachments, magnetic attachments, connector attachments, or any combination thereof. Several specific examples of anchors are discussed herein.

Housing 1010 can include extensor flexdrive portion 1012, flexor flexdrive portion 1014, electronics portion 1016, and battery portion 1018. Extensor flexdrive portion 1012 may include one or more flexdrives that are secured within housing 1010 and each have twisted strings that are contained within extensor sleeve 1040. Flexor flexdrive portion 1014 may include one or more flexdrives that are secured within housing 1010 and each have twisted strings that are contained within flexor sleeve 1050. Electronics portion 1016 may contain various electronics, circuit boards, sensors, etc., and battery portion 1018 may be constructed to receive battery pack 1060. Battery pack 1060 may be a removable and rechargeable battery pack that is designed to be retained in battery portion 1018.

When a user secures leg patch assembly 1000 to his or her exosuit, base anchor 1030, first anchor 1032, and second anchor 1034 may be secured to a thigh LDM. Securing housing 1010 to the thigh LDM via base anchor 1030, first anchor 1032, and second anchor 1034 provides a stable platform for the flexdrives to operate. Suspension anchor 1036 may be coupled to a thigh LDM or to another LDM via strap 1037. Extensor anchor 1044 may be secured to a LDM other than the thigh LDM. Flexor anchor 1054 may be secured to a LDM other than the thigh LDM. When anchors 1044 and 1054 are secured, sleeves 1040 and 1050 are positioned to enable the flexdrives to active the twisted strings contained within the sleeves to engage in assistive movement.

Figure 11:
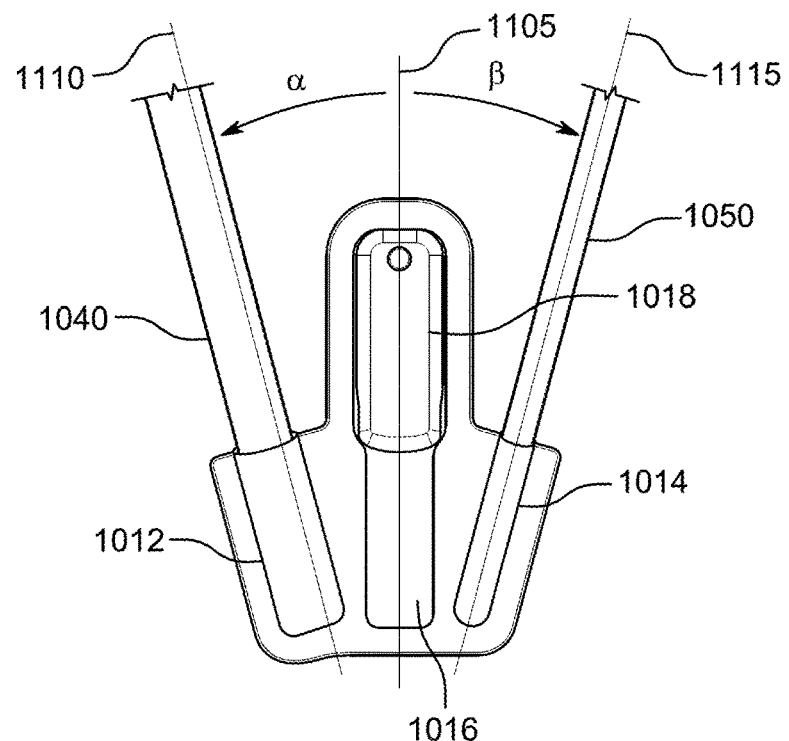
FIG. 11 shows an illustrative top view of leg patch assembly 1000 according to an embodiment.

FIG. 11 shows an illustrative top view of leg patch assembly 1000 according to an embodiment. In particular, FIG. 11 shows center axis 1105 passing through battery portion 1018 and electronics portion 1016. FIG. 11 also show extensor axis 1110 aligned with the orientation of extensor flexdrive portion 1012 and extensor sleeve 1040. FIG. 11 further shows flexor axis 1115 aligned with the orientation of flexor flexdrive portion 1014 and flexor sleeve 1050. The angle between center axis 1105 and extensor axis 1110 may be referred to as alpha, $\alpha$, and the angle between center axis 1105 and flexor axis 1115 may be referred to as beta, $\beta$. In some embodiments, alpha and beta may be the same. In other embodiments, alpha may be greater than beta. In yet other embodiments, alpha may be less than beta.

FIGS. 12A-12J show different views of a leg patch assembly 1200 according to various embodiments. Leg patch assembly 1200 can include LDM engagement housing 1210. Leg patch assembly 1200 can include housing 1210, first anchor 1230, second anchor 1232, extensor sleeve 1240, extensor anchor 1244, flexor sleeve 1250, and flexor anchor 1254. Housing 1210 may include plate member 1212 that can serve as a foundation for flexdrives, electronics, and batteries. Housing 1210 may include extensor portion 1202, flexor portion 1204, and electronics portion 1206. First and second anchors 1230 and 1232 may be integrally formed with or attached to plate member 1212 and are designed to hold flexdrives in place by preventing them from moving up along the direction of their respective sleeves when activated. For example, in one embodiment, anchors 1230 and 1232 may adhesively bonded and sewn to plate member 1212. First and second anchors 1230 and 1232 may be constructed from a plastic material such as polyurethane. Plate member 1212 may be constructed from a fabric or rubber material. For example, the material may be a chlorosulfonated polyethylene synthetic rubber, sometimes referred to as Hypalon. Snaps 1234 may be secured to plate member 1212 and provide a retention mechanism for securing cover plate 1214 to plate member 1212. Cover plate 1214 may be secured on top of plate member 1212 to cover the flexdrives and electronics. Battery 1260 may be inserted into battery region 1218 and removed as desired. Extensor anchor 1244 and flexor anchor 1254 may both have G-shaped hooks to interface with a load distribution member.

FIG. 12E shows cover plate 1214 without plate member 1212 and also shows extensor faceplate 1220 and flexor faceplate 1222. Faceplates 1220 and 1222 may be rigid members that transfer load into anchors 1230 and 1232. FIG. 12F shows cover plate 1214 positioned on top of plate member 1212, but positioned such that faceplates 1220 and 1222 are positioned below anchors 1230 and 1232. FIG. 12F shows cover plate 1214 positioned on top of plate member 1212, and positioned such that faceplates 1220 and 1222 are nestled in anchors 1230 and 1232. Thus, in FIG. 12G, anchors 1230 and 1232 interface with faceplates 1220 and 1222. FIG. 12H shows an illustrative cross-sectional view of a portion of leg patch assembly 1200 taken along line H-H of FIG. 12G. In particular, FIG. 12H shows anchor 1230 covering faceplate 1220 and how cover plate 1214 is secured to plate member 1212 via snap 1234.

Figure 12A:
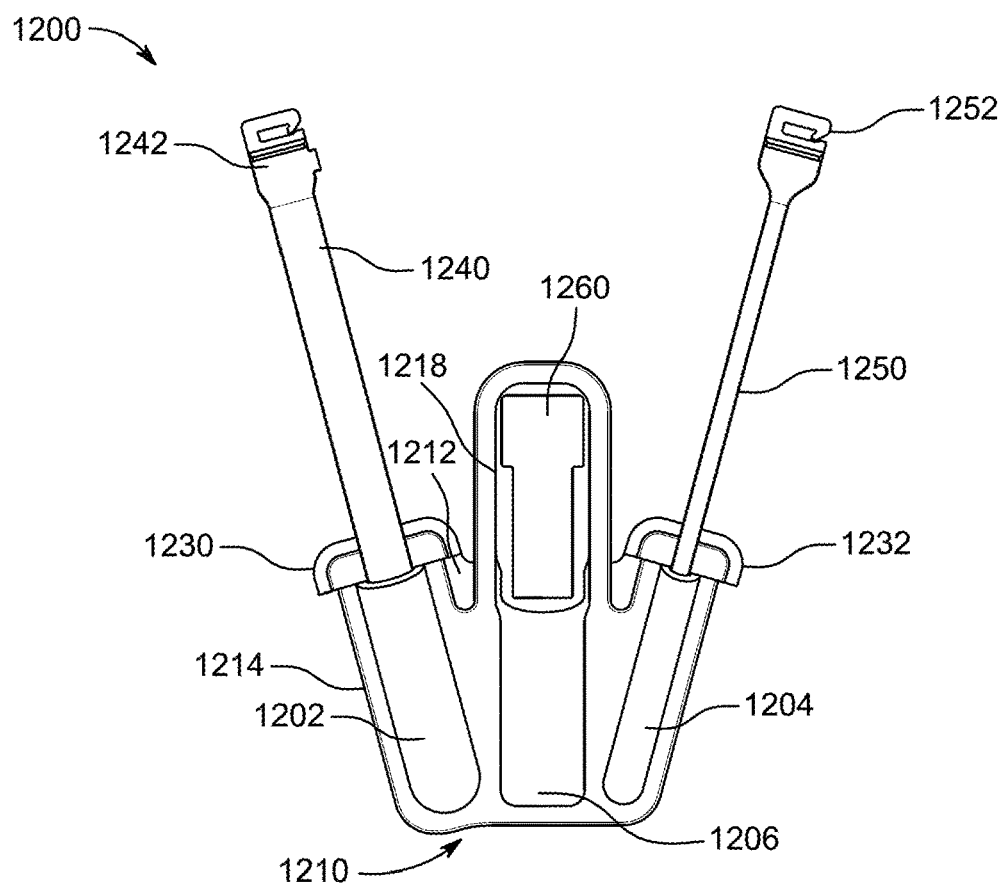
Figure 12I:
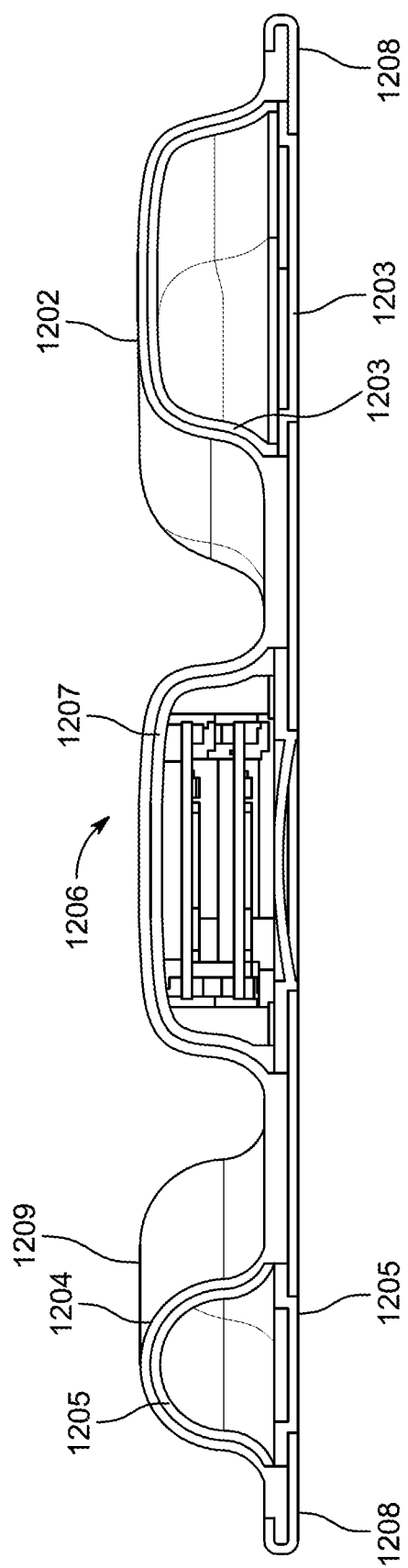

FIG. 12I shows an illustrative cross-sectional view of leg patch assembly 1200 taken along line I-I of FIG. 12E. Extensor portion 1202 can include rigid member 1203. Flexor portion 1204 can include rigid members 1205. Electronic portion 1206 can include rigid members 1207. Flexible foot member 1208 may wrap around the edge of cover layer 1212 and plate member 1212. Foam member 1209 may represent a top layer of cover layer 1214. Foam member 1209 may be a foam material that may emulate a fabric façade.

Figure 12J:
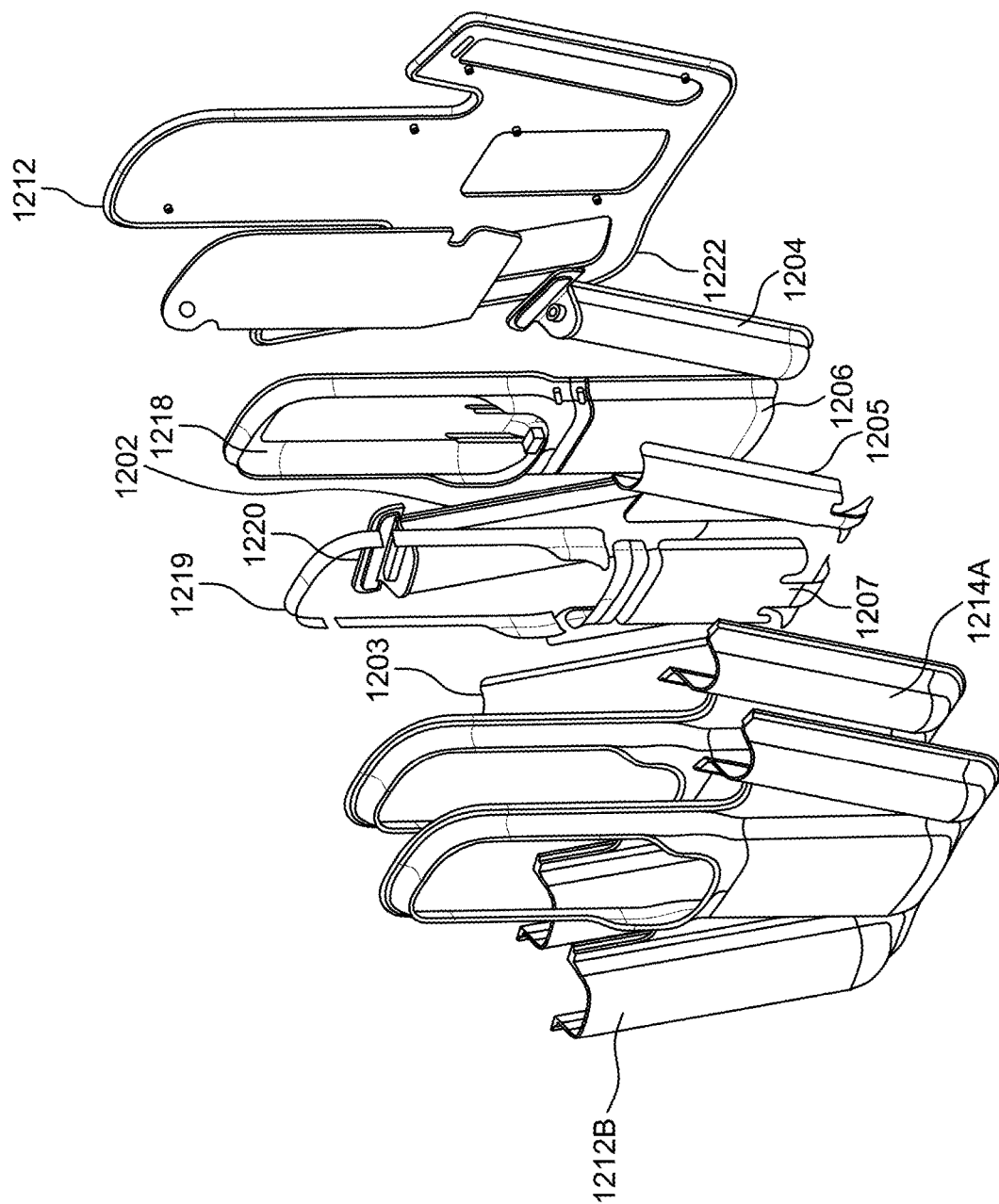

FIG. 12J shows an illustrative exploded view of leg patch assembly 1200. FIG. 12 shows two alternative cover plates 1214A and 1214B. Cover plate 1214A may be a foam cover plate and cover plate 1214B may be a fabric cover.

Figure 12K:
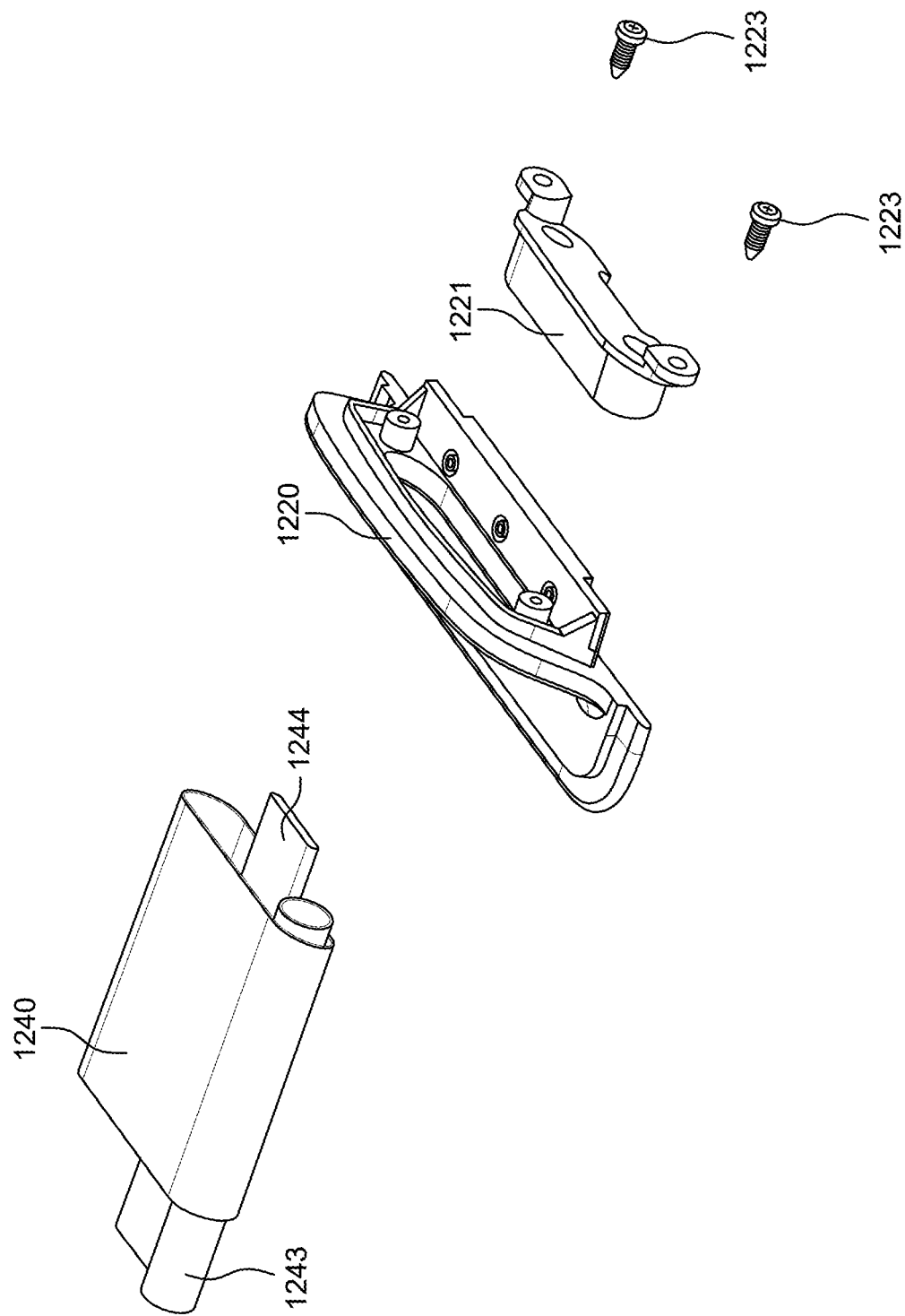

FIG. 12K shows an illustrative exploded view of faceplate 1220 and sleeve 1240. Faceplate 1220 may be secured to twisted string termination member 1221 via screws 1223. Twisted strings (not shown) may originate from one or more flexdrives and pass through through-holes in member 1221 and be threaded through string conduits 1243 and secured to anchor 1242. Also shown in FIG. 12K is data cable 1244 that passes inside sleeve 1240.

FIG. 12L shows an exploded view of anchor 1242. Anchor 1242 can include hook member 1241, bottom enclosure 1247a, top enclosure 1247b, PCB connector 1248, dowels 1246, conduit 1246, string conduits 1243, and sleeve 1240. A twisted string (not shown) may pass through each string conduit 1243 and through a through-hole in conduit 1245 and be attached to hook member 1241 via dowels 1246. Conduit 1245 may be secured to hook member 1241 via screws 1249. Data cable 1244 may be secured to PCB connector 1248, which can also be secured to hook member 1241. Bottom and top enclosures 1247a and 1247b serve as a cover for anchor 1242.

Sleeve 1240 may be secured to termination member 1221 and conduit 1245. Sleeve 1240 may be constructed from a material that can collapse onto itself when the twisted string is activated by a flexdrive. For example, in some embodiments, the material may be fabric. String conduits 1243 and data cable 1244 may be secured to sleeve 1240.

Figures 13A, 13B, 13C:
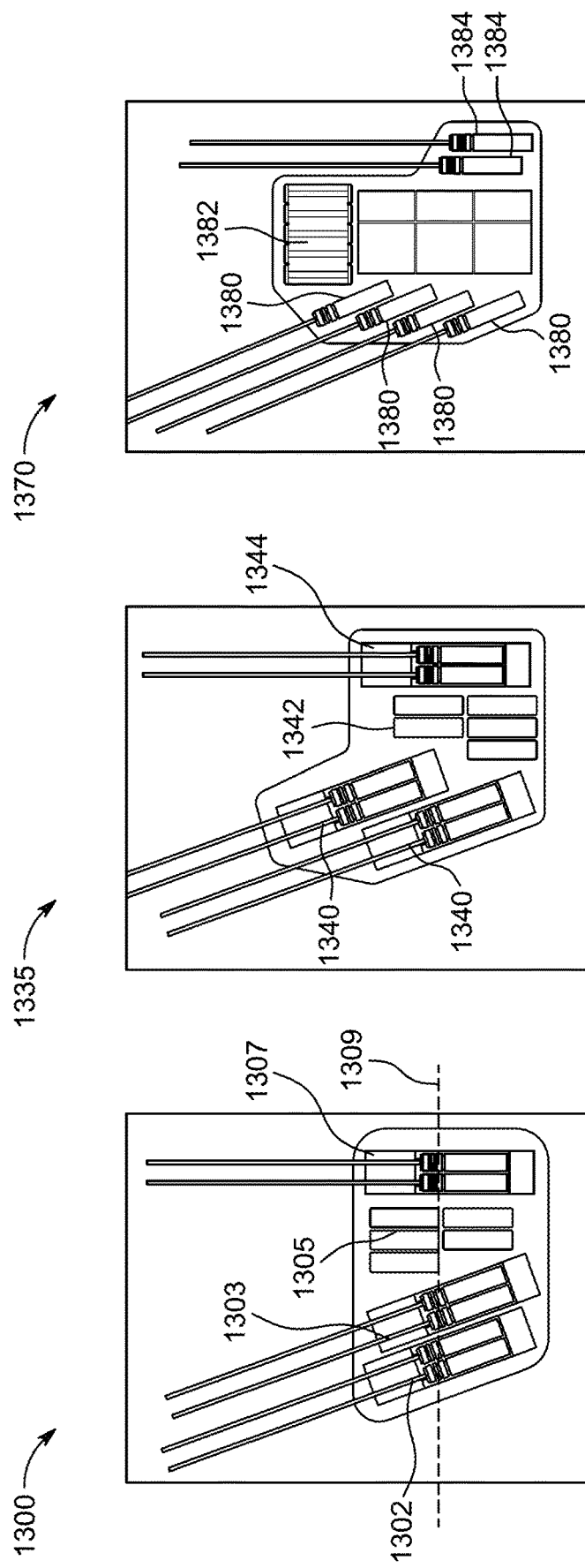
FIGS. 13A-13C show schematic views of different leg patch assemblies according to various embodiments.

FIGS. 13A-13C show schematic views of leg patch assemblies 1300, 1335, and 1370 according to various embodiments. Each of leg patch assemblies 1300, 1335, and 1370 has their respective flexdrives and batteries arranged in different configurations. Leg patch assembly 1300 of FIG. 13A has a horizontally biased configuration in that extensor flexdrives 1302 and 1303, batteries 1305, and flexor flexdrives 1307 are aligned with respect to horizontal axis 1309.

Leg patch assembly 1335 has a vertically biased configuration in that extensor flexdrives 1340 are positioned vertically with respect to batteries 1342 and flexor flexdrive 1344. Leg patch assembly 1370 has a vertically biased configuration in that extensor flexdrives 1380 are positioned vertically with respect to batteries 1382 and flexor flexdrive 1384.

Figure 14C:
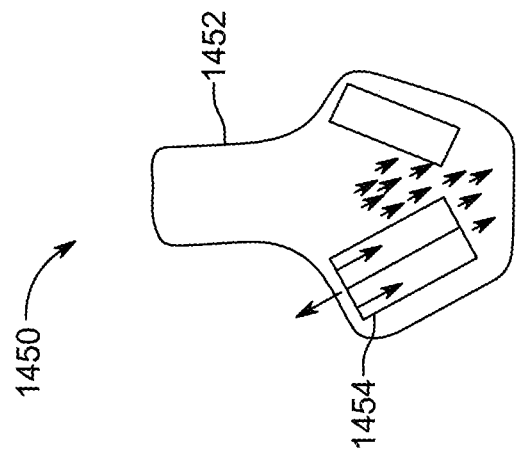
FIGS. 14A-14C show different force loading diagrams for various leg patch assemblies.
Figure 14B:
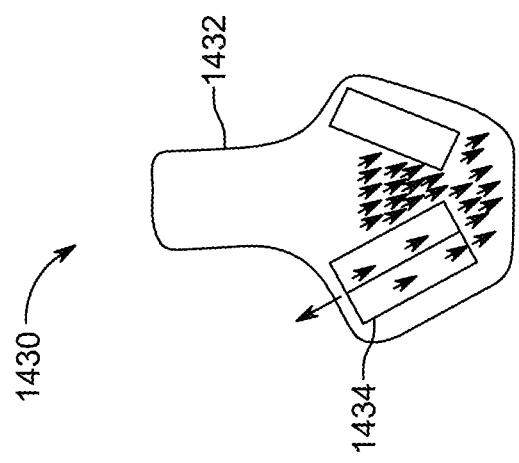
Figure 14A:
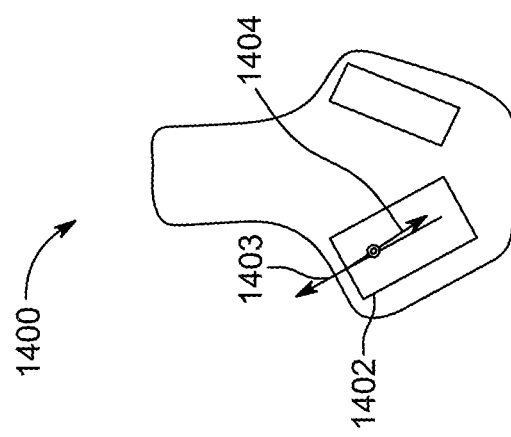

FIGS. 14A-14C show different force loading diagrams for various leg patch assemblies. In each of the force loading diagrams, the leg patch assembly applies a counteractive force to the force applied by one or more of the flexdrives. The leg patch assemblies can be designed and constructed to tune the degree of counteractive force applied by the leg patch. FIG. 14A shows leg patch assembly 1400 in which load is transmitted directly from flexdrive enclosure 1402 into a load distribution member (not shown). In this configuration, force applied by the flexdrive (shown by arrow 1403) is opposed only by flexdrive enclosure 1402. The opposing force is shown by arrow 1404. Leg patch assembly 1400 may provide predictable and quantifiable loading. The patch construction may include hardgood/softgood transitions that do not require structural leading. Leg patch assembly 1400 may require that the load distribution member include stiffener to assist in transmitting force across a larger than that which can be provide by flexdrive enclosure 1402.

FIG. 14B shows leg patch assembly 1430 in which load is transmitted in to base layer 1432 when flexdrive 1434 is activated. The load transmission force is shown by the small arrows pointing downwards and to the right. The flexdrive force is shown by the large arrow pointing upwards and to the left. In this embodiment, the entirety of base layer 1432 is distributing force across a load distribution member (not shown). This embodiment further enables flexibility in adjusting the angle of flexdrive 1434 of orientation with respect to base layer 1432. In addition, this embodiment may be used in conjunction with a load distribution member that does not require a stiffener.

FIG. 14C shows leg patch assembly 1450 in which load is transmitted in to base layer 1452 and flexdrive enclosure 1454 when the flexdrive is activated. In this embodiment, both base layer 1452 and flexdrive 1454 transmit the load exerted by the flexdrive. Base layer loads are shown by the small arrows pointed in the downwards direction. Flexdrive enclosure loads are shown by the large arrows pointed in the downwards direction. This embodiment represents a hybrid of patch assemblies 1400 and 1430 and thus benefits from the advantages provided by the other patch assemblies.

Figure 15A:
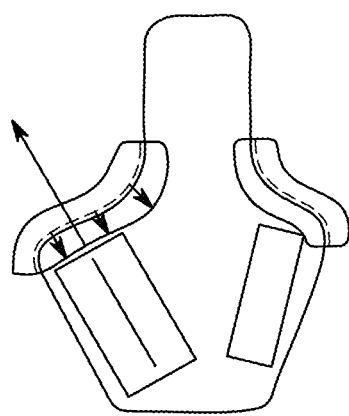
FIGS. 15A-15H shows different load distributions for a leg patch assembly according to various embodiments.
Figure 15B:
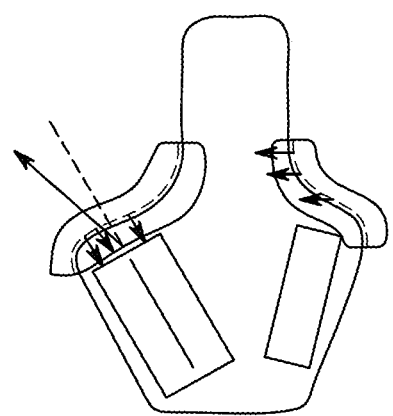
Figure 15C:
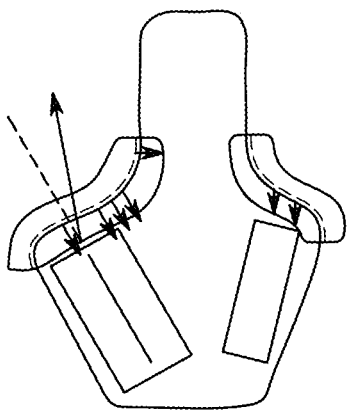
Figure 15D:
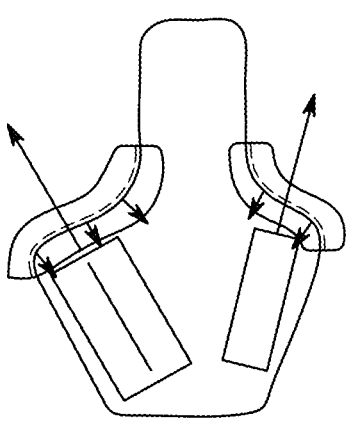

FIGS. 15A-15H shows different load distributions for a leg patch assembly according to various embodiments. Each FIG shows the force applied by the flexdrives and counteractive (or reactive) force applied by the patch. The FIGS shows different force angles for both flexdrive force and patch counteractive force. FIGS. 15A-15D show illustrative leading edge counteractive forces. In FIG. 15A, for example, the flexdrive force is parallel to the orientation of the flexdrive and the counteractive forces directly oppose that flexdrive force. In FIG. 15B, for example, the flexdrive force is directed at an angle (e.g., left of center) that is not parallel to the orientation of the flexdrive. As a result, the counteractive forces are shown to being exerted on both sides of the patch, thereby creating a moment. In FIG. 15C, the flexdrive force is directed at an angle (e.g., right of center) that is not parallel to the orientation of the flexdrive. The counteractive forces are shown to being exerted on both sides of the patch. In FIG. 15D, flexdrive forces for both flexdrives are parallel to their respective flexdrive orientation. The counteractive forces are shown to being exerted on both sides of the patch.

Figure 15E:
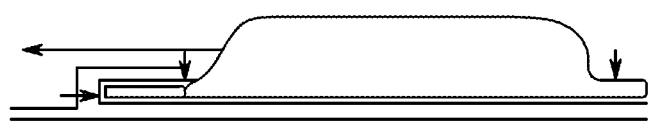
Figure 15F:
Figure 15G:
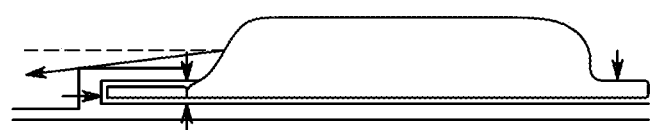
Figure 15H:
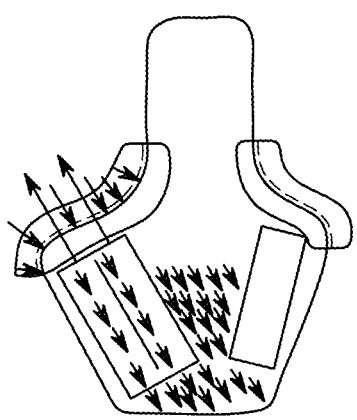

FIGS. 15E-15G illustrate examples of counteractive loads at the bottom or rear of the patch. The flexdrive forces and counteractive forces are self-explanatory. FIG. 15H shows a dual flexdrive forces being applied in parallel with the orientation of the flexdrives. In addition, FIG. 15H shows counteractive forces being applied by the leading edge and face of the patch.

Figure 16A:
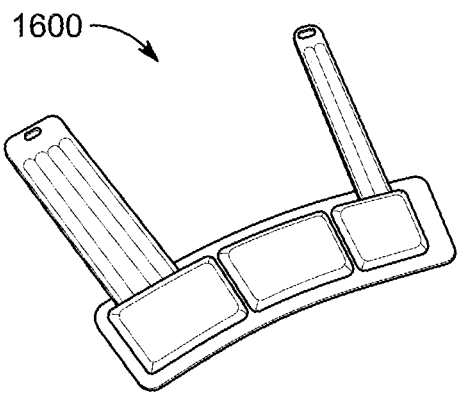
FIGS. 16A-16C show a leg patch assembly according to an embodiment.
Figure 16B:
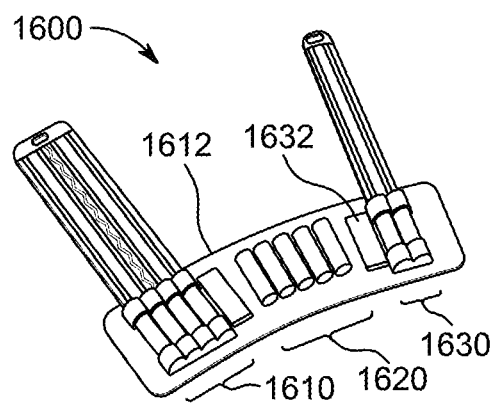
Figure 16C:
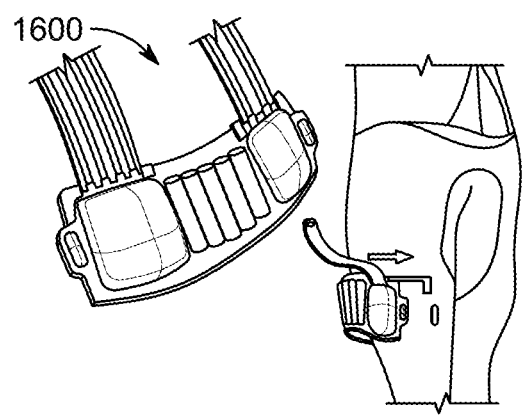

FIGS. 16A-16C show leg patch assembly 1600 according to an embodiment. Leg patch assembly 1600 can include flex drive group 1610, PCB 1612, batteries 1620, flexdrive group 1630, and PCB 1632. PCB 1612 may contain electronics needed to operate flex drive group 1610, and PCB 1632 may contain electronics needed to operate flex drive group 1630.

Figure 17:
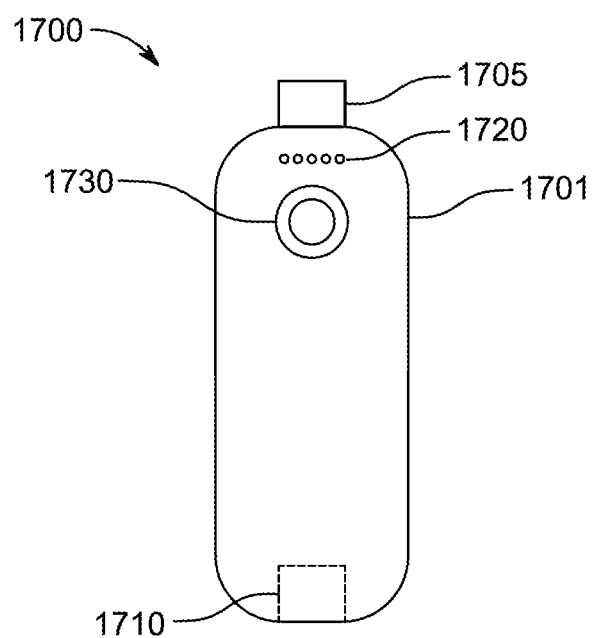
FIG. 17 shows an illustrative battery pack according to various embodiments.

FIG. 17 shows illustrative battery pack 1700 according to various embodiments. Battery pack 1700 may include housing 1701, pull tab 1705, connector 1710, LEDs 1720, and button 1730. Battery pack 1700 may also include electronics, sensors, and vibrator mechanism. Battery pack 1700 is designed to be inserted in and removed from the exosuit (e.g., a leg patch assembly). A user may pull on pull tab 1705 to remove battery pack 1700. Battery pack 1700 may be constructed in a variety of different shapes and sizes, but in general, it may be designed to maintain a relatively slim profile that does not protrude too far away from the body of the wearer. Connector 1710 may connect to a charger to charge the battery(ies) contained therein, and to interface with an electrical connection on the exosuit. LEDs 1720 may provide feedback as visual confirmation as to the charge status of battery pack 1700 and to provide other status indicators. The other status indicators can include, for example, an error indicator, a busy indicator, and a ready indicator. The user may press button 1730 to obtain feedback.

Battery pack 1700 may provide feedback to the user by activating a vibration unit (not shown). Battery pack 1700 may vibrate to communicate information to the user without requiring the user to visually access the battery. In addition, battery pack 1700 may be used to provide feedback in lieu of other exosuit feedback mechanisms (e.g., flexdrives, speakers, other LEDs). For example, the vibration mechanism may be used to indicate which region of the exosuit is performing assistive movements.

Figure 18:
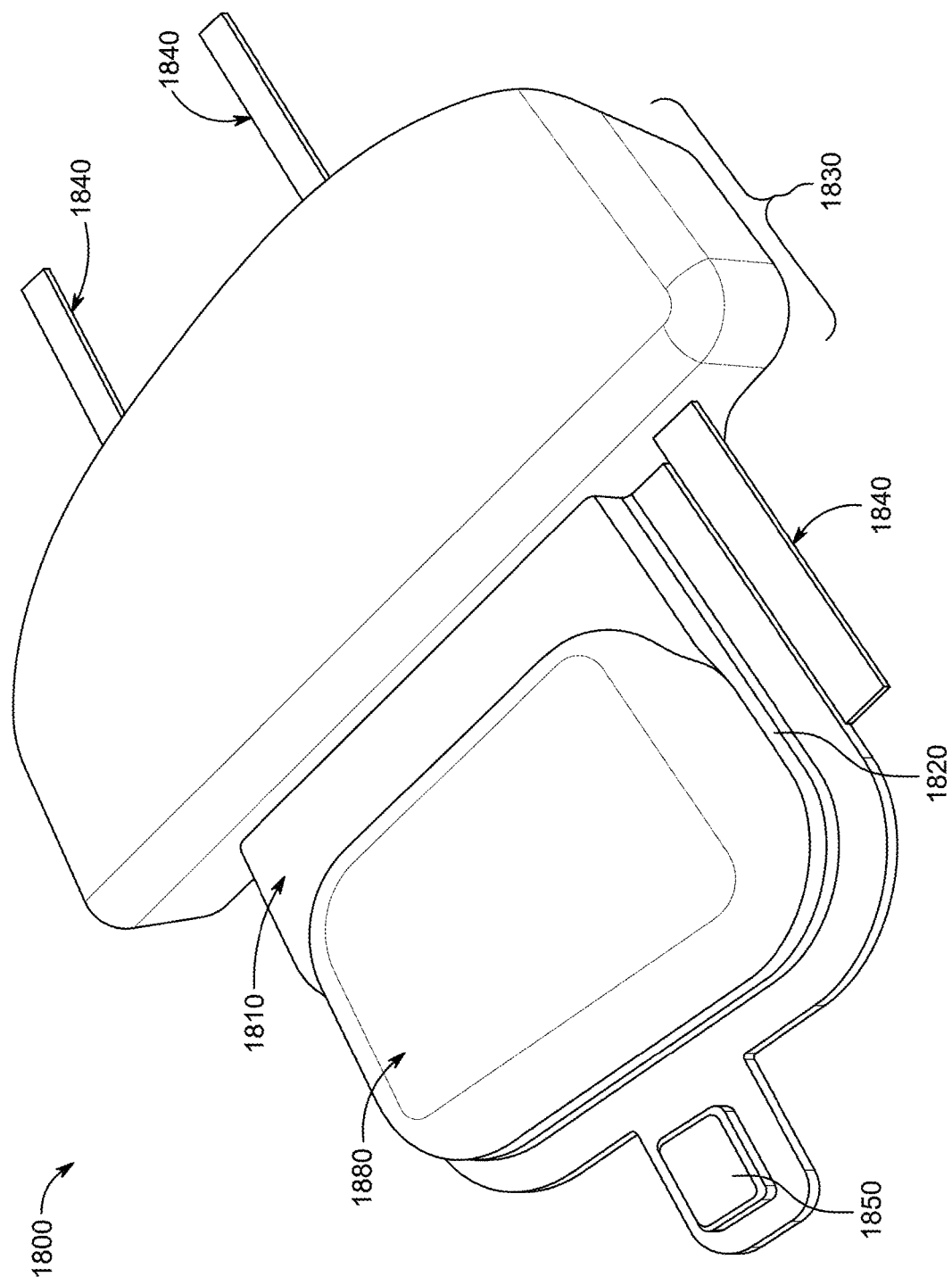
FIG. 18 shows an illustrative view of a core patch assembly according to an embodiment.

FIG. 18 shows an illustrative view of core patch assembly 1800 according to an embodiment. Core patch assembly 1800 may be a power layer segment that can be secured to a load distribution member associated with a back of a user. Core patch assembly 1800 may serve as a communications/processing center of the exosuit. Assembly 1800 may include housing 1810, battery portion 1820, electronics portion 1830, cables 1840, IMU portion 1850, and battery pack 1880. Housing 1810 may include anchors (not shown) that secure assembly 1800 to the load distribution member. Battery pack 1880 may be retained in battery portion 1820. Electronics portion 1830 may contain electronics such as a processor, communications circuitry, and power management circuitry to control operation of the exosuit.

FIGS. 19A-19B show different flexdrive modules according to various embodiments. FIG. 19A shows single motor flexdrive module 1900 and FIG. 19 shows dual motor flexdrive module 1950. Both FIGS. 19A and 19B show plan and top views of modules 1900 and 1950. Referring now specifically to FIG. 19A, module 1900 can include housing 1902, motor 1904, printed circuit board (PCB) 1906, brake motor 1908, brake mechanism 1910, sensor/string coupler 1912, encoder 1914. Referring now to FIG. 19B, module 1950 may include housing 1952, motors 1953 and 1954, printed circuit board (PCB) 1956, brake motor 1958, brake mechanism 1960, sensor/string couplers 1961 and 1962, and encoders 1963 and 1964. The arrangements of the components within modules 1900 and 1950 can be rearranged to accommodate different footprint sizing. By combining two motors into a single package (as shown in module 1950), space savings can be realized by having the two motors share components.

Figure 20A:
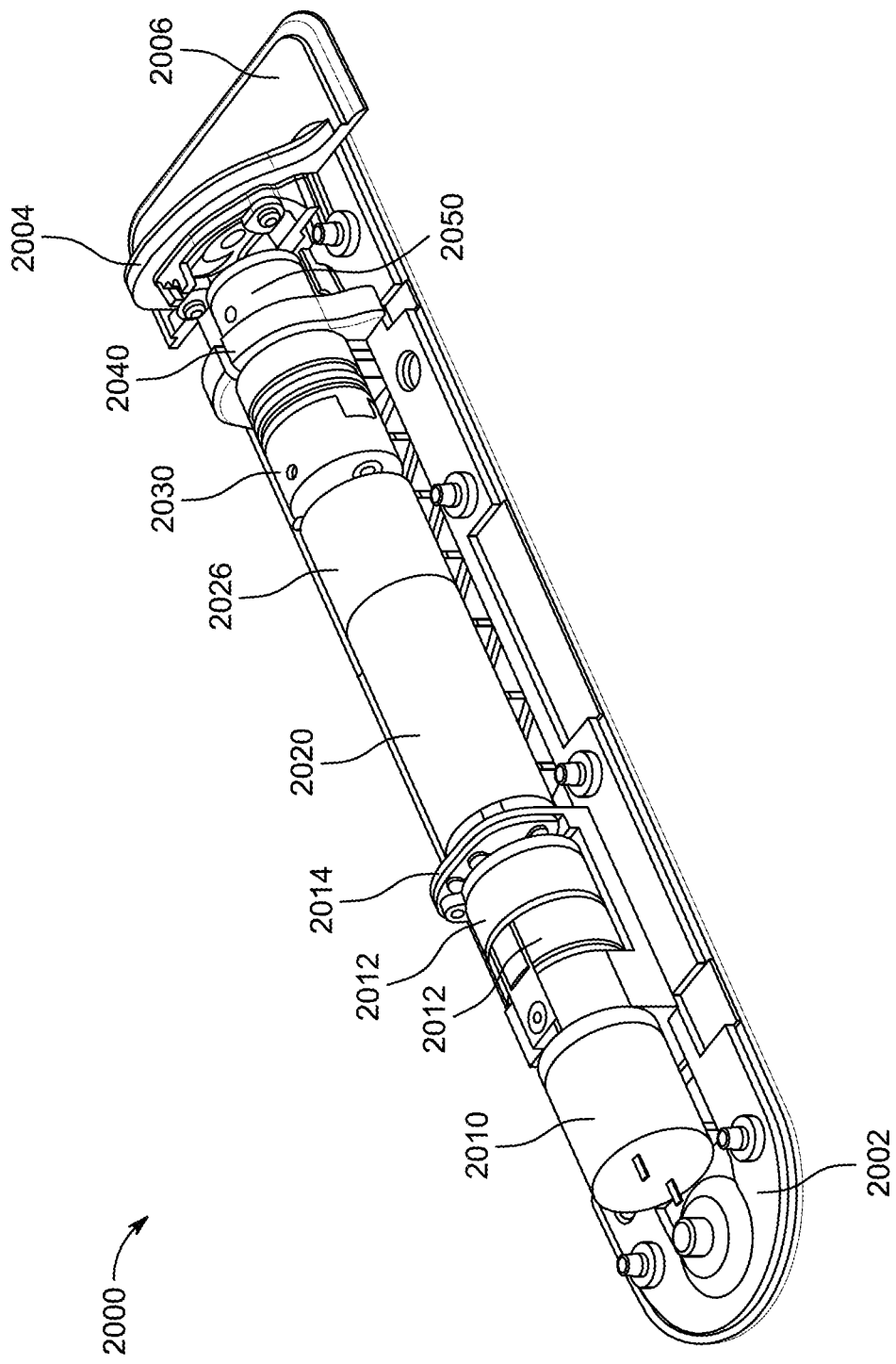
FIG. 20A shows a flexdrive module according to an embodiment.

FIG. 20A shows flexdrive module 2000 according to an embodiment. FIGS. 20B-20J shows different views of module 2000 or portions thereof. The following discussion will collectively reference FIGS. 20A-20J. Flexdrive module 2000 may be incorporated into a leg patch assembly as discussed above, and in particular, may be secured within a flexdrive enclosure. Module 2000 can include base 2002, faceplate 2004, patch interface 2006, lock motor 2010, lock mechanism 2012, encoder 2014, drive motor 2020, gearbox 2026, coupler 2030, sensor 2040, and string coupler 2050.

Figure 20B:
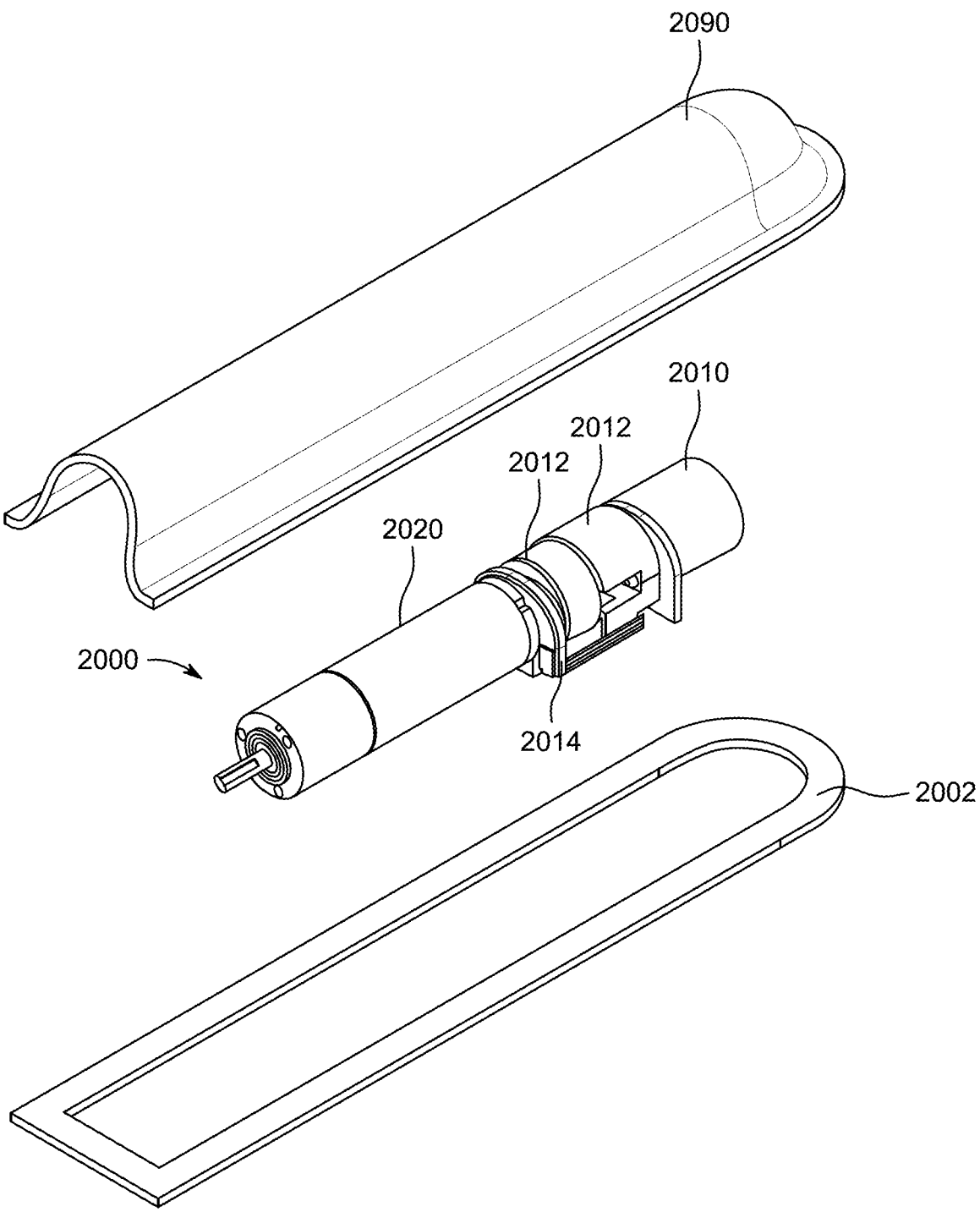
Figure 20E:
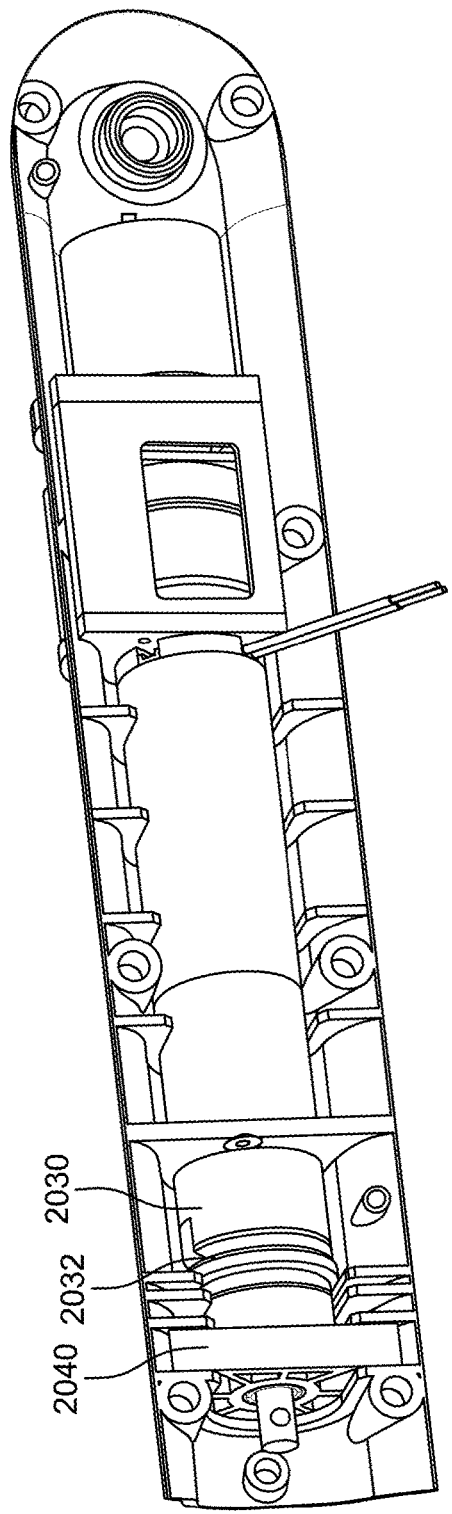
Figure 20F:
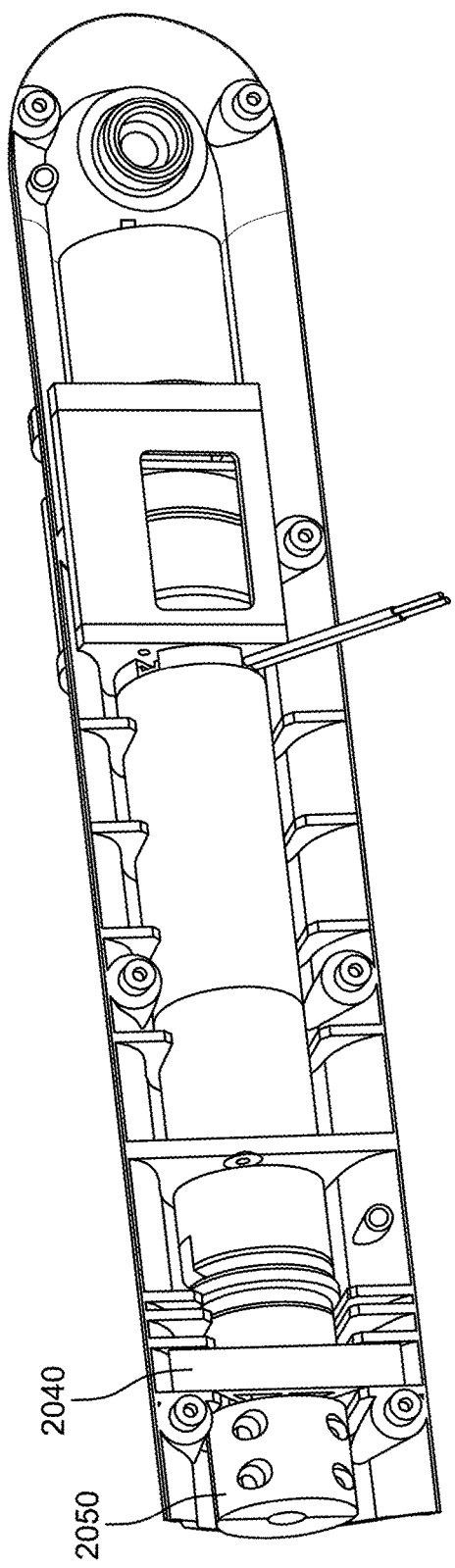

FIG. 20B shows base 2002, various components of module 2000 (such as lock motor 2010, lock mechanism 2012, encoder 2014, and drive motor 2020), and cover 2090. Cover 2090 may fit around the components of the flexdrive and be secured to base 2002. FIG. 20C shows flexdrive module 2000 with base 2002 removed. Cover 2090 can include ribs 2092 to support and register components of the flexdrive. FIG. 20D-20F also show flexdrive module 2000 in different stages of assembly. In particular, FIG. 20D shows addition of coupler 2030, FIG. 20E show addition coupler members 2032, sensor 2040, and FIG. 20F shows a string coupler 2050.

Figure 20G:
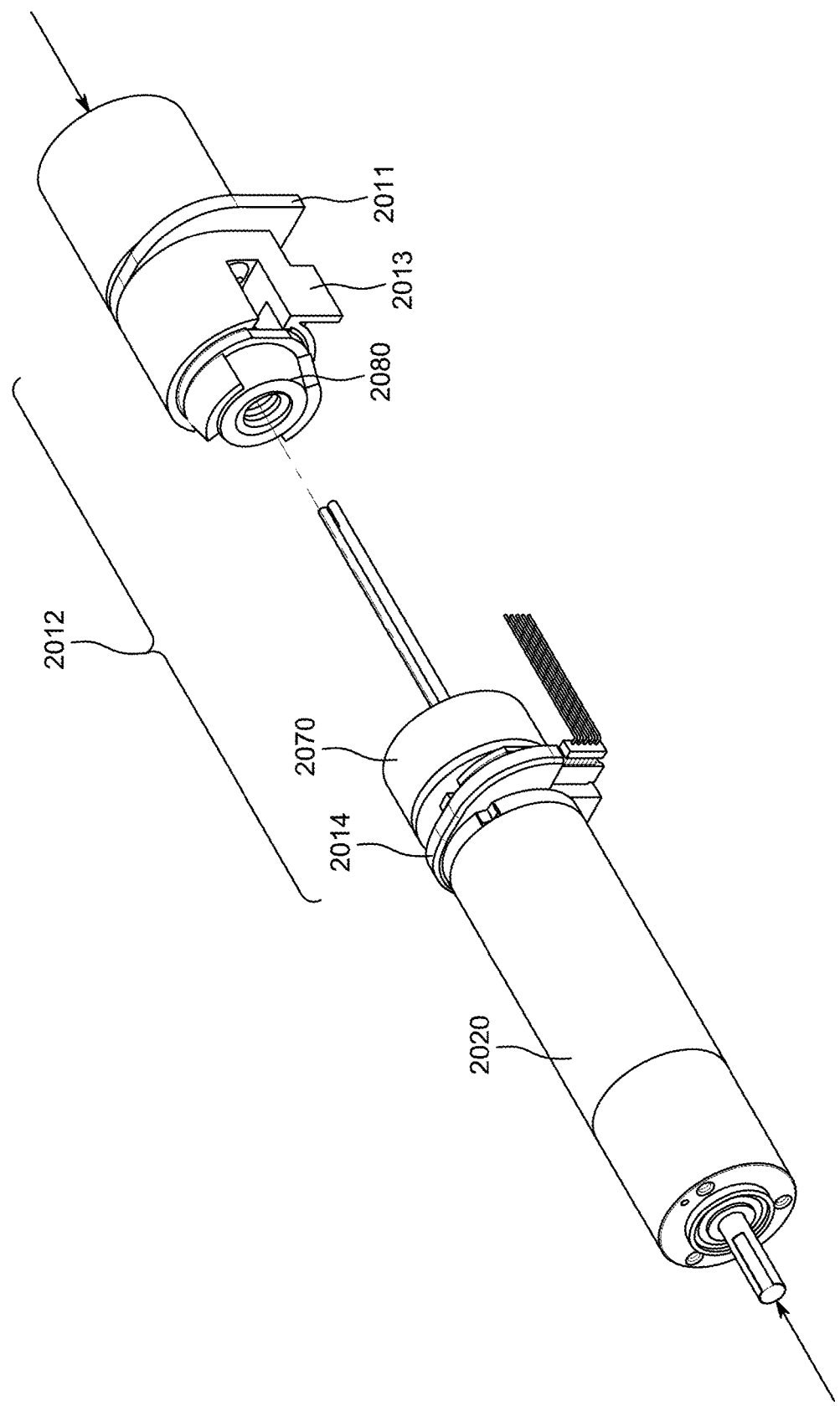

FIG. 20G shows a partial exploded view of a portion of flexdrive module 2000. In particular, FIG. 20G shows drive motor 2020 coupled to encoder 2014 and lock cone 2070 of lock mechanism 2012. FIG. 20G also shows lock motor 2010 coupled to locking plate 2011, which is coupled to block 2013. Nut 2072 (which is part of may be connected to locking motor 2011 via locking screw 2081 (shown in FIG. 20I).

Figure 20H:
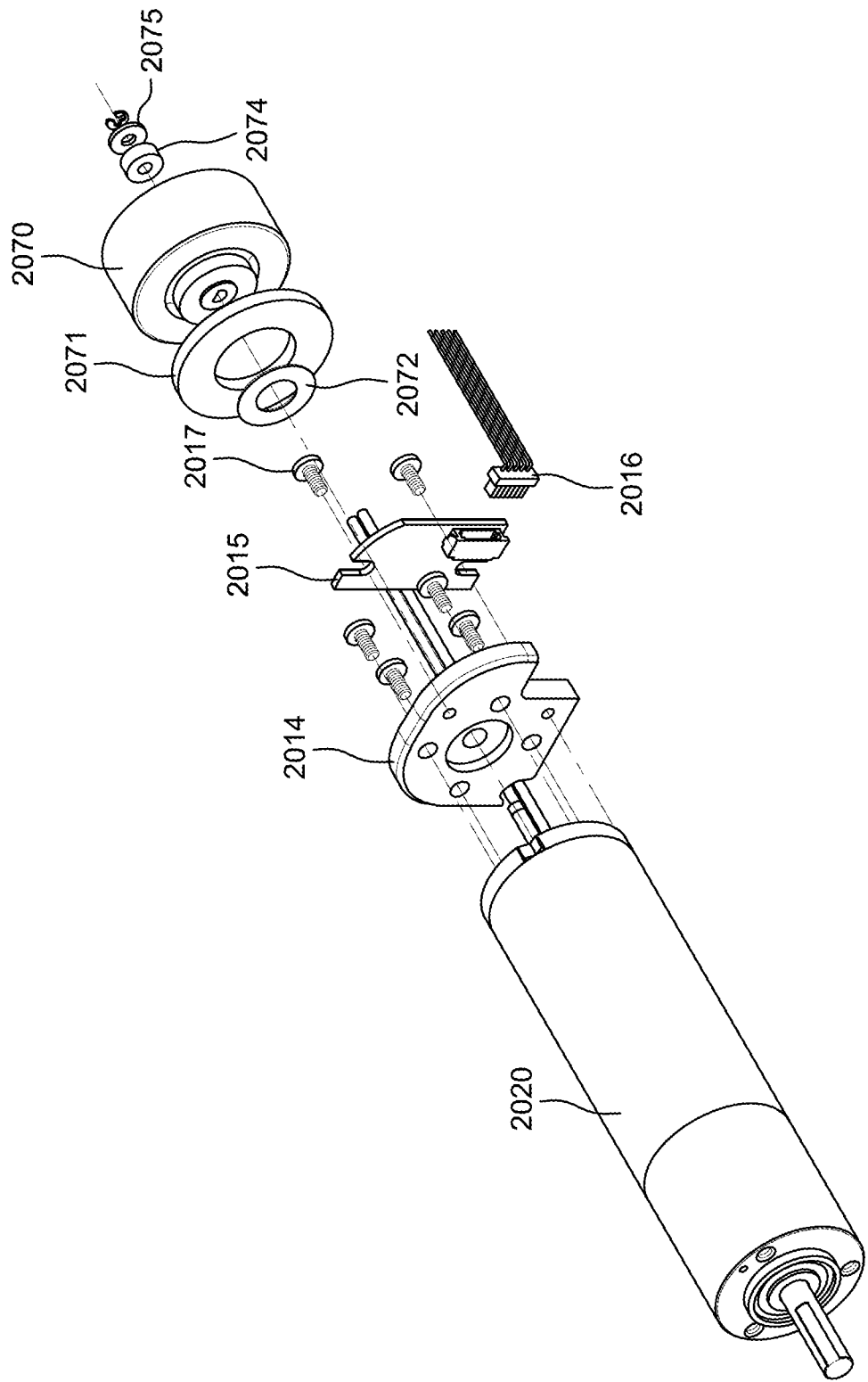

FIG. 20H shows an illustrative exploded view of drive motor 2020, encoder 2014, and lock cone 2070. The exploded view shows encoder PCB 2015, encoder power/data wires 2016, fasteners 2017 that couple PCB 2015 and encoder 2014 to drive motor 2020. Also shown in FIG. 20H is washer 2072, encoder magnet 2071, female lock cone 2070, retaining washer 2074, and retaining ring 2075. A shaft (not shown) extends from drive motor and passes through encoder 2014, washer, encoder magnet 2071, female lock cone 2070, retaining washer 2074, and is capped with retaining ring 2075. Lock cone 2070 may turn in concert with the drive shaft of drive motor 2020. Thus, when female lock cone 2070 is locked in place, the drive shaft of drive motor 2020 may not be permitted to rotate.

Figure 20I:
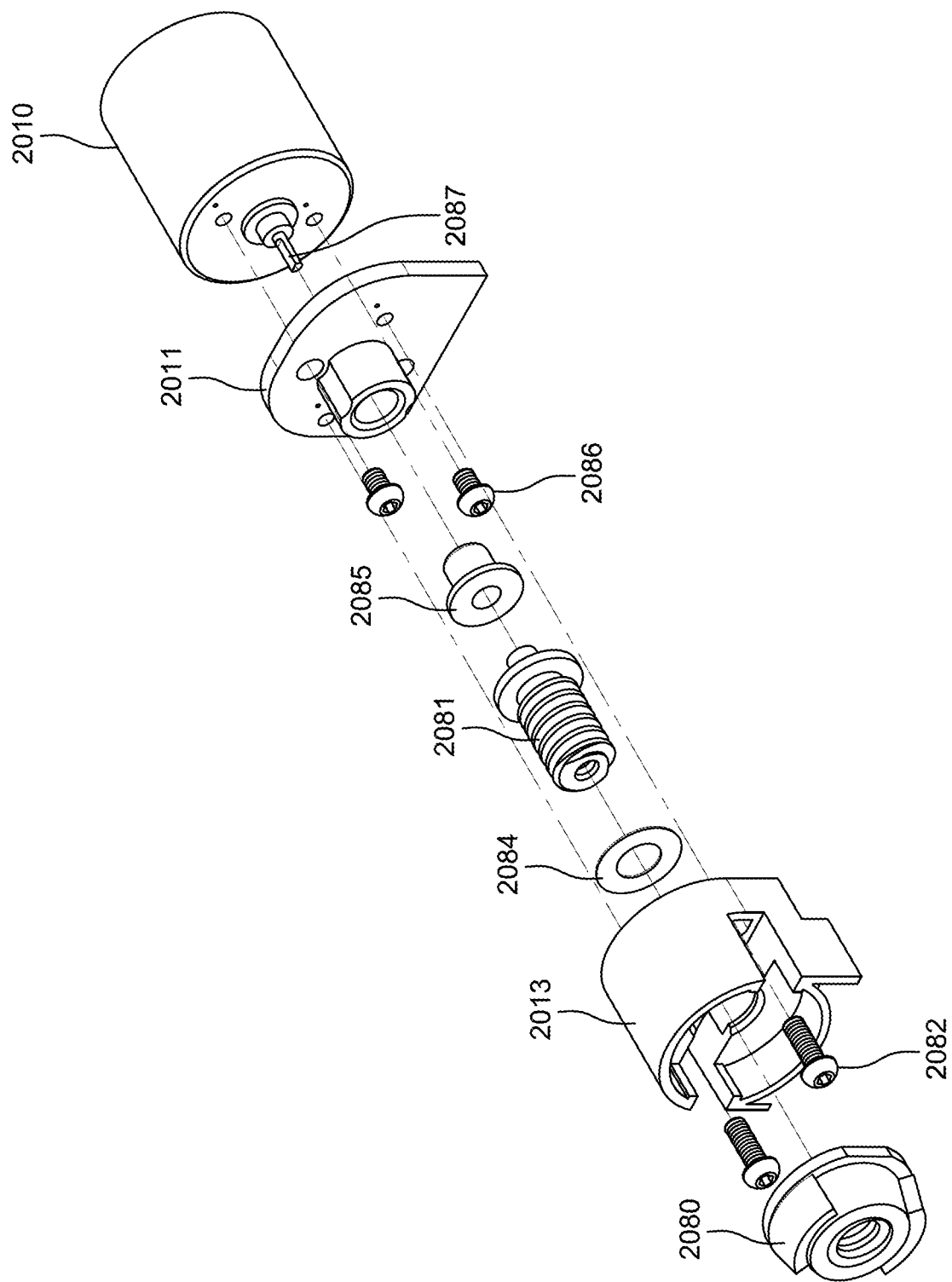

FIG. 20I shows an illustrative exploded view of lock motor 2010, locking plate 2011, block 2013, nut 2072, locking screw 2081, among other components. Fasteners 2086 secure locking plate 2011 to lock motor 2010. Lock motor shaft 2087 pass through bushing 2085 is secured to locking screw 2081. Locking screw 2081 may pass through washer 2084 and block 2013 and is secured to male lock cone 2080. Fasteners 2082 may secure block 2013 to locking plate 2011. When lock motor 2010 rotates in a locking direction, locking screw 2081 rotates and causes male locking cone 2080 to be driven axially into female locking cone 2070. When male locking cone 2080 is sufficiently seated within female locking cone, the shaft of drive motor 2020 is not permitted to rotate. When lock motor 2010 rotates in an unlocking direction, locking screw 2081 rotates and causes male locking cone 2080 to be pulled out of female locking cone 2070, thereby enabling the shaft of drive motor 2020 to rotate.

Figure 20J:
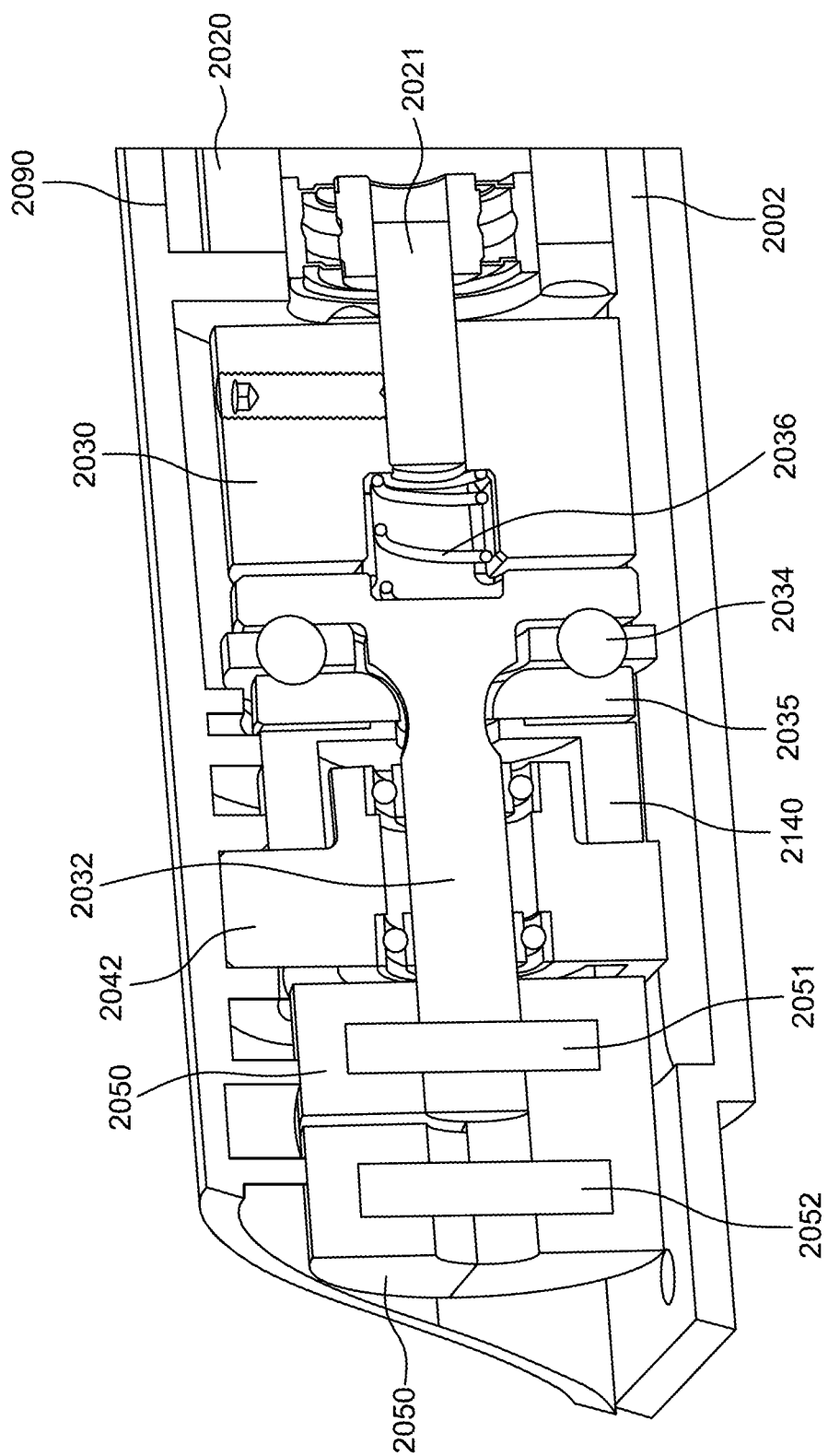

FIG. 20J shows an illustrative cross-sectional view base 2002, cover 2090, coupler 2030, sensor 2040, and string coupler 2050, among other features. String drive coupler member 2032 is shown connected to coupler 2030 and string coupler 2050, passing through bearings 2042, 2034 and 2035, and force sensor 2040. Compression spring 2036 may exist between coupler 2030 and coupler member 2032. Coupler 2030 is connected to drive shaft 2021 of driver motor 2020. Dowel 2051 may secure string coupler to coupler member 2032. Dowel 2052 may be secured to a twisted string (not shown).

FIG. 20K shows illustrative exploded view of string drive coupler member 2032, string coupler 2050, and dowel 2051.

Figure 21A:
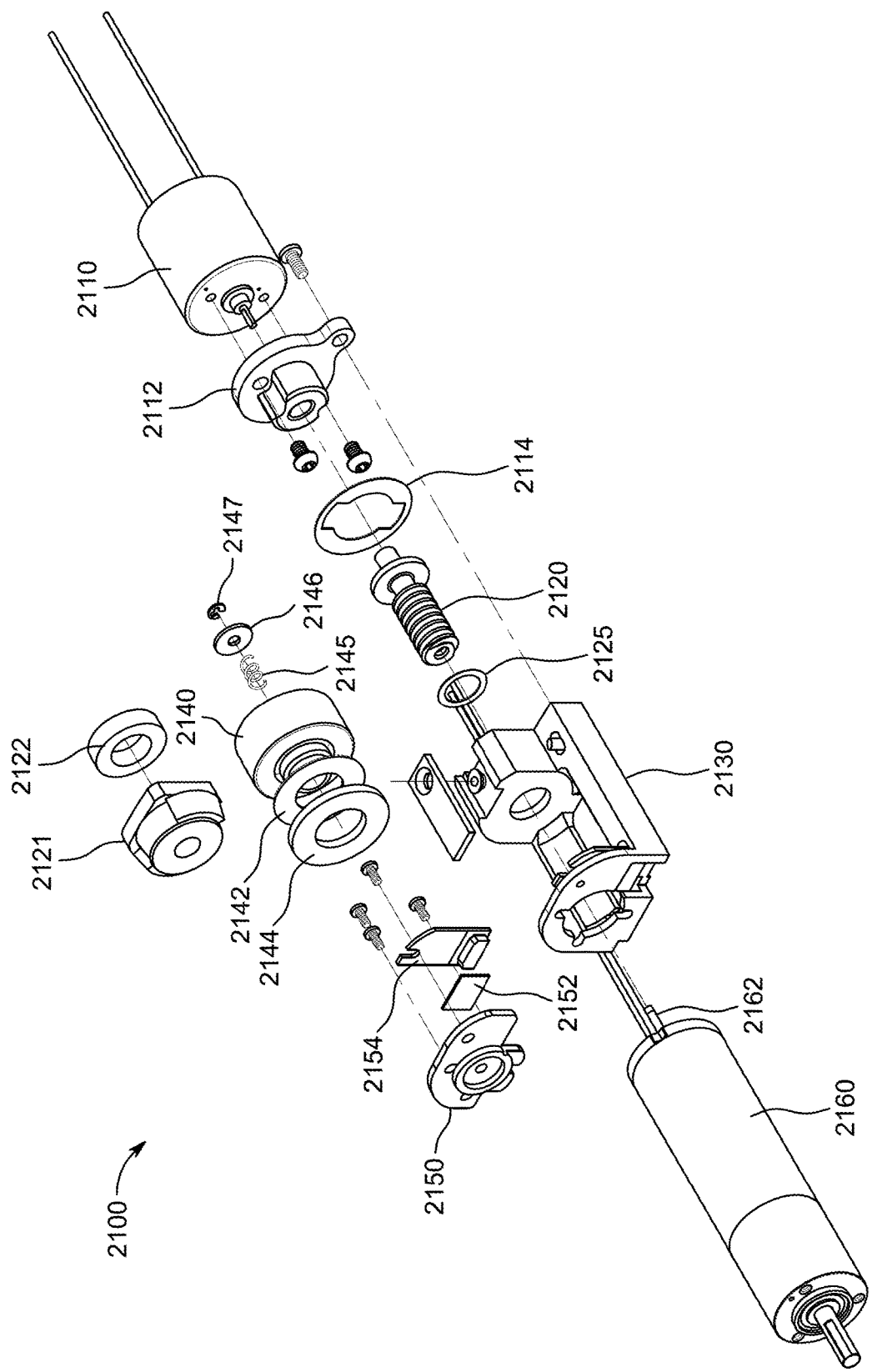
FIG. 21A shows an illustrative exploded view of a flexdrive module according to an embodiment.
Figure 21B:
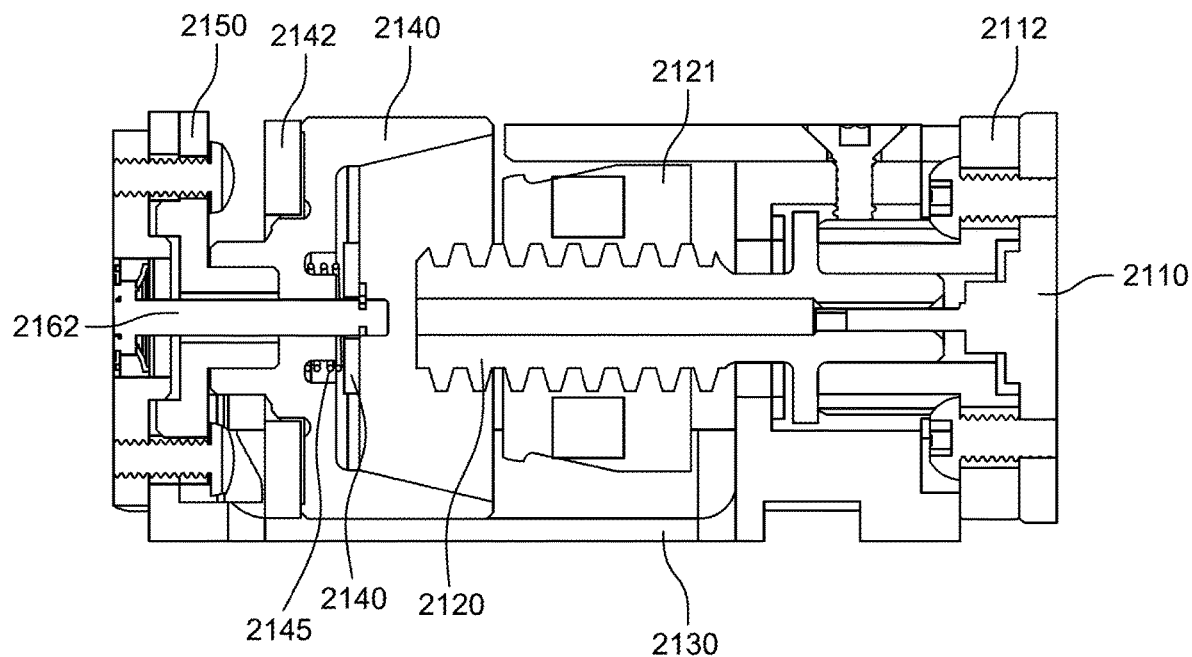
FIG. 21B shows an illustrative cross-sectional view of a flexdrive module according to an embodiment.
Figure 21C:
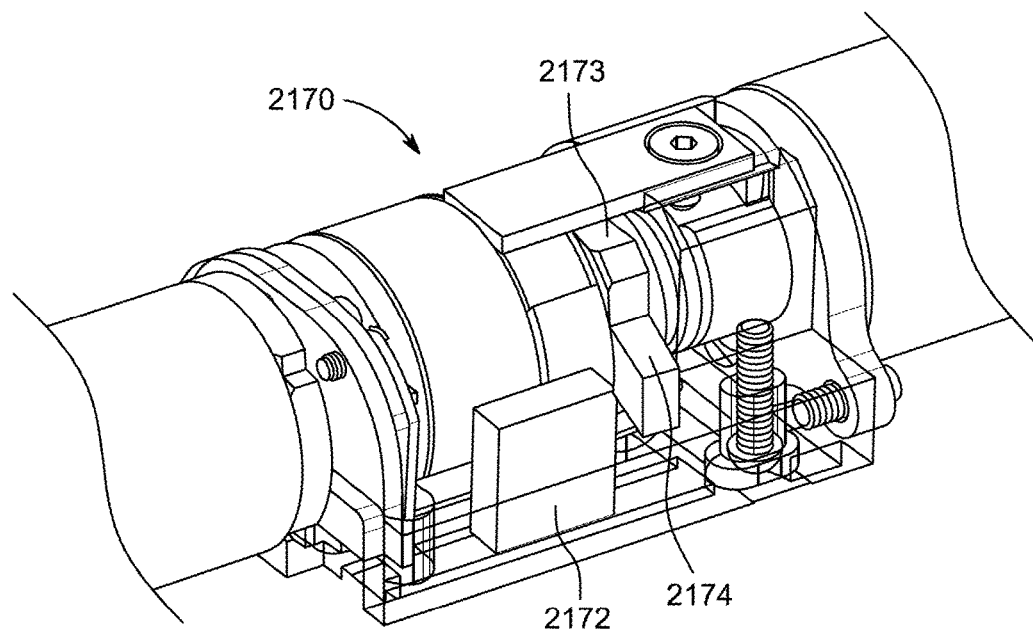
Figure 21D:
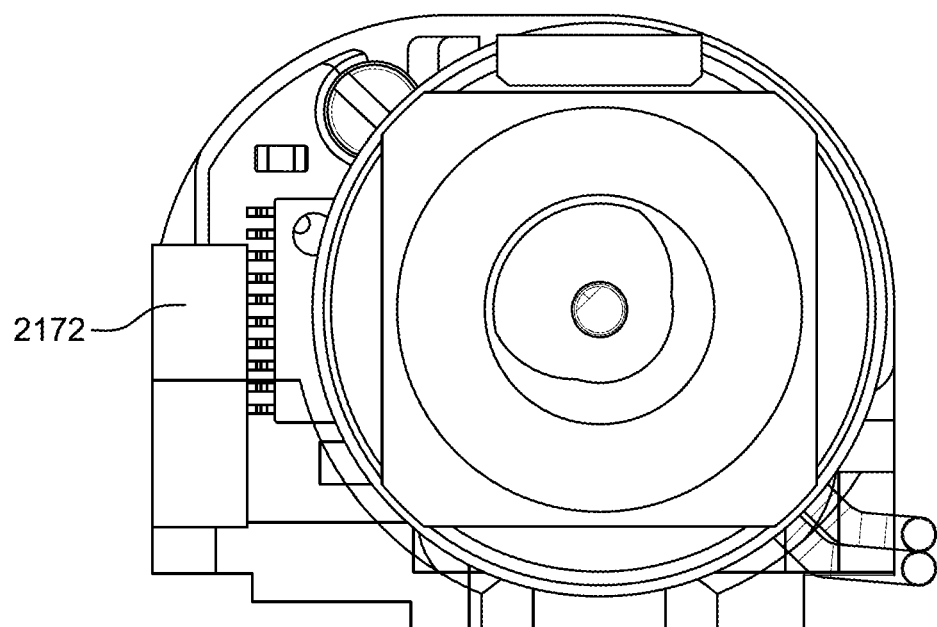
Figure 21E:
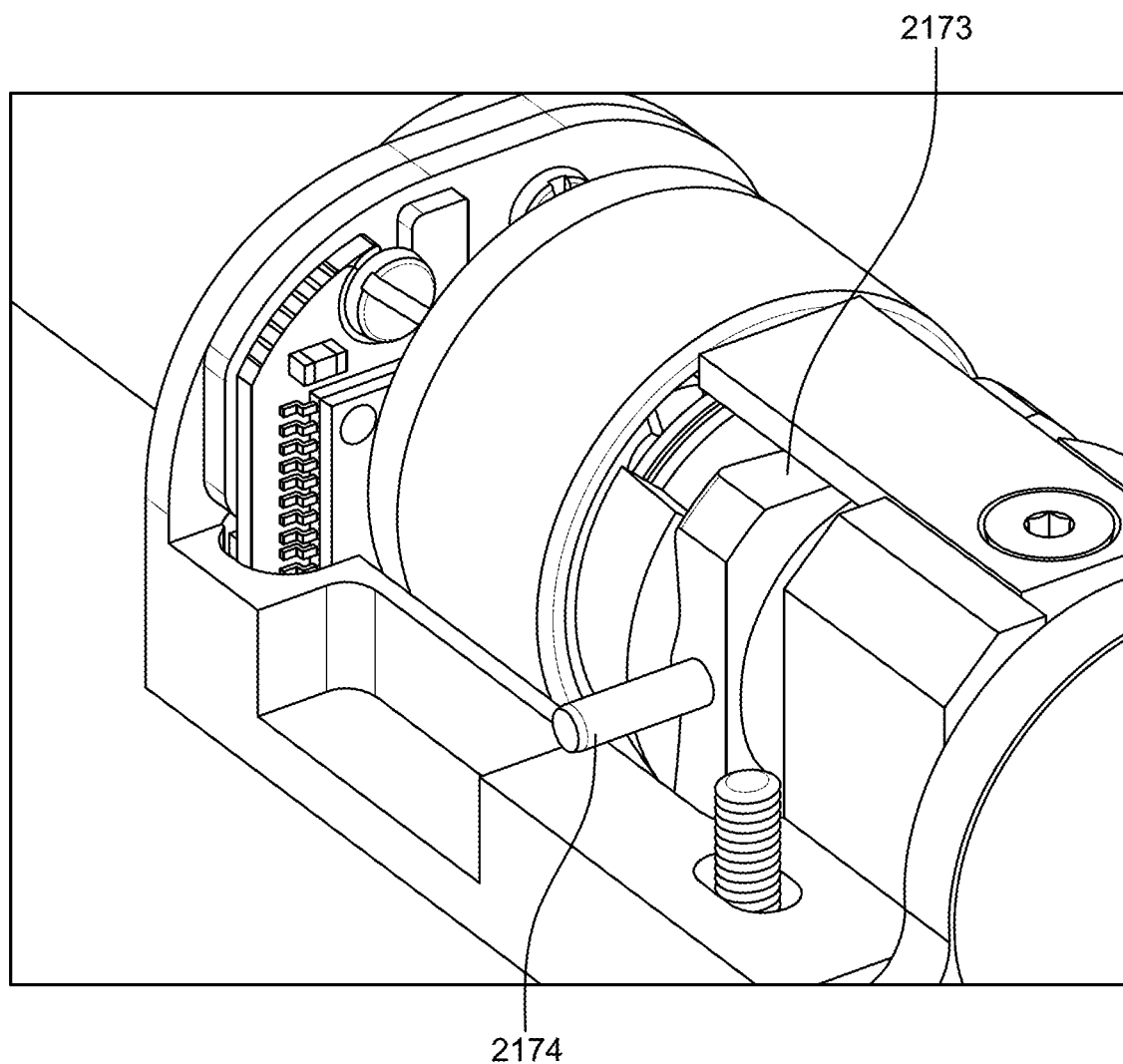
Figure 21G:
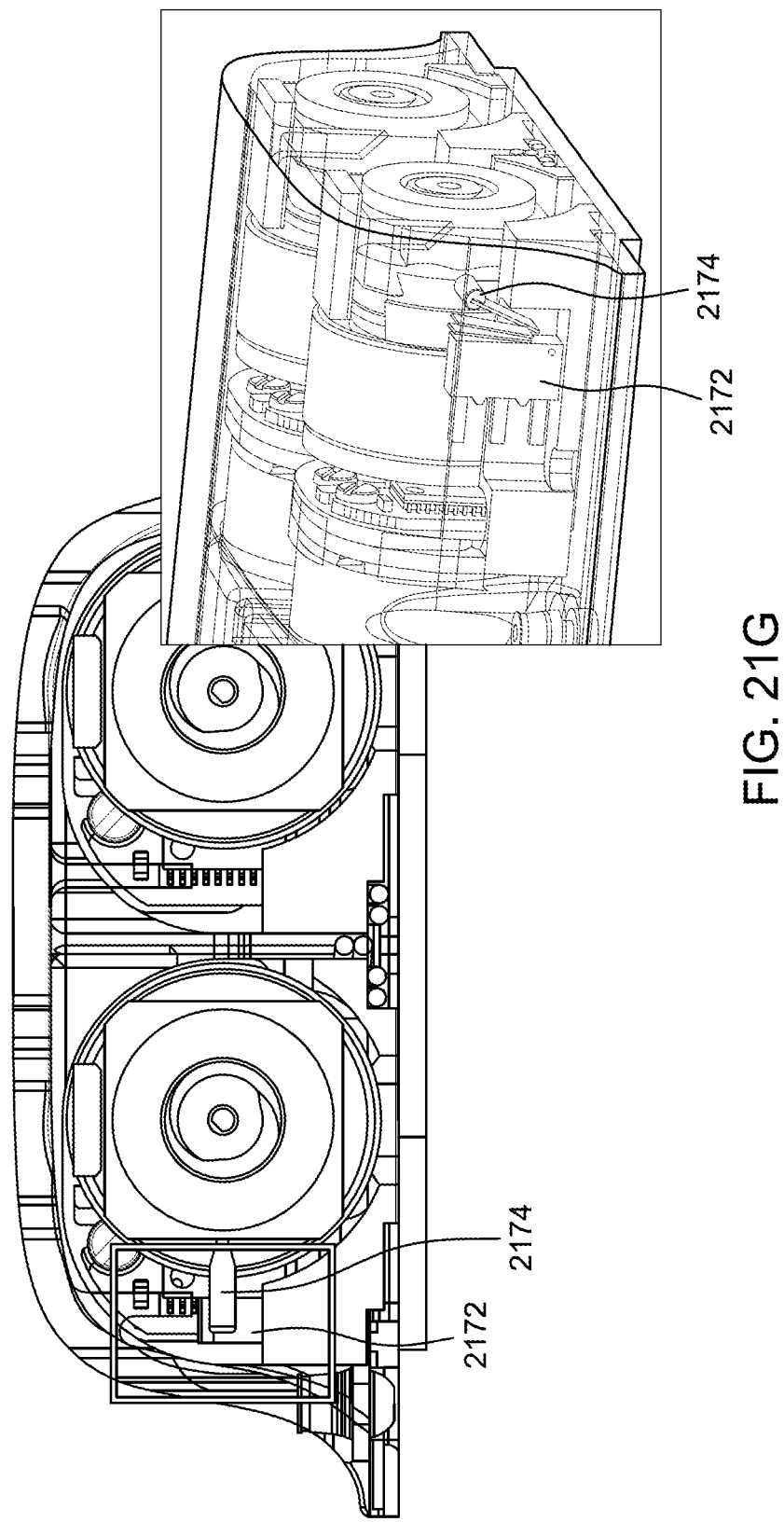
Figure 21H:
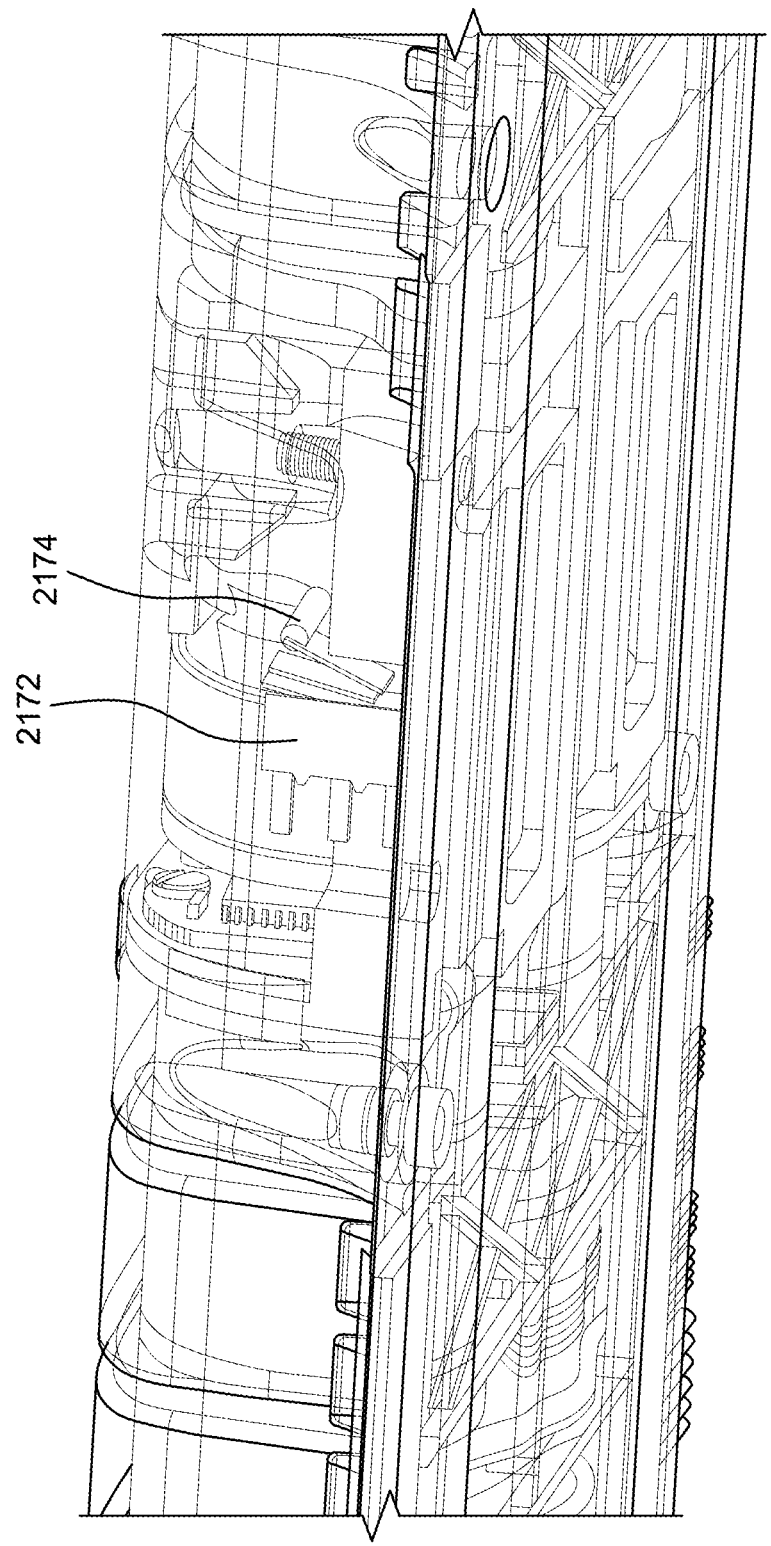

FIG. 21A shows an illustrative exploded view of flexdrive module 2100 according to an embodiment. FIG. 21B shows an illustrative cross-sectional view of flexdrive module 2100. Flexdrive module 2100 is similar to flexdrive 2000, but has additions to and a few modifications to various components. Flexdrive 2100 can include lock motor 2110, lock motor mount 2112, lock mount adhesive 2114, lock lead screw 2120, washer 2125, lead screw nut 2121, and foam pad 2122. Lock motor 2110 may be coupled to motor mount 2112, and lead screw 2120 may be coupled to lock motor 2010 via motor mount 2112. Lead screw may pass through washer 2125, through-hole 2132 of chassis 2130, and foam pad 2122 to be secured to lead screw nut 2121. Adhesive 2114 may be positioned between lock motor mount 2112 and chassis 2130. Lock motor mount 2112 may be coupled to chassis 2130 via one or more screws, for example. Shaft 2162 of drive motor 2160 passes through encoder 2150 and encoder magnet 2144 and is connected to lock cone 2140 via compression spring 2145, retaining washer 2146 and retaining ring 2147. PCB 2154 may be coupled to encoder 2150 via adhesive 2152 and one or more fasteners such as screws. Encoder 2150, lock cone 2140, lead screw nut 2121 may all be contained within chassis 2130.

Figure 21I:
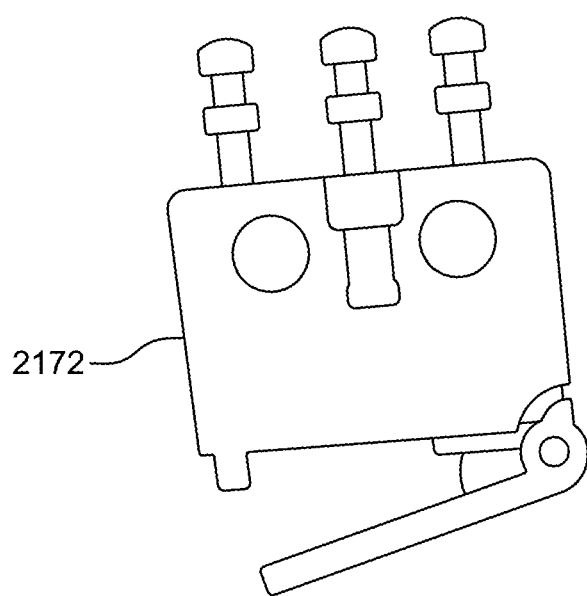
Figure 22:
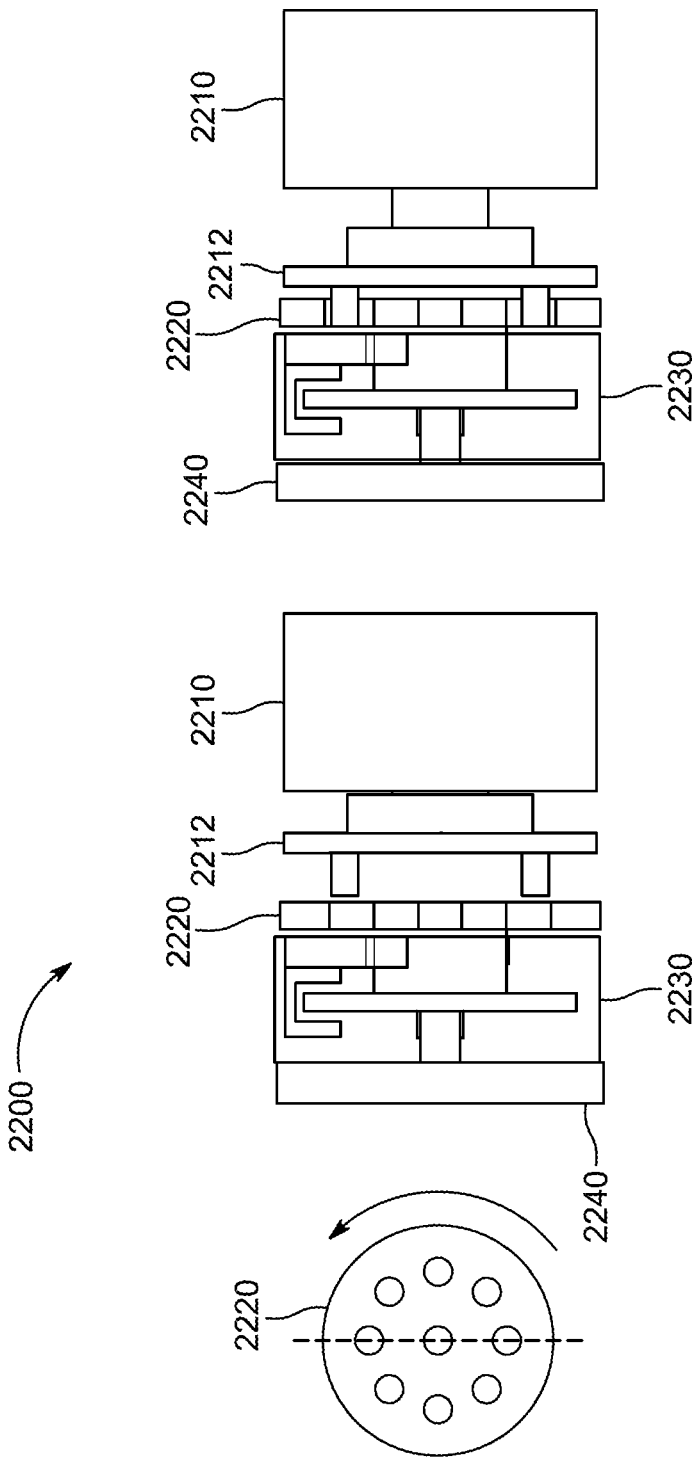
FIG. 22 shows a solenoid mechanical interlock assembly according to an embodiment.

FIGS. 21C-21J show views of an alternative flexdrive module 2170 according to an embodiment that includes switch 2172 and lead screw nut 2173. Lead screw lock 2173 replaces lead screw nut 2121 and has arm/pin 2174 that interfaces with switch 2172 depending on whether flexdrive module 2170 is locked or unlocked. In the arm embodiment, a protrusion may be injected molded as part of lead screw lock 2173. In the pin embodiment, a pin may be secured to lead screw lock 2173, and FIG. 21J shows illustrative views of lead screw lock 2173 capable of accepting the pin. Switch 2172, an illustrative detailed view of which is shown in FIG. 21I, is positioned within housing of flexdrive module 2170 and is operative to be closed when flexdrive module 2170 is in the locked position. Switch 2172 can be used to verify that flexdrive module 2170 is in the locked or unlocked position. In the locked position, arm/pin 2174 presses switch 2172 into a closed position. In the unlocked position, arm/pin 2174 does not engage switch 2172 and it reverts to an open position.

The flexdrives can be designed to lock in place to hold the twisted string in a fixed position without require the drive motor to expend energy to maintain that hold. FIGS. 22-27 show different locking mechanisms that may be used in flexdrives according to various embodiments. Starting with FIG. 22, views of a solenoid mechanical interlock assembly 2200 according to an embodiment is shown. Assembly 2200 can include push-pull solenoid 2210 that is attached to engagement member 2212. Engagement member 2212 is operative to interface with sectioned lock wheel 2220, which is coupled to encoder 2230 drive motor 2240. In the unlocked position, solenoid pulls engagement member 2212 back away from lock wheel 2220. In the locked position, solenoid pushes engagement member 2212 into lock wheel 2220 to lock drive motor 2040 in place.

Figure 23:
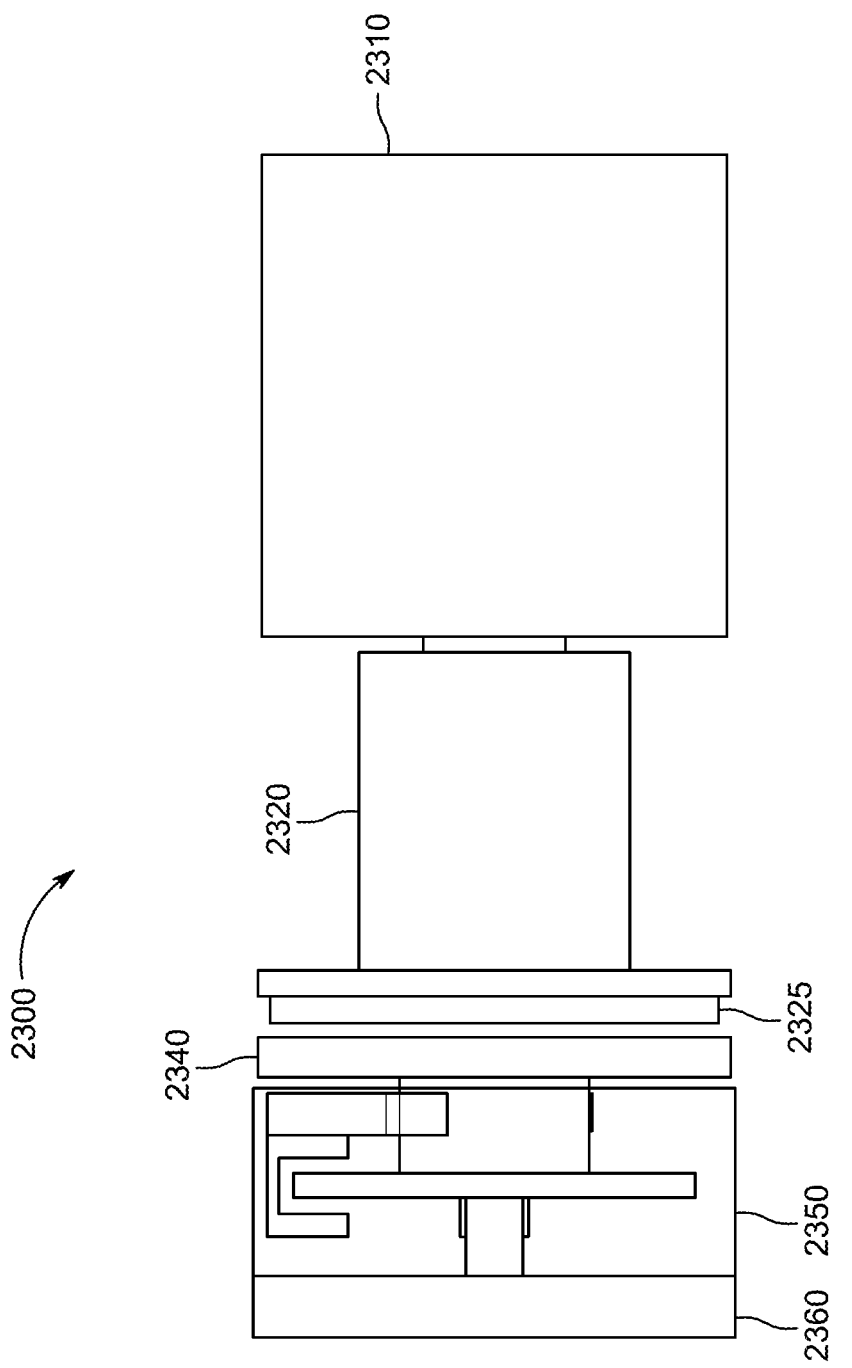
FIG. 23 shows a lead screw locking mechanism assembly according to an embodiment.

FIG. 23 shows a lead screw locking mechanism assembly 2300 according to an embodiment. Assembly 2300 can include motor 2310, nut 2320, friction pad 2325, and cone 2340. Cone 2340 may be coupled to encoder 2350, which is secured to drive motor 2360. To lock drive motor 2360, motor 2010 may cause nut 2320 (and by extension friction pad 2325) to press into cone 2340. When sufficient force is applied to cone 2340 by friction pad 2325, cone 2340 may be locked in place. To unlock drive motor 2360, motor 2310 can pull nut 2320 away from cone 2340 to decouple friction pad 2325 from cone 2340.

Figure 24:
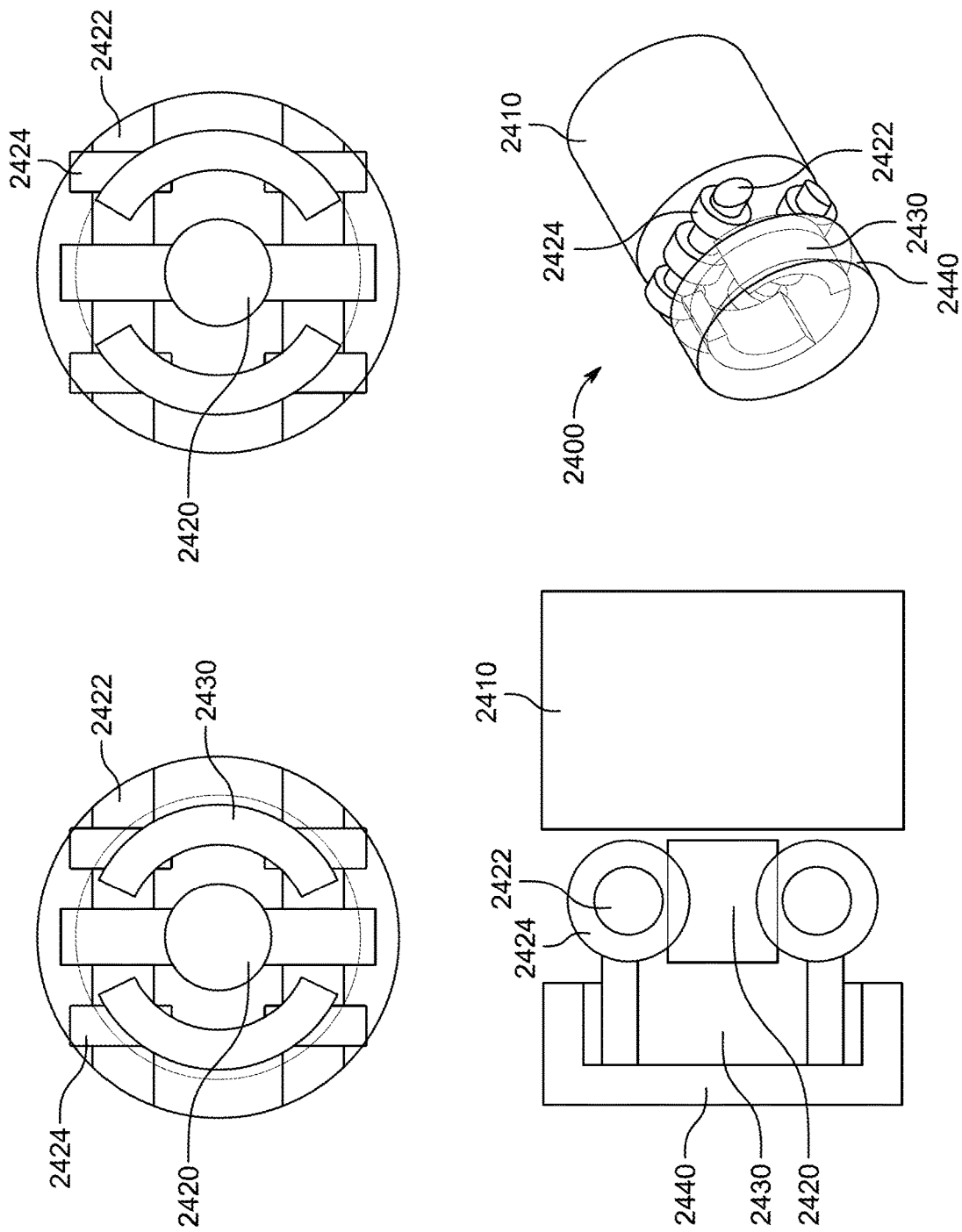
FIG. 24 shows a worm drive locking mechanism assembly according to an embodiment.

FIG. 24 shows a worm drive locking mechanism assembly 2400 according to an embodiment. Assembly 2400 can include motor 2410, worm 2420, lead screw 2422, worm gear 2424, friction shoe 2430, and drive motor attachment 2440. To lock the drive motor in place, motor 2410 may turn worm 2420 in a first direction to cause friction shoe 2430 to expand and engage motor attachment 2440. When worm 2420 turns, it engages worm gear 2424, which causes lead screw 2422 to move friction shoe 2430. To unlock the drive motor, motor 2410 may turn worm 2420 in the opposite direction to cause friction shoe 2430 to not engage motor attachment 2440.

Figure 25:
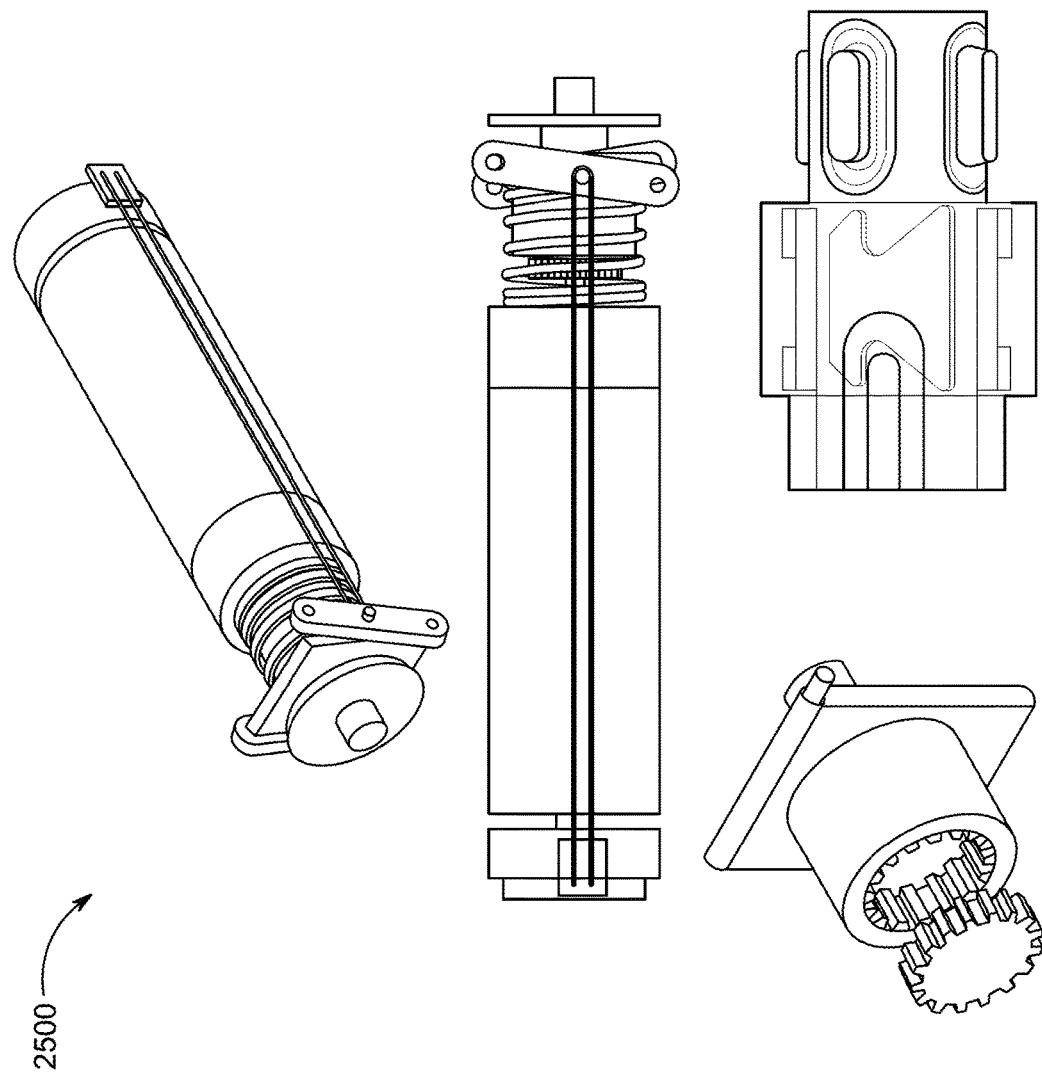
FIG. 25 shows a nitinol actuated push-push mechanism assembly according to an embodiment.

FIG. 25 shows a nitinol actuated push-push mechanism assembly 2500 according to an embodiment.

FIG. 26 shows a solenoid lock mechanism assembly 2600 according to an embodiment.

Figure 27:
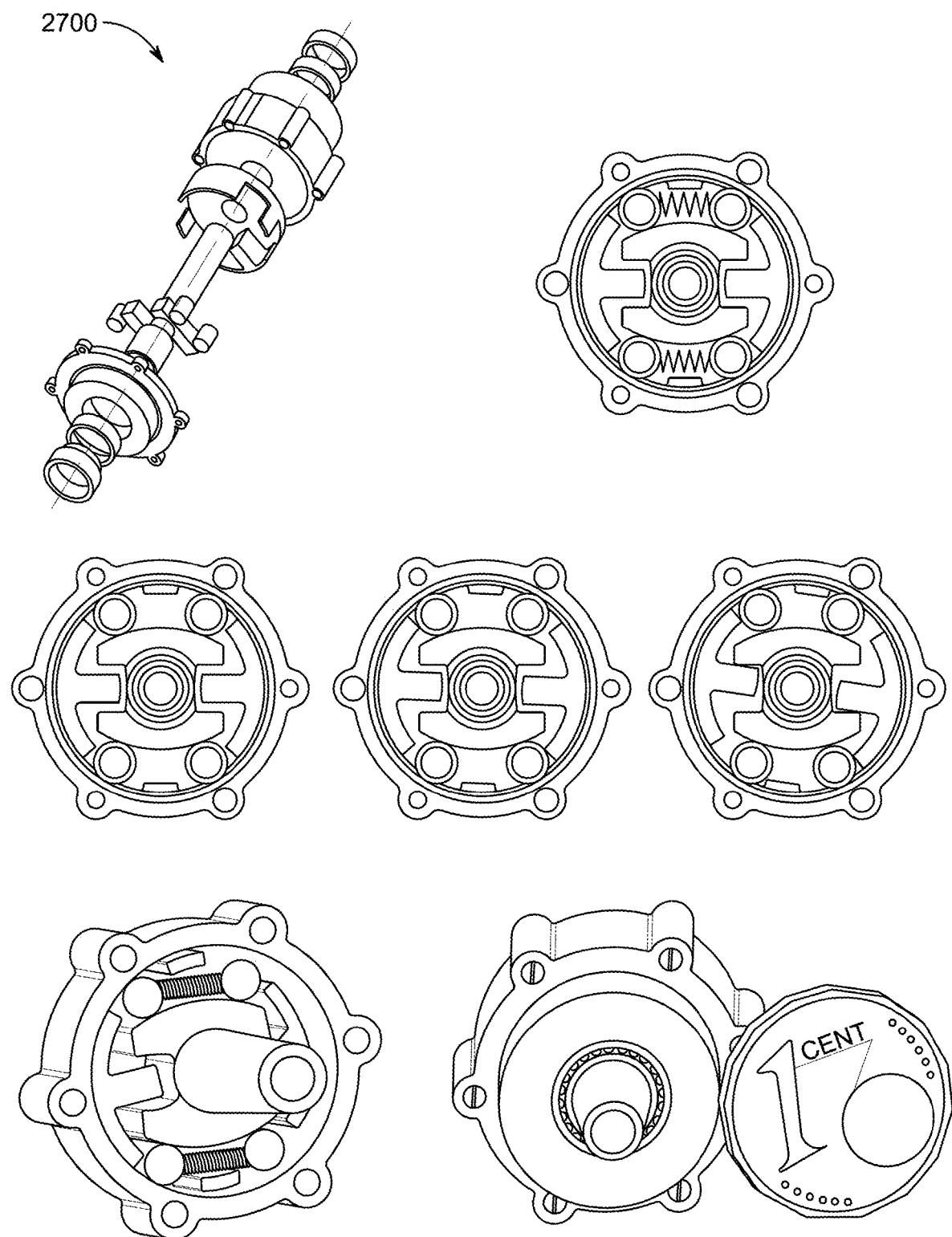
FIG. 27 shows a non-backdrivable lock mechanism assembly according to an embodiment.

FIG. 27 shows a non-backdrivable lock mechanism assembly 2700 according to an embodiment.

Users of the exosuit will have to use the toilet, and as such, appropriate regions of the user's body need to be exposed. The user may not or cannot doff the exosuit to toilet for at least the reason that is inconvenient to do so and that the user may require assistance from the exosuit while toileting (e.g., urinating into a toilet in a standing position) or standing up from the toilet after sitting thereon. Different toileting embodiments are now discussed.

Figure 30C:
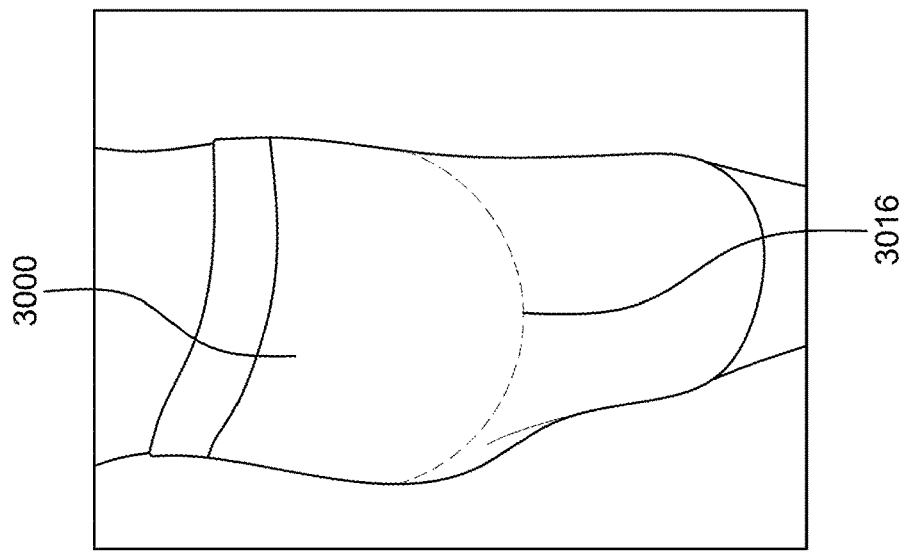
FIGS. 30A-30C show illustrative front, back, and side views of next to skin layer having toileting access according to an embodiment.
Figure 30B:
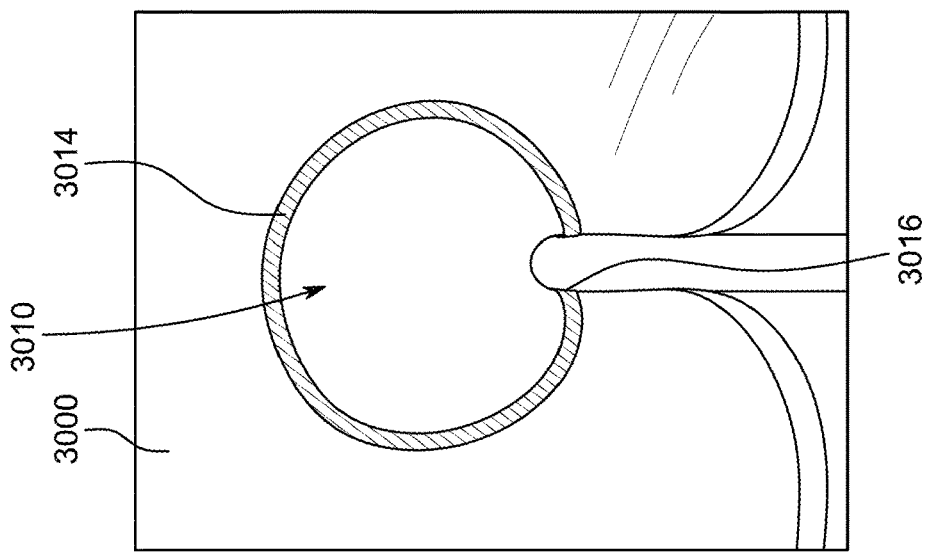
Figure 30A:
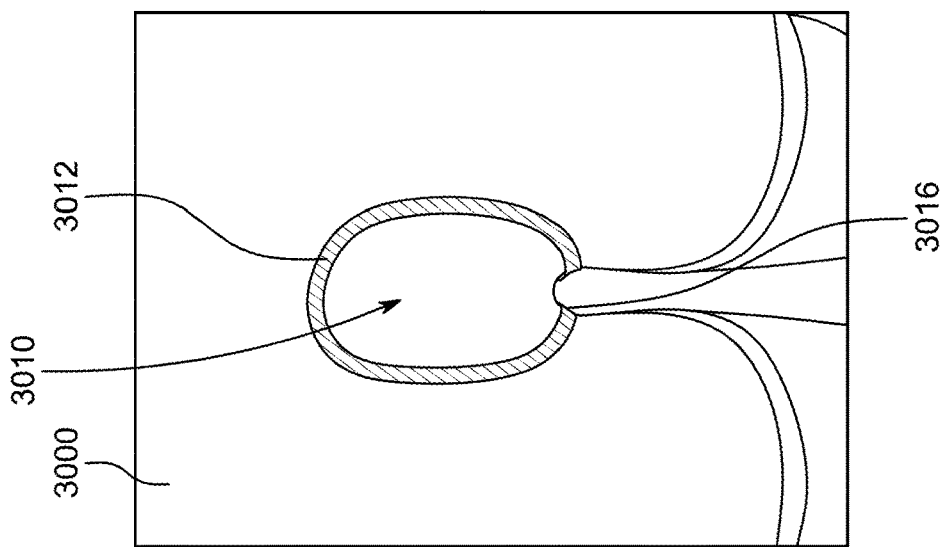

FIGS. 30A-30C show illustrative front, back, and side views of next to skin layer 3000 having toileting access 3010. Toileting access 3010 may be a cutout existing on the front and back sides of layer 3000. Access 3010 can include hole 3012 on the front side and hole 3014 on the back side. Channel gap 3016 may exist between holes 3012 and 3014. Hole 3012 may be smaller in size than hole 3014.

Figure 31C:
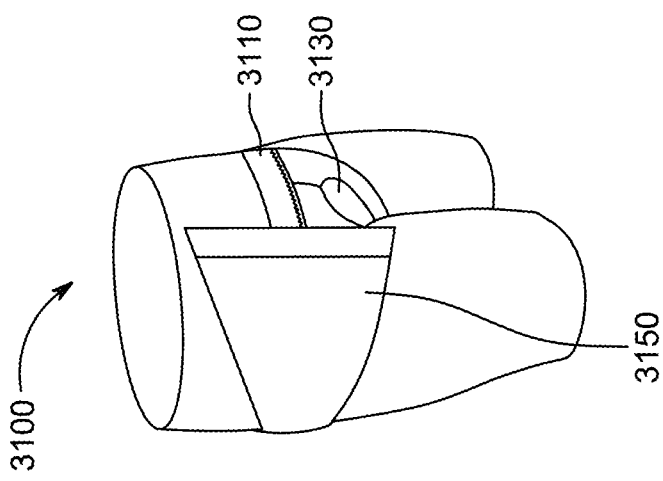
FIGS. 31A-31F show different views of next to skin layer having a removable flap according to various embodiments.
Figure 31B:
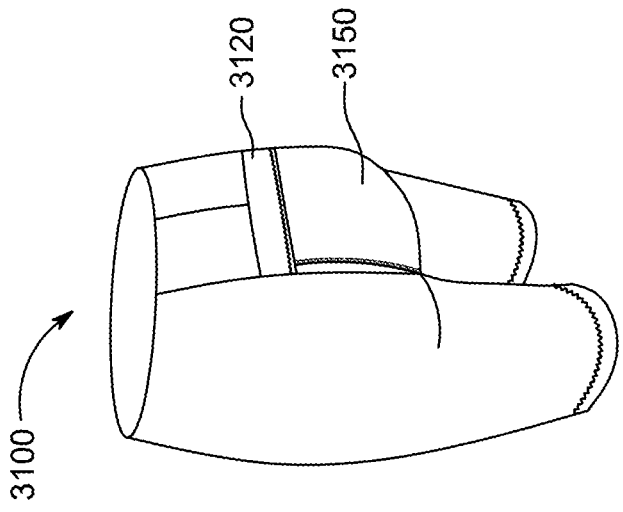
Figure 31A:
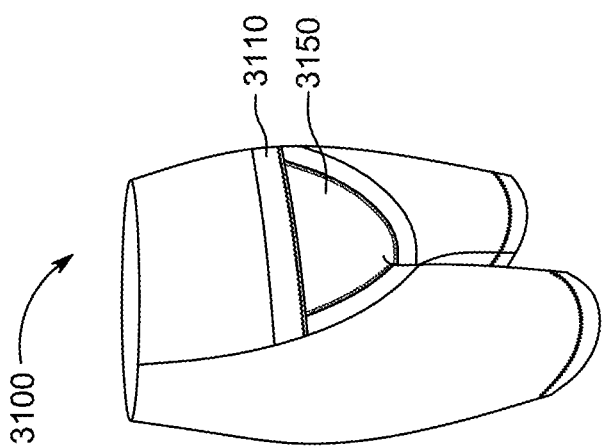

FIGS. 31A-31F show different views of next to skin layer 3100 having a removable flap 3150 according to various embodiments. FIGS. 31A and 32B show illustrative front quarter and back quarter views of skin layer 3100 with flap 3150 attached in place. Flap 3150 may be attached front attachment region 3110 and rear attachment region 3120. Flap 3150 may be attached to regions 3110 and 3120 via magnets, hook and loop (e.g., Velcro), button snaps, or a combination thereof. When the user wishes to use the toilet (as shown in FIG. 31C), he or she may decouple flap 3150 from regions 3110 and 3120 to expose cutout 3130 that exist under flap 3150. If desired, the user may wrap flap 3150 around his or her waist and secure flap 3150 to regions 3110 and 3120. Cutout 3130 may extend from the front to the back of layer 3100 to bridge the front and rear openings.

Figure 31F:
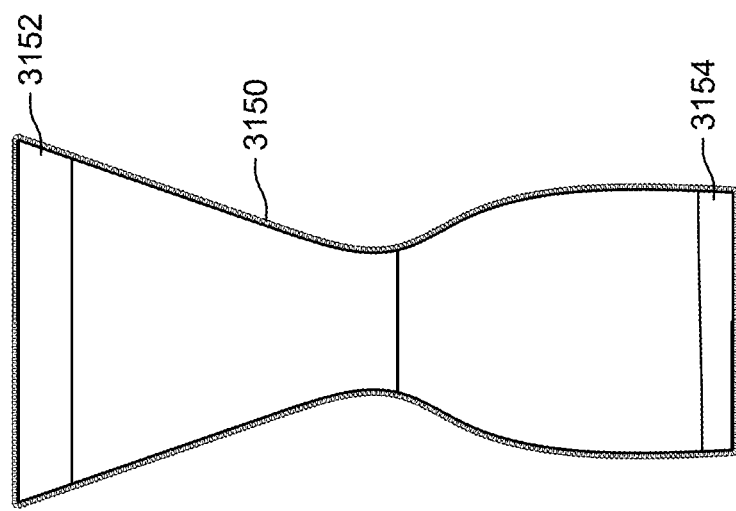
Figure 31E:
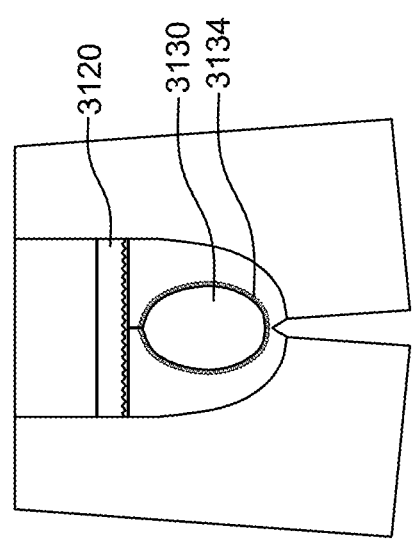
Figure 31D:
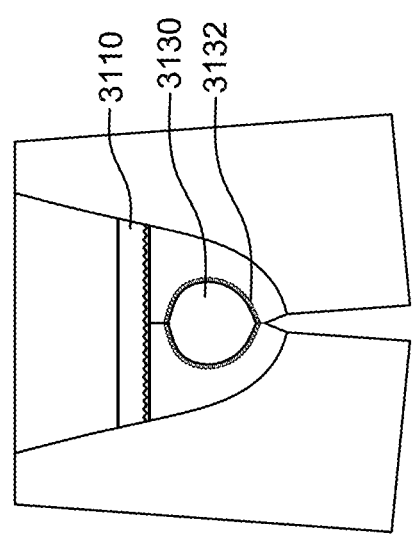

FIGS. 31D and 31E shows illustrative front and back views of layer 3100 with flap 3150 removed. Cutout 3130 can include first hole 3132 and second hole 3134 with open channel (not shown) connected to both holes 3132 and 3134. Front attachment region 3110 and rear attachment region 3120 may include overlap pockets into which ends of flap 3150 may be inserted. FIG. 31F shows an illustrative view of flap 3150 with end portions 3152 and 3154. Each of end portions 3152 and 3154 can include one of magnets, hook and loop (e.g., Velcro), button snaps for being secured to regions 3110 and 3120. In embodiments that use magnets, the magnets may be removable (to promote ease of washing). For example, the magnets may exist on a strip that can be removed from flap 3150 and regions 3110 and 3120. In some embodiments, a portion of flap 3150 may be lined with a water proof membrane to help with incontinence and provide structural support to flap 3150 to prevent twisting.

FIGS. 32A-32C show illustrative front, back, and side view of exosuit 3200 showing all layers but cover layer. FIG. 33A-33C show illustrative front, back, and side view of N2S layer 3210. N2S layer 3210 may include donning handles 3211 that assist the user in donning and doffing N2S layer 3210, buckles 3212 for adjusting donning handles 3211, zipper 3213, and hem stabilizers 3219. Layer 3210 can include shoulder harness 3215, which may include buckles 3216 for adjusting the size of the shoulder harness, and shoulder strap swivel points 3217. Shoulder strap 3215 can include hook and loop segments for adjusting the sizing of the shoulder strap. Shoulder strap 3215 can be padded for comfort. Pivot points 3217 may enable flex or pivoting in of the shoulder strap. Shoulder harness 3215 may be integrally formed as part of layer 3210 or it can be a separate component that can be coupled to the layer 3210.

Figures 34A, 34B, 34C:
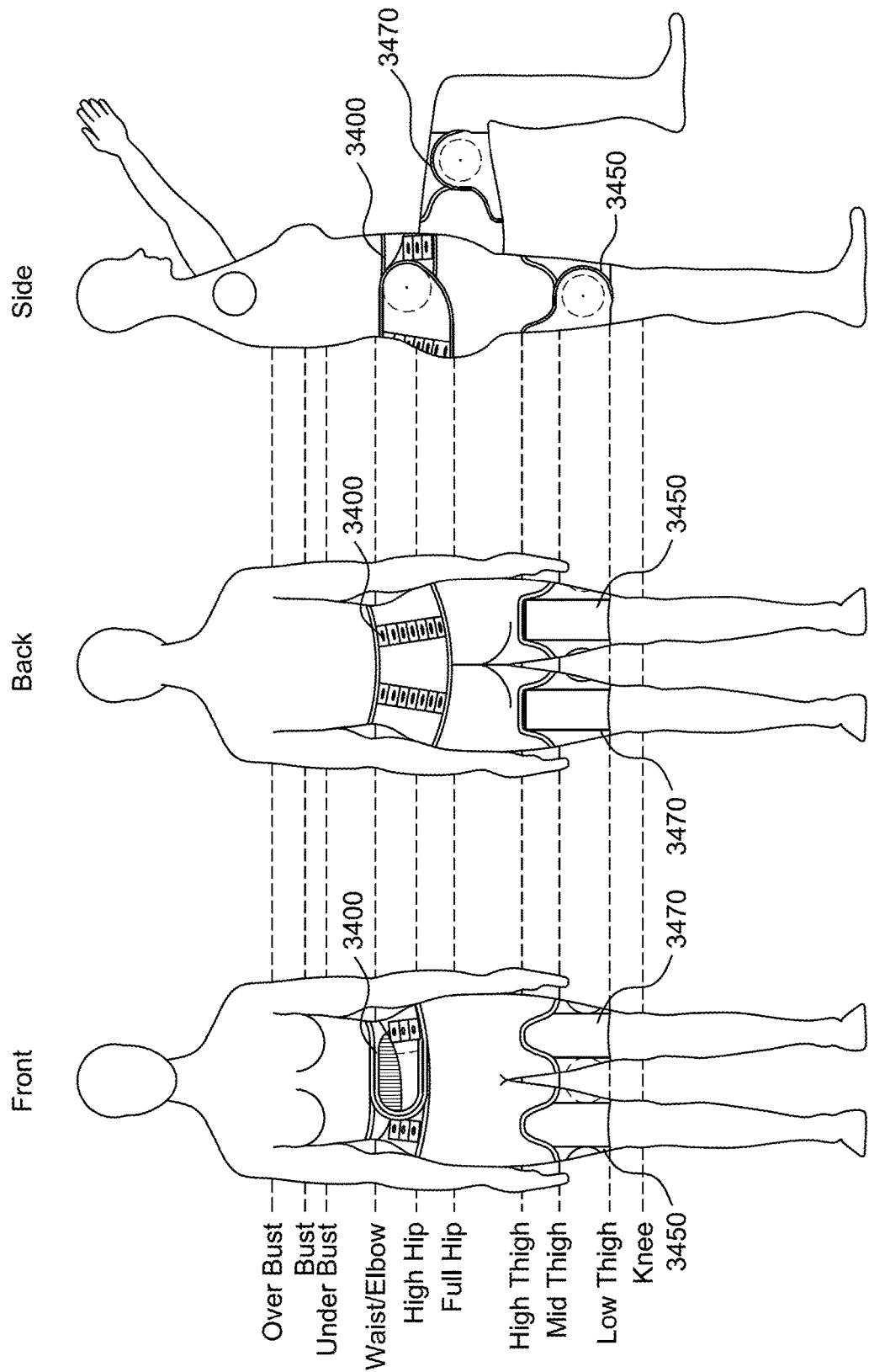
FIGS. 34A-34C show illustrative front, back, and side view of pelvis load distribution member and thigh load distribution members according to various embodiments.

FIGS. 34A-34C show illustrative front, back, and side view of pelvis load distribution member 3400 and thigh load distribution members 3450 and 3570. Each of LDMs 3400, 3450, and 3470 may include two or three components that attach to each other to form a loop that surrounds their respective body parts. For example, pelvis LDM 3400 may be a three part loop and thigh LDMs 3450 and 3470 may be a two part loop. The multi-part construction of LDMs 3400, 3450, and 3470 provides for a highly customizable fit for the wearer. Each part can be rotated with respect to each other, for example, to accommodate for the particular shape of the wearer. In addition, the coupling between each part can be length adjusted to accommodate for different sizes of the wearer. LDMs 3400, 3450, and 3470 can be constructed with a combination of fabric materials, some of which are compliant (i.e., stretch) and non-compliant (i.e., no stretch), and rigid members that serve as support structures for flexdrive components and enable loads to be distributed into the tissue of the wearer in a substantially uniform manner. The fabric provides comfort of fit and may be designed to interface with an next-2-skin layer.

FIGS. 35A-35H show exterior and interior views of back member 3500, left member 3530, and right member 3560 that collectively form pelvis LDM 3400. FIGS. 35A-35C and 35G show exterior views, and FIGS. 35D-35F and 35H show interior views. Back member 3500 can include flange member 3502 that defines a periphery of member 3500, non-stretch regions 3504, pelvis stay 3506 that is incorporated within member 3530 to provide rigid support, and anchor stays 3508 for interfacing with flexdrive components (not shown). Back member 3500 can include loop regions 3511-3513 (sometimes referred to herein as interface regions) and hook region 3515. Loop region 3511 may be located on a distal end of member 3500 and loop region 3513 may be located at the other distal end of member 3500. Both of loop regions 3511 and 3513 may be circular in shape. Back member 3500 may have a slight curve shape to better fit along a back region of the wearer. A rigid member may be incorporated between flange member 3502 and non-stretch regions 3504 to provide additional loading support for flexdrive components.

Referring now to left member 3530, left member 3530 may include loop region 3532, stay member 3534 that is incorporated within member 3530 to provide rigid support. Left member 3530 can include flange member 3533 that defines a periphery of member 3530 and relatively high friction fabric 3535. Loop region 3532 may have an oblong shape (as opposed to a circular shape) to allow for flexibility in fit adjustment. Left member 3530 can include elastic fabric 3536, non-stretch fabric 3538, hook region 3540, pocket 3542, and anchor 3544. Right member 3560 may include elastic fabric 3562, non-stretch fabric 3564, stay 3566 that is incorporated within member 3560 to provide rigid support. Right member 3560 can include hook regions 3568 and 3570 and anchors 3572.

Figure 35G:
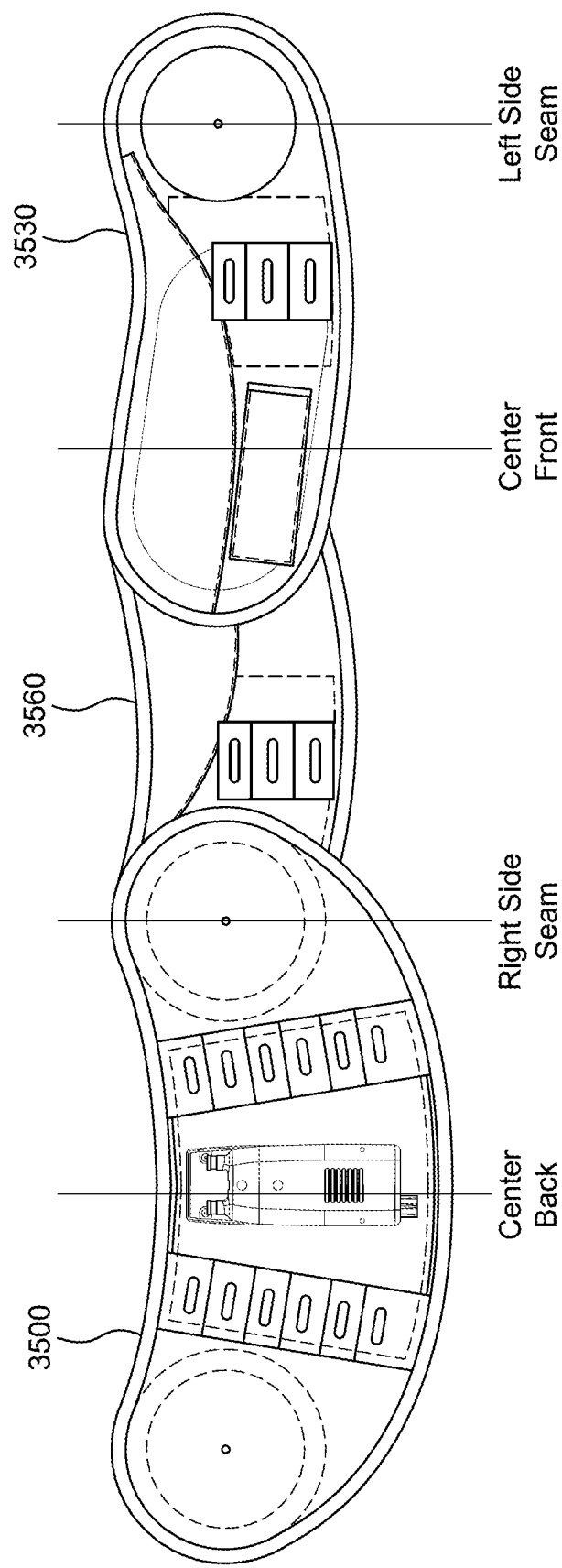
Figure 35H:
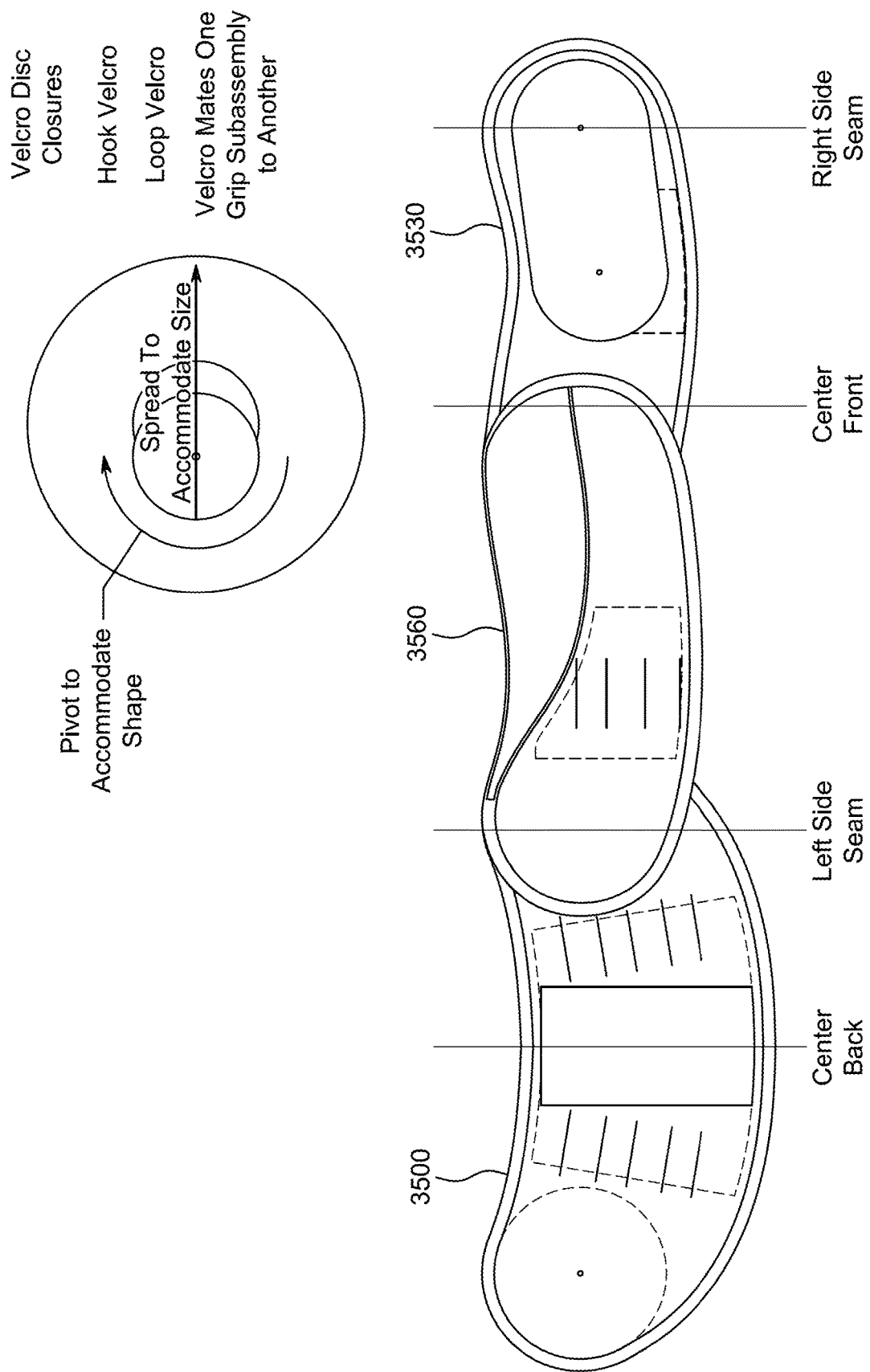

Referring to FIGS. 35G and 35H in particular, right member 3560 is attached to back member 3500 and to left member 3530, and left member is attached to back member 3500. The attachments may be accomplished through the hook and loop regions on each of the members. The hook and loop regions allow members 3500, 3530, and 3560 to be rotated with respect to each other to best fit around the pelvis. For example, the rotation of one member respect to another may allow a user to adjust the fit of member 3400 for his or her body shape. In addition, members 3500, 3530, and 3560 can be coupled together to accommodate different lengths so that pelvis member 3400 can fit around the pelvis. It should be appreciated that various aspects of members 3500, 3530, and 3560 may be changed as desired. For example, the sizing of the hook and loop regions may be changed, the sizing of the stretch regions and the non-stretch regions may be changed, the shape and orientation or number anchors may be changed, and the size of the stays may be changed or their rigidity can be changed.

Figure 36D:
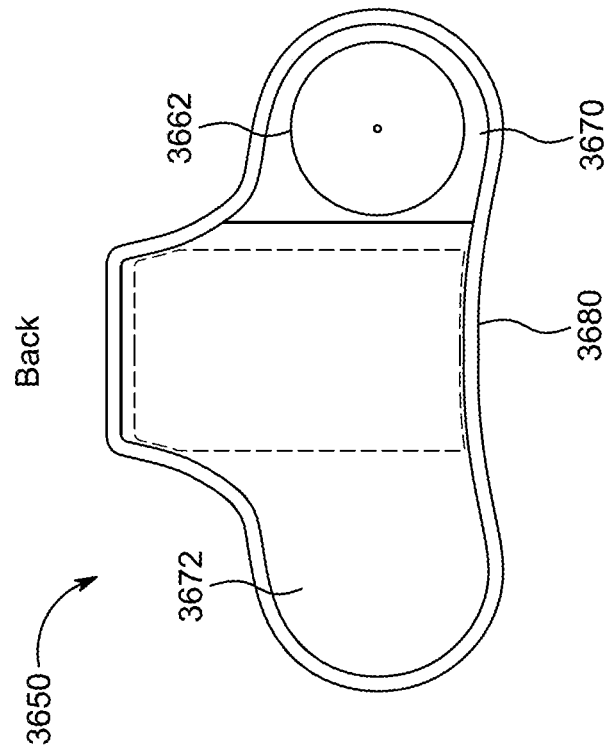
Figure 36C:
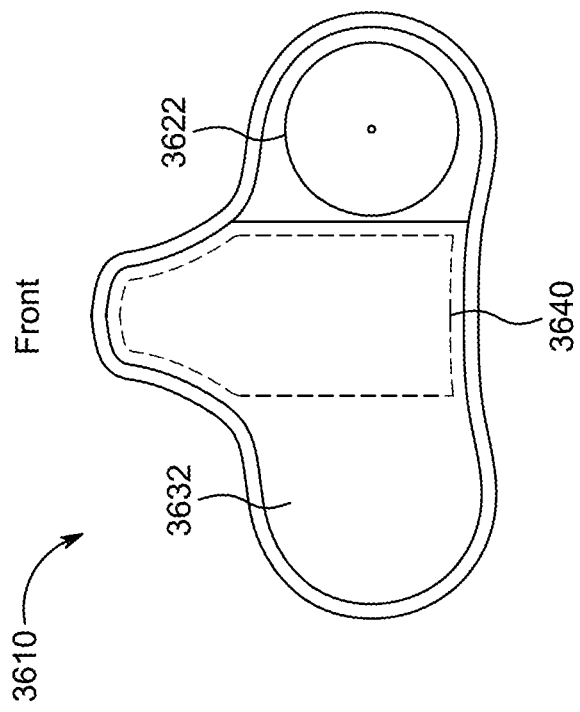
Figure 36E:
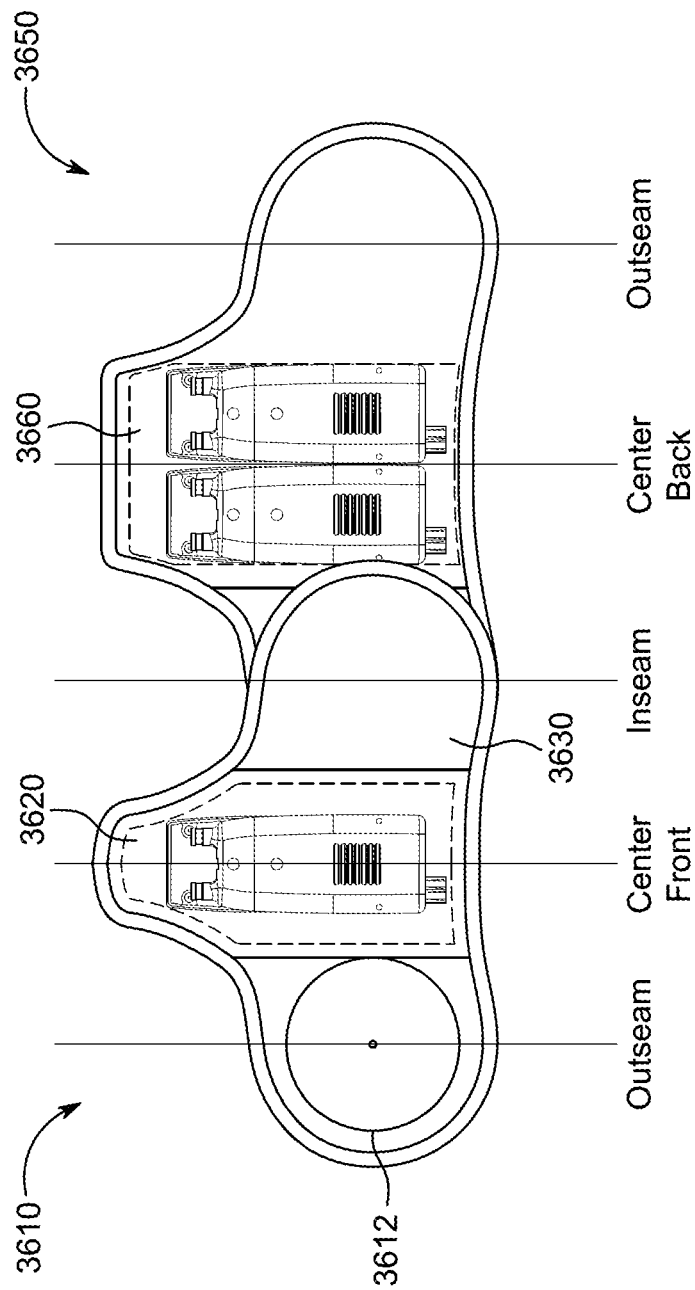
Figure 36F:
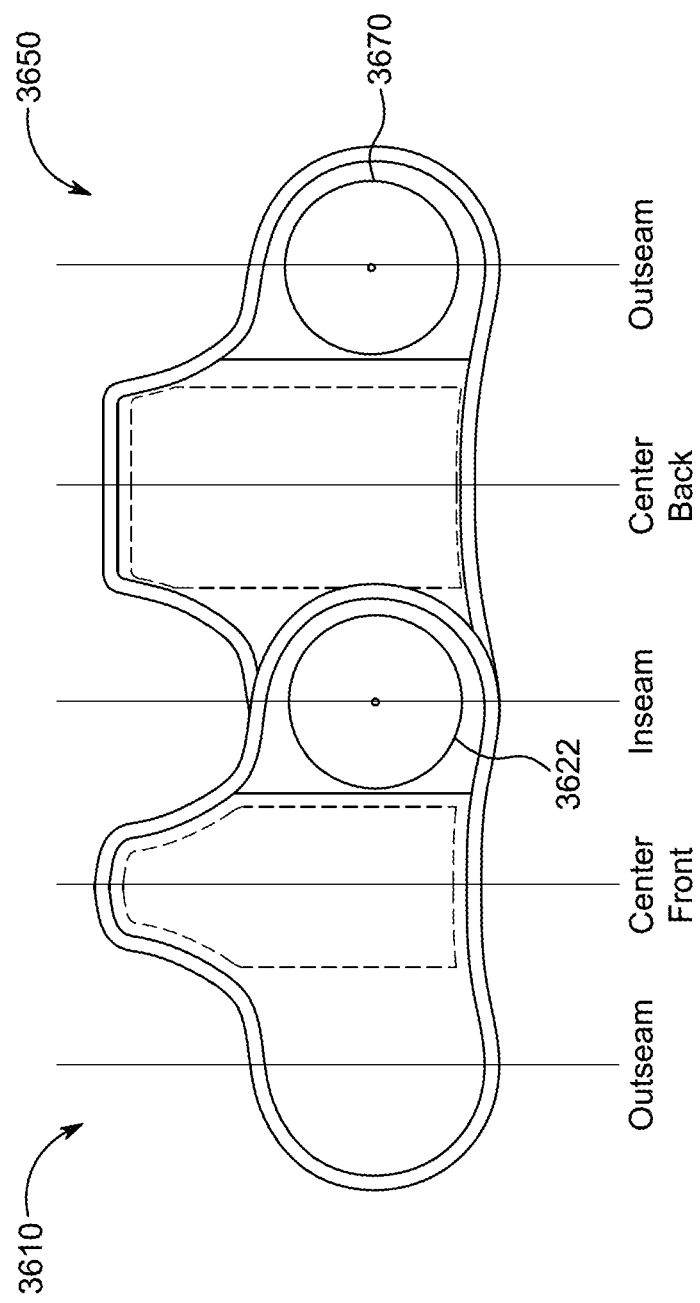

FIGS. 36A-36F show different views of components of thigh load distribution members such as, for example members 3450 and 3470. Each of members 3450 and 3470 can include front member 3610 and back member 3650. Both members 3610 and 3650 may attach to each other via hook and loop regions to wrap around the leg or thigh of the user. FIGS. 36A, 35C, and 36E show exterior views, and FIGS. 36B, 36D, and 36F show interior views. Front member 3610 can approximate a "T" shape that has hook region 3612, loop regions 3620 and 3622, non-stretch fabric 3630, and relatively high friction fabric 3632. Front member 3610 can include stay 3640 (as shown by dashed line outline) that is contained between layers defining the top surfaces of front and back members 3610 and 3650. Back member 3650 can also approximate a "T" shape, but is different in dimension compared to front member 3510. Back member 3650 can include hook region 3652, loop regions 3660 and 3662, non-stretch fabric 3670, and relatively high friction fabric 3672. Back member 3650 can include stay 3680 (as shown by dashed line outline) that is contained between layers defining the top surfaces of front and back members 3610 and 3650. Flexdrive components may be attached to stay regions 3640 and 3680, particularly, on the exterior side of members 3610 and 3650.

Figure 37:
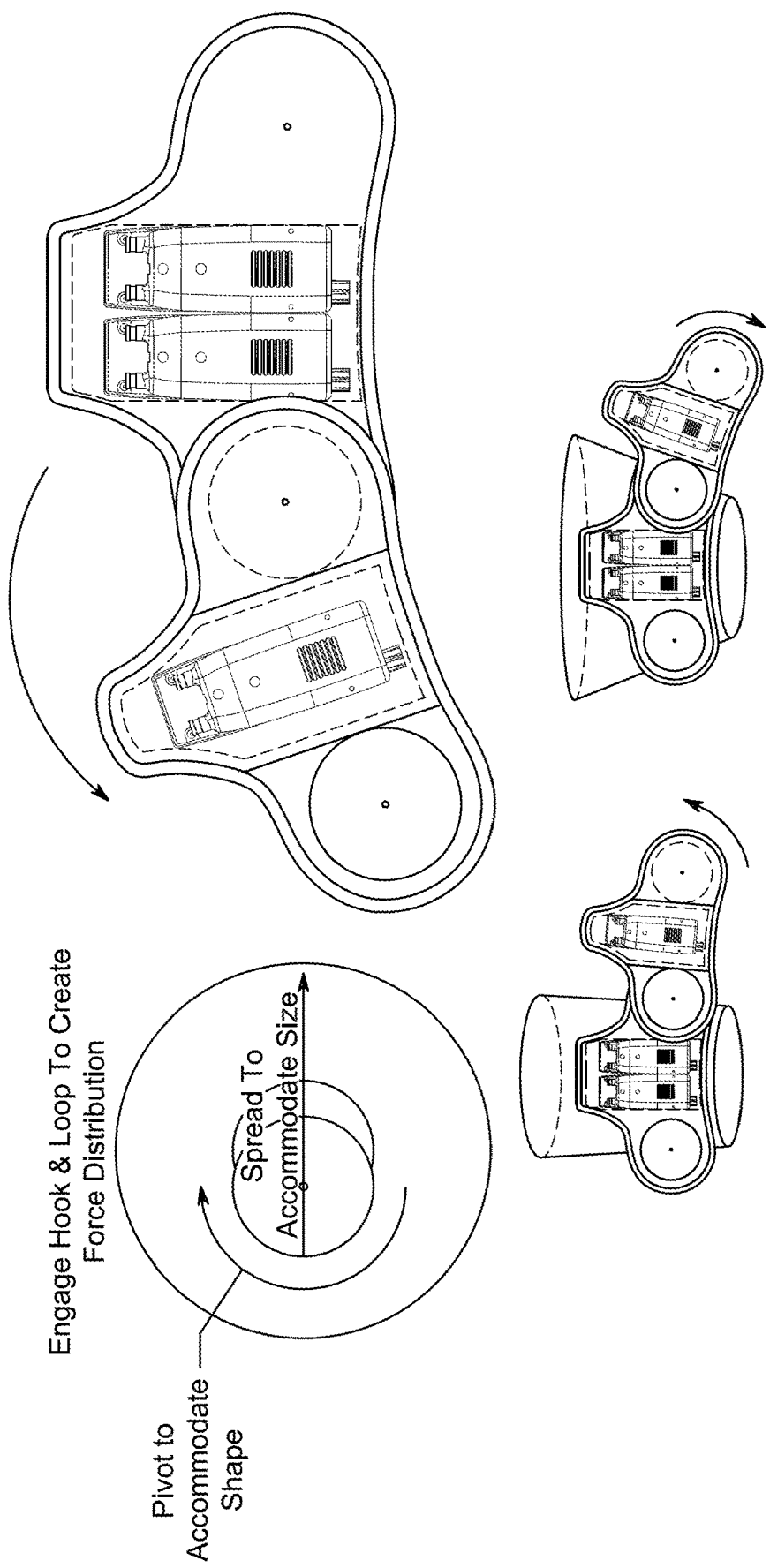
FIG. 37 shows how different members can be connected together to wrap around different sized legs according to various embodiments.
Figure 38A:
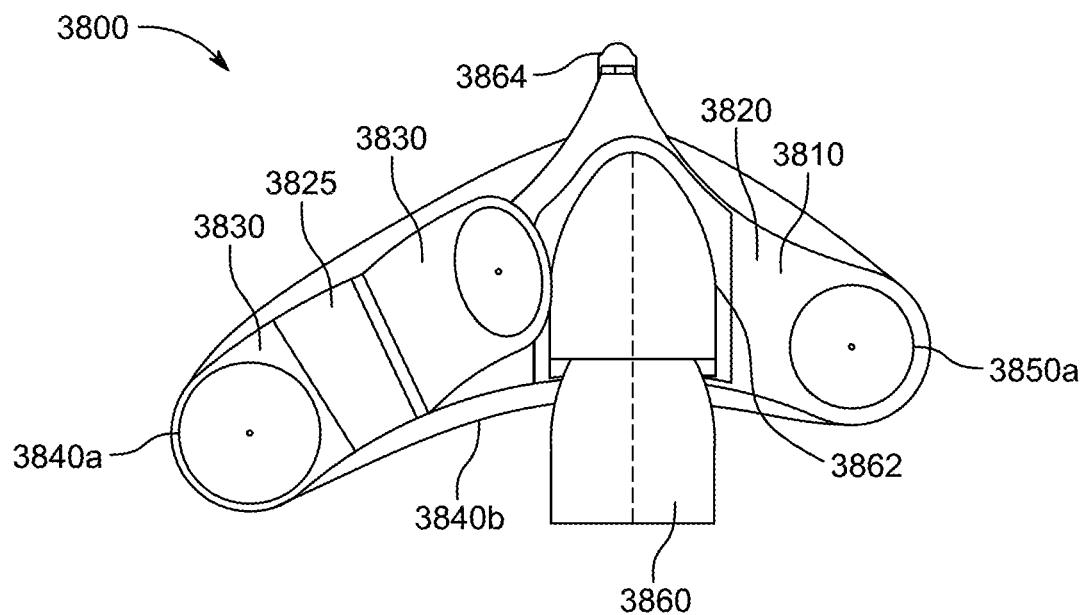
FIGS. 38A-38F show another thigh distribution member that may be used in connection with an exosuit according to an embodiment.
Figure 38B:
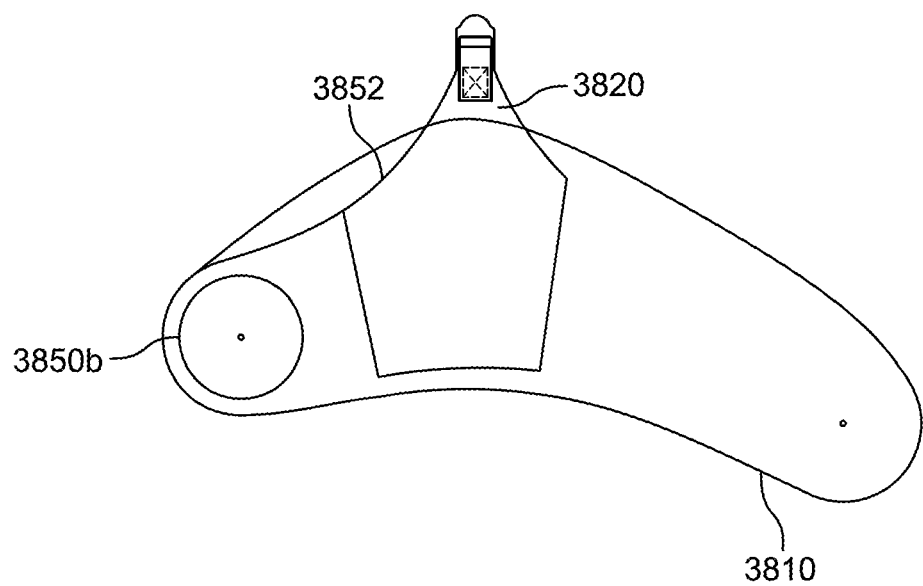
Figure 38C:
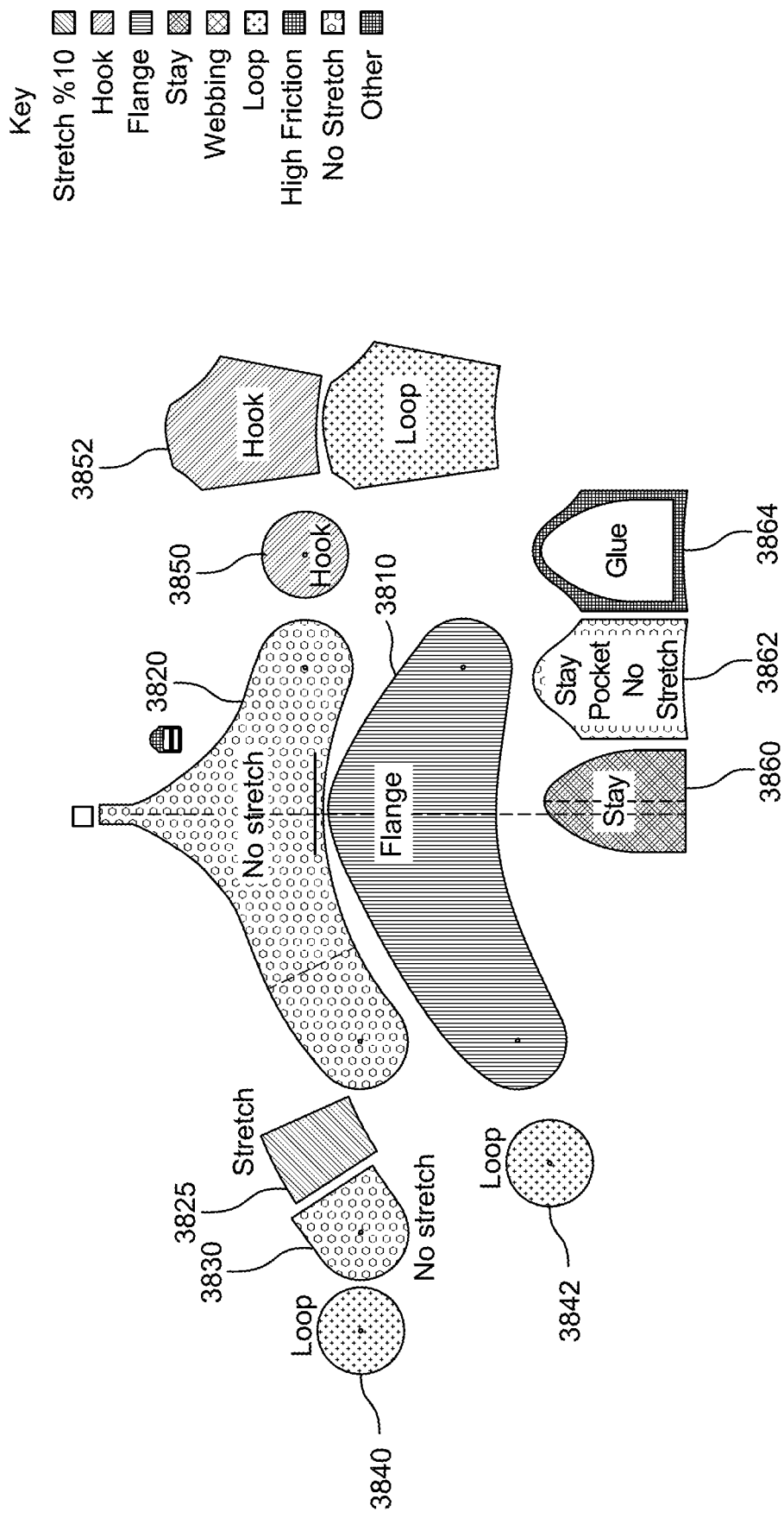
Figure 38D:
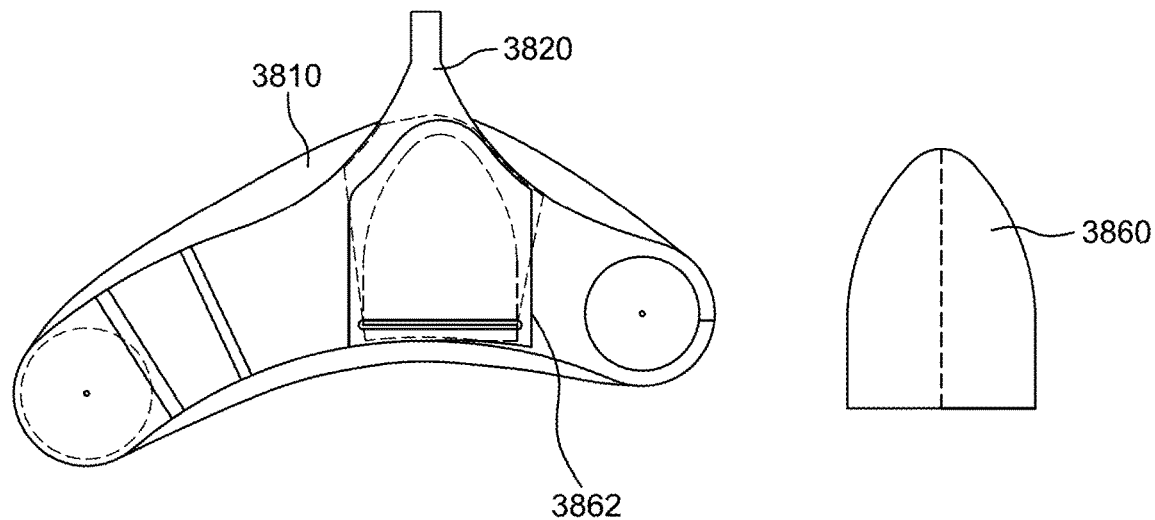
Figure 38E:
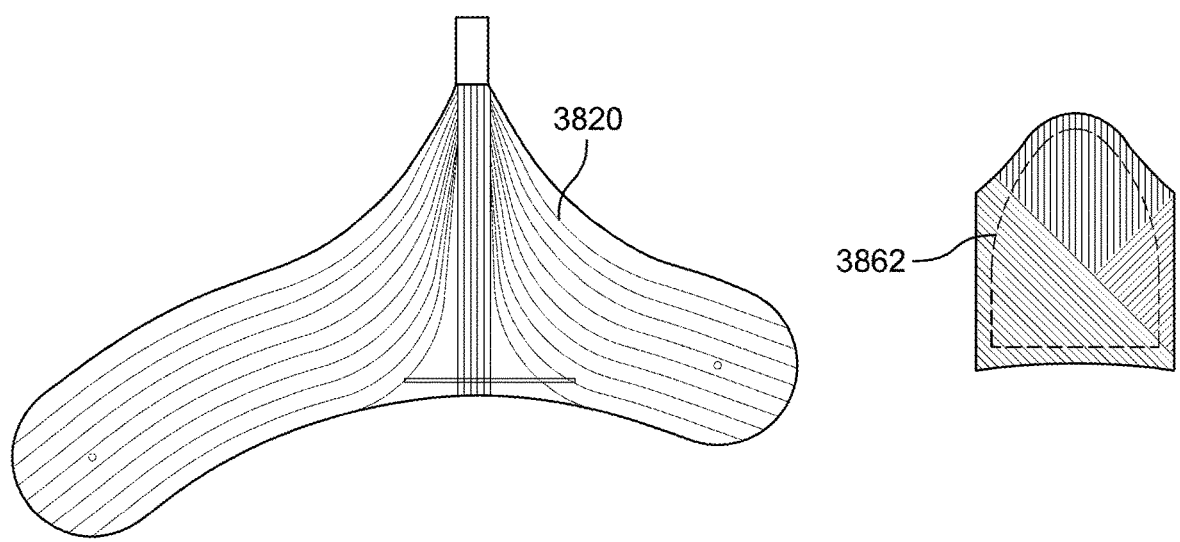
Figure 38F:
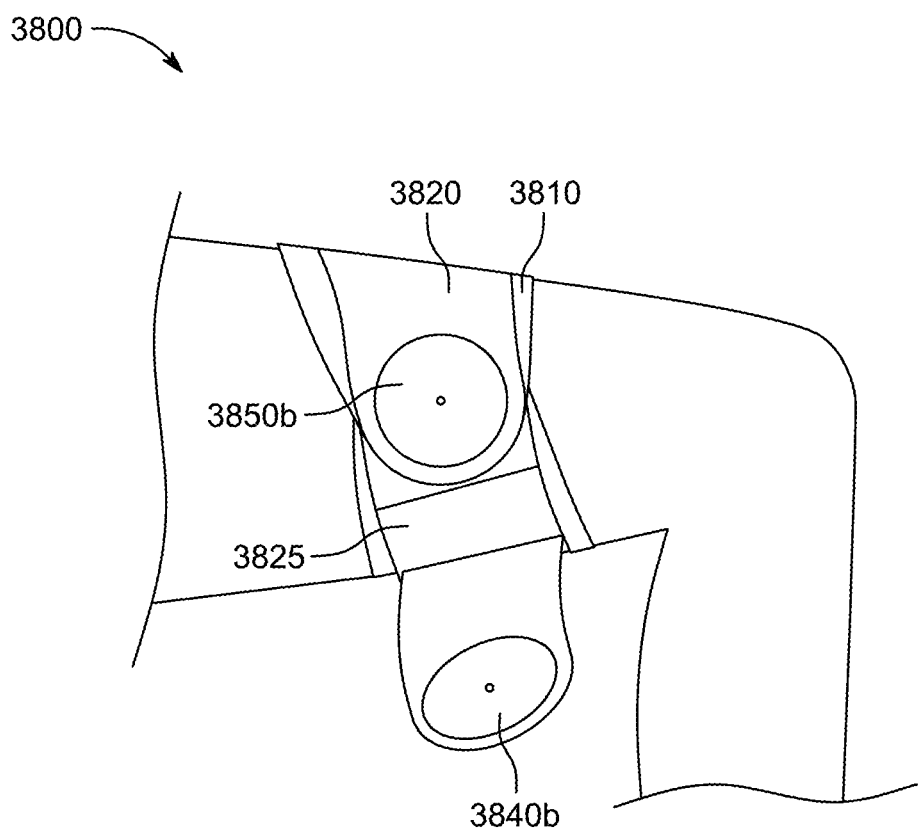

FIG. 37 shows how members 3610 and 3650 can be connected together to wrap around different sized legs. The hook and loop connections can be enable member 3610 to be rotated with respect to member 3650. The degree to which hook and loop connections overlap can be changed.

FIGS. 38A-38F show another thigh distribution member 3800 that may be used in connection with an exosuit. Thigh distribution member 3800 may differ from member 3450 in that it is does not require two or more separate components to wrap around the thigh. In contrast, member 3800 may be a single component that wraps around the leg and attaches to itself. See, for example, FIG. 38F, which shows member 3800 wrapped around the leg. Member 3800 may be a multi-piece construction that includes flange member 3810, no stretch member 3820, stretch member 3825, no stretch member 3830, loop regions 3840a, 3840b, and 3842, hook regions 3850a, 3850b, and 3852, stay 3860, stay pocket 3862, adhesive layer 3864, and buckle 3870.

Flange member 3810 may serve as base member on to which other components of member 3800 are attached. Stay pocket 3862 may be secured to flange member 3810 via adhesive 3864 and stay 3860 may be contained in stay pocket 3862. No stretch member 3820 may be secured on top of flange member 3820, stay 3860, and stay pocket 3862. Loop region 3840a may be secured on top of no stretch member 3820 as shown. Hook region 3850a may be secured on top of no stretch member 3820 as shown. Stretch member 3825 may be secured on top no stretch member 3820 and to no stretch member 3830. Loop region 3840b may be secured to no stretch member 3830. Hook region 3850b and hook region 3852 may be secure to the back of flange member 3810.

During donning of member 3800, the user may attach loop region 3840a to hook region 3850a to make a first connection. Then, the user may attach loop region 3840b to hook region 3850b to make a second connection. Stretch region 3825 may provide flexibility in allowing the user to adjust how tight or loose regions 3840b and 3850b are attached together.

FIGS. 39A-39C show illustrative front, back, and side showing patch members 3900 and 3950 that may be mounted on top of load distribution members (not shown) and are secured to portions of flexdrives. Patch members 3900 and 3950 may be constructed to interface with respective load distribution members. The interface may take any suitable approach such as hook and loop attachments, snap fasteners, and/or strap and buckle attachments. Flexdrive assemblies 3910-3912 may be attached to patch member 3900, and flexdrive assemblies 3960-3962 may be attached patch member 3950.

Figure 40A:
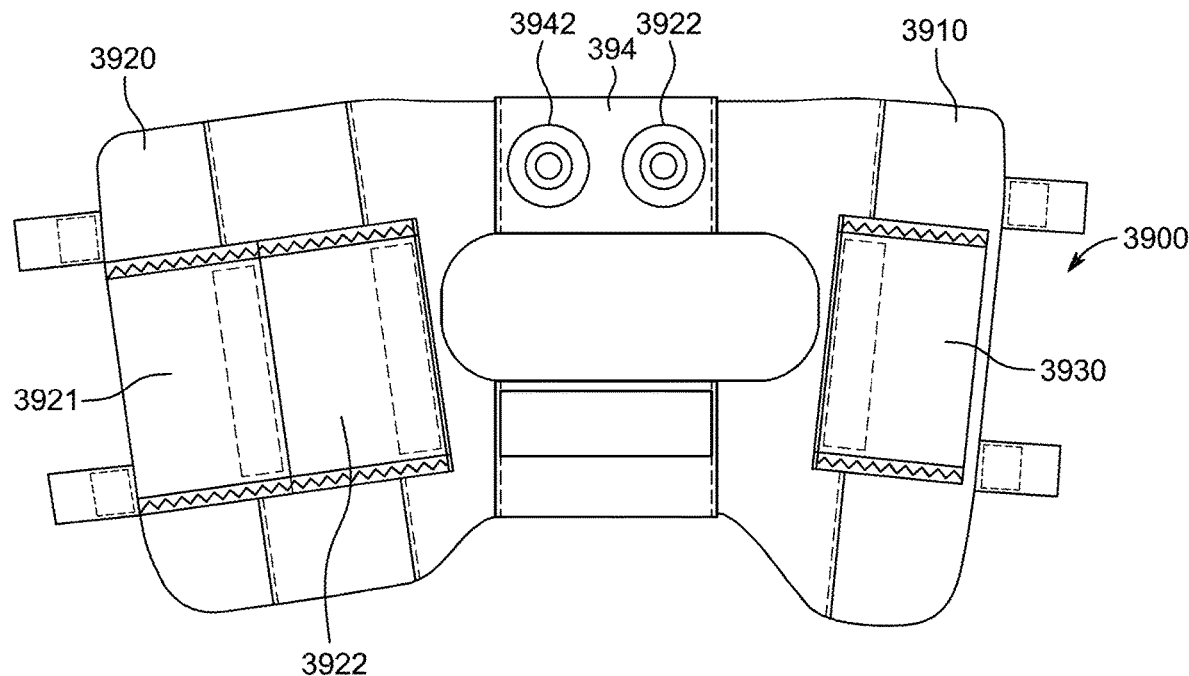
FIGS. 40A-40C show different views of patch member of FIGS. 39A-39C according to an embodiment.
Figure 40B:
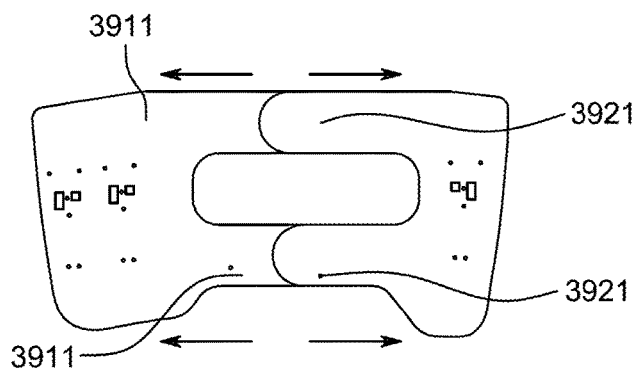
Figure 40C:
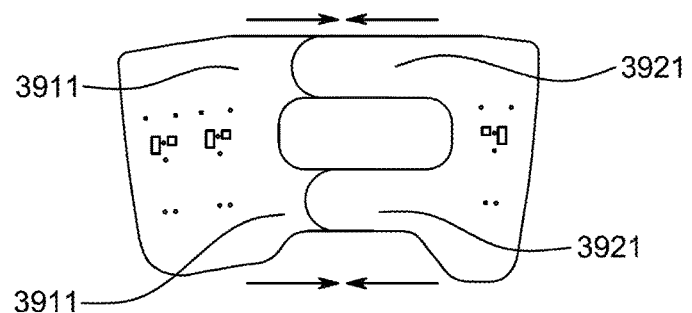

FIGS. 40A-40C show different views of patch member 3900 according to an embodiment. Patch member 3900 can include front base layer 3910, back base layer 3920, flexdrive pockets 3930-3932, and removable band 3940 with snaps 3942. Front base layer 3910 can include finger regions 3911 and back base layer 3920 can include finger regions 3921. Finger regions 3911 and 3921 can attach to each other at different locations to adjust a sizing fit of patch member 3900 around a leg. Flexdrives (not shown) can be secured to flexdrive pockets 3930-3932 and other components (not shown) can be attached snaps 3942.

An exosuit can be operated by electronic controllers disposed on or within the exosuit or in wireless or wired communication with the exosuit. The electronic controllers can be configured in a variety of ways to operate the exosuit and to enable functions of the exosuit. The electronic controllers can access and execute computer-readable programs that are stored in elements of the exosuit or in other systems that are in direct or indirect communications with the exosuit. The computer-readable programs can describe methods for operating the exosuit or can describe other operations relating to a exosuit or to a wearer of a exosuit.

Figure 28:
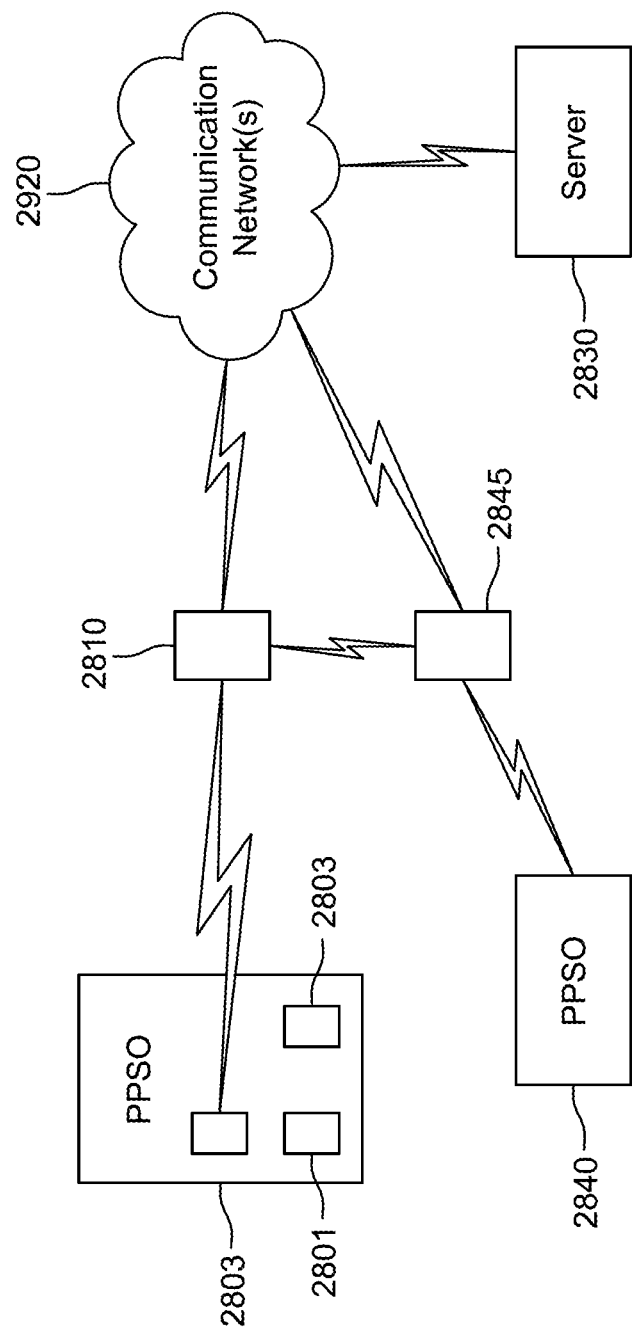
FIG. 28 illustrates an example exosuit according to an embodiment.

FIG. 28 illustrates an example exosuit 2800 that includes actuators 2801, sensors 2803, and a controller configured to operate elements of exosuit 2800 (e.g., 2801, 2803) to enable functions of the exosuit 2800. The controller 2805 is configured to communicate wirelessly with a user interface 2810. The user interface 2810 is configured to present information to a user (e.g., a wearer of the exosuit 2800) and to the controller 2805 of the flexible exosuit or to other systems. The user interface 2810 can be involved in controlling and/or accessing information from elements of the exosuit 2800. For example, an application being executed by the user interface 2810 can access data from the sensors 2803, calculate an operation (e.g., to apply dorsiflexion stretch) of the actuators 2801, and transmit the calculated operation to the exosuit 2800. The user interface 2810 can additionally be configured to enable other functions; for example, the user interface 2810 can be configured to be used as a cellular telephone, a portable computer, an entertainment device, or to operate according to other applications.

The user interface 2810 can be configured to be removably mounted to the exosuit 2800 (e.g., by straps, magnets, Velcro, charging and/or data cables). Alternatively, the user interface 2810 can be configured as a part of the exosuit 2800 and not to be removed during normal operation. In some examples, a user interface can be incorporated as part of the exosuit 2800 (e.g., a touchscreen integrated into a sleeve of the exosuit 2800) and can be used to control and/or access information about the exosuit 2800 in addition to using the user interface 2810 to control and/or access information about the exosuit 2800. In some examples, the controller 2805 or other elements of the exosuit 2800 are configured to enable wireless or wired communication according to a standard protocol (e.g., Bluetooth, ZigBee, WiFi, LTE or other cellular standards, IRdA, Ethernet) such that a variety of systems and devices can be made to operate as the user interface 2810 when configured with complementary communications elements and computer-readable programs to enable such functionality.

The exosuit 2800 can be configured as described in example embodiments herein or in other ways according to an application. The exosuit 2800 can be operated to enable a variety of applications. The exosuit 2800 can be operated to enhance the strength of a wearer by detecting motions of the wearer (e.g., using sensors 2803) and responsively applying torques and/or forces to the body of the wearer (e.g., using actuators 2801) to increase the forces the wearer is able to apply to his/her body and/or environment. The exosuit 2800 can be operated to train a wearer to perform certain physical activities. For example, the exosuit 2800 can be operated to enable rehabilitative therapy of a wearer. The exosuit 2800 can operate to amplify motions and/or forces produced by a wearer undergoing therapy in order to enable the wearer to successfully complete a program of rehabilitative therapy. Additionally or alternatively, the exosuit 2800 can be operated to prohibit disordered movements of the wearer and/or to use the actuators 2801 and/or other elements (e.g., haptic feedback elements) to indicate to the wearer a motion or action to perform and/or motions or actions that should not be performed or that should be terminated. Similarly, other programs of physical training (e.g., dancing, skating, other athletic activities, vocational training) can be enabled by operation of the exosuit 2800 to detect motions, torques, or forces generated by a wearer and/or to apply forces, torques, or other haptic feedback to the wearer. Other applications of the exosuit 2800 and/or user interface 2810 are anticipated.

The user interface 2810 can additionally communicate with communications network(s) 2820. For example, the user interface 2810 can include a WiFi radio, an LTE transceiver or other cellular communications equipment, a wired modem, or some other elements to enable the user interface 2810 and exosuit 2800 to communicate with the Internet. The user interface 2810 can communicate through the communications network 2820 with a server 2830. Communication with the server 2830 can enable functions of the user interface 2810 and exosuit 2800. In some examples, the user interface 2810 can upload telemetry data (e.g., location, configuration of elements 2801, 2803 of the exosuit 2800, physiological data about a wearer of the exosuit 2800) to the server 2830.

In some examples, the server 2830 can be configured to control and/or access information from elements of the exosuit 2800 (e.g., 2801, 2803) to enable some application of the exosuit 2800. For example, the server 2830 can operate elements of the exosuit 2800 to move a wearer out of a dangerous situation if the wearer was injured, unconscious, or otherwise unable to move themselves and/or operate the exosuit 2800 and user interface 2810 to move themselves out of the dangerous situation. Other applications of a server in communications with a exosuit are anticipated.

The user interface 2810 can be configured to communicate with a second user interface 2845 in communication with and configured to operate a second flexible exosuit 2840. Such communication can be direct (e.g., using radio transceivers or other elements to transmit and receive information over a direct wireless or wired link between the user interface 2810 and the second user interface 2845). Additionally or alternatively, communication between the user interface 2810 and the second user interface 2845 can be facilitated by communications network(s) 2820 and/or a server 2830 configured to communicate with the user interface 2810 and the second user interface 2845 through the communications network(s) 2820.

Communication between the user interface 2810 and the second user interface 2845 can enable applications of the exosuit 2800 and second exosuit 2840. In some examples, actions of the exosuit 2800 and second flexible exosuit 2840 and/or of wearers of the exosuit 2800 and second exosuit 2840 can be coordinated. For example, the exosuit 2800 and second exosuit 2840 can be operated to coordinate the lifting of a heavy object by the wearers. The timing of the lift, and the degree of support provided by each of the wearers and/or the exosuit 2800 and second exosuit 2840 can be controlled to increase the stability with which the heavy object was carried, to reduce the risk of injury of the wearers, or according to some other consideration. Coordination of actions of the exosuit 2800 and second exosuit 2840 and/or of wearers thereof can include applying coordinated (in time, amplitude, or other properties) forces and/or torques to the wearers and/or elements of the environment of the wearers and/or applying haptic feedback (though actuators of the exosuits 2800, 2840, through dedicated haptic feedback elements, or through other methods) to the wearers to guide the wearers toward acting in a coordinated manner.

Coordinated operation of the exosuit 2800 and second exosuit 2840 can be implemented in a variety of ways. In some examples, one exosuit (and the wearer thereof) can act as a master, providing commands or other information to the other exosuit such that operations of the exosuit 2800, 2840 are coordinated. For example, the exosuit 2800, 2840 can be operated to enable the wearers to dance (or to engage in some other athletic activity) in a coordinated manner. One of the exosuits can act as the 'lead', transmitting timing or other information about the actions performed by the 'lead' wearer to the other exosuit, enabling coordinated dancing motions to be executed by the other wearer. In some examples, a first wearer of a first exosuit can act as a trainer, modeling motions or other physical activities that a second wearer of a second exosuit can learn to perform. The first exosuit can detect motions, torques, forces, or other physical activities executed by the first wearer and can send information related to the detected activities to the second exosuit. The second exosuit can then apply forces, torques, haptic feedback, or other information to the body of the second wearer to enable the second wearer to learn the motions or other physical activities modeled by the first wearer. In some examples, the server 2830 can send commands or other information to the exosuits 2800, 2840 to enable coordinated operation of the exosuits 2800, 2840.

The exosuit 2800 can be operated to transmit and/or record information about the actions of a wearer, the environment of the wearer, or other information about a wearer of the exosuit 2800. In some examples, kinematics related to motions and actions of the wearer can be recorded and/or sent to the server 2830. These data can be collected for medical, scientific, entertainment, social media, or other applications. The data can be used to operate a system. For example, the exosuit 2800 can be configured to transmit motions, forces, and/or torques generated by a user to a robotic system (e.g., a robotic arm, leg, torso, humanoid body, or some other robotic system) and the robotic system can be configured to mimic the activity of the wearer and/or to map the activity of the wearer into motions, forces, or torques of elements of the robotic system. In another example, the data can be used to operate a virtual avatar of the wearer, such that the motions of the avatar mirrored or were somehow related to the motions of the wearer. The virtual avatar can be instantiated in a virtual environment, presented to an individual or system with which the wearer is communicating, or configured and operated according to some other application.

Conversely, the exosuit 2800 can be operated to present haptic or other data to the wearer. In some examples, the actuators 2801 (e.g., twisted string actuators, exotendons) and/or haptic feedback elements (e.g., EPAM haptic elements) can be operated to apply and/or modulate forces applied to the body of the wearer to indicate mechanical or other information to the wearer. For example, the activation in a certain pattern of a haptic element of the exosuit 2800 disposed in a certain location of the exosuit 2800 can indicate that the wearer had received a call, email, or other communications. In another example, a robotic system can be operated using motions, forces, and/or torques generated by the wearer and transmitted to the robotic system by the exosuit 2800. Forces, moments, and other aspects of the environment and operation of the robotic system can be transmitted to the exosuit 2800 and presented (using actuators 2801 or other haptic feedback elements) to the wearer to enable the wearer to experience force-feedback or other haptic sensations related to the wearer's operation of the robotic system. In another example, haptic data presented to a wearer can be generated by a virtual environment, e.g., an environment containing an avatar of the wearer that is being operated based on motions or other data related to the wearer that is being detected by the exosuit 2800.

Note that the exosuit 2800 illustrated in FIG. 28 is only one example of a exosuit that can be operated by control electronics, software, or algorithms described herein. Control electronics, software, or algorithms as described herein can be configured to control flexible exosuits or other mechatronic and/or robotic system having more, fewer, or different actuators, sensors or other elements. Further, control electronics, software, or algorithms as described herein can be configured to control exosuits configured similarly to or differently from the illustrated exosuit 2800. Further, control electronics, software, or algorithms as described herein can be configured to control flexible exosuits having reconfigurable hardware (i.e., exosuits that are able to have actuators, sensors, or other elements added or removed) and/or to detect a current hardware configuration of the flexible exosuits using a variety of methods.

A controller of a exosuit and/or computer-readable programs executed by the controller can be configured to provide encapsulation of functions and/or components of the flexible exosuit. That is, some elements of the controller (e.g., subroutines, drivers, services, daemons, functions) can be configured to operate specific elements of the exosuit (e.g., a twisted string actuator, a haptic feedback element) and to allow other elements of the controller (e.g., other programs) to operate the specific elements and/or to provide abstracted access to the specific elements (e.g., to translate a command to orient an actuator in a commanded direction into a set of commands sufficient to orient the actuator in the commanded direction). This encapsulation can allow a variety of services, drivers, daemons, or other computer-readable programs to be developed for a variety of applications of a flexible exosuits. Further, by providing encapsulation of functions of a flexible exosuit in a generic, accessible manner (e.g., by specifying and implementing an application programming interface (API) or other interface standard), computer-readable programs can be created to interface with the generic, encapsulated functions such that the computer-readable programs can enable operating modes or functions for a variety of differently-configured exosuit, rather than for a single type or model of flexible exosuit. For example, a virtual avatar communications program can access information about the posture of a wearer of a flexible exosuit by accessing a standard exosuit API. Differently-configured exosuits can include different sensors, actuators, and other elements, but can provide posture information in the same format according to the API. Other functions and features of a flexible exosuit, or other robotic, exoskeletal, assistive, haptic, or other mechatronic system, can be encapsulated by APIs or according to some other standardized computer access and control interface scheme.

Figure 29:
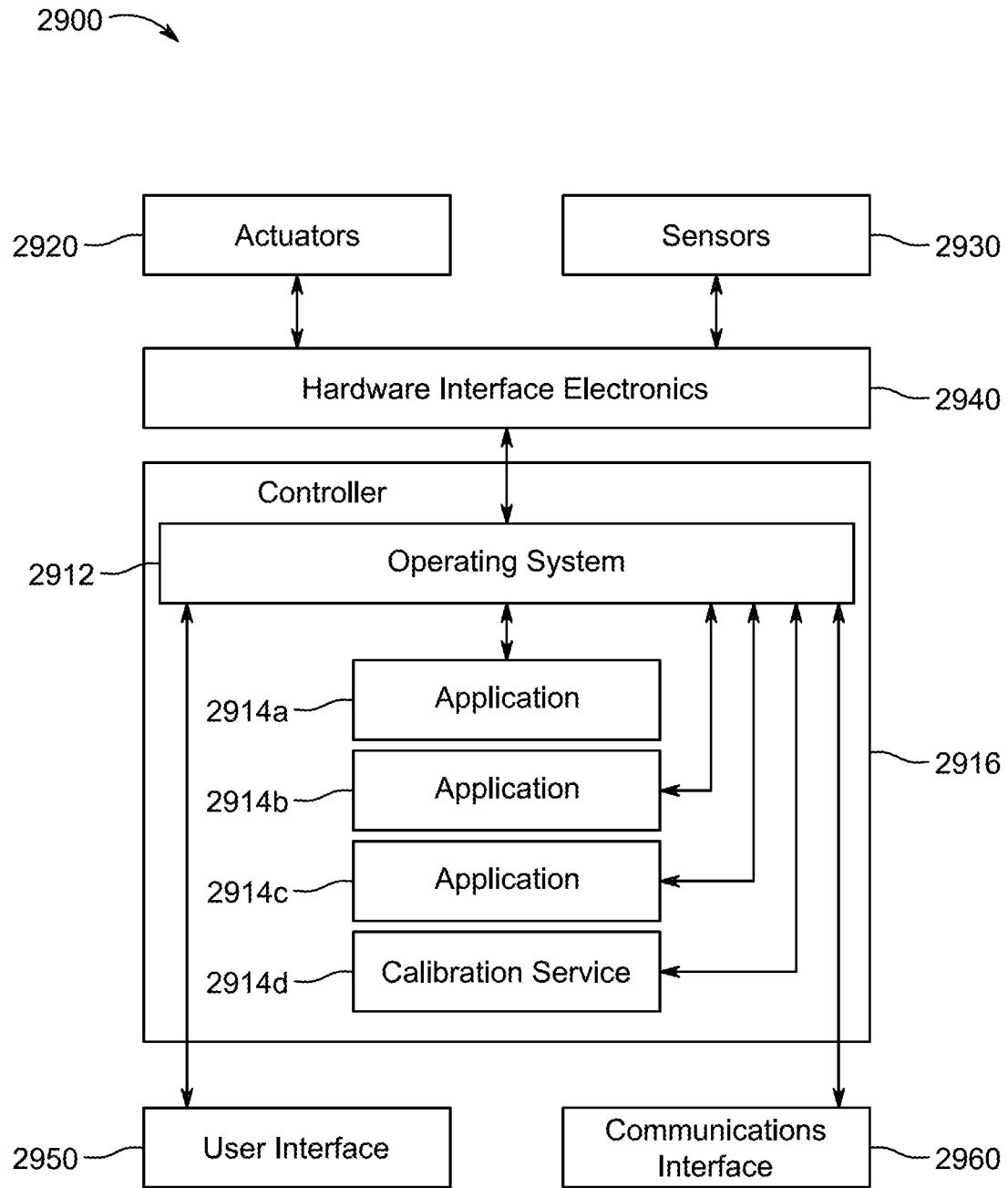
FIG. 29 is a schematic illustrating elements of a exosuit and a hierarchy of control or operating the exosuit according to an embodiment.

FIG. 29 is a schematic illustrating elements of a exosuit 2900 and a hierarchy of control or operating the exosuit 2900. The flexible exosuit includes actuators 2920 and sensors 2930 configured to apply forces and/or torques to and detect one or more properties of, respectively, the exosuit 2900, a wearer of the exosuit 2900, and/or the environment of the wearer. The exosuit 2900 additionally includes a controller 2910 configured to operate the actuators 2920 and sensors 2930 by using hardware interface electronics 2940. The hardware electronics interface 2940 includes electronics configured to interface signals from and to the controller 2910 with signals used to operate the actuators 2920 and sensors 2930. For example, the actuators 2920 can include exotendons, and the hardware interface electronics 2940 can include high-voltage generators, high-voltage switches, and high-voltage capacitance meters to clutch and un-clutch the exotendons and to report the length of the exotendons. The hardware interface electronics 2940 can include voltage regulators, high voltage generators, amplifiers, current detectors, encoders, magnetometers, switches, controlled-current sources, DACs, ADCs, feedback controllers, brushless motor controllers, or other electronic and mechatronic elements.

The controller 2910 additionally operates a user interface 2950 that is configured to present information to a user and/or wearer of the exosuit 2900 and a communications interface 2960 that is configured to facilitate the transfer of information between the controller 2910 and some other system (e.g., by transmitting a wireless signal). Additionally or alternatively, the user interface 2950 can be part of a separate system that is configured to transmit and receive user interface information to/from the controller 2910 using the communications interface 2960 (e.g., the user interface 2950 can be part of a cellphone).

The controller 2910 is configured to execute computer-readable programs describing functions of the flexible exosuit 2912. Among the computer-readable programs executed by the controller 2910 are an operating system 2912, applications 2914a, 2914b, 2914c, and a calibration service 2916. The operating system 2912 manages hardware resources of the controller 2910 (e.g., I/O ports, registers, timers, interrupts, peripherals, memory management units, serial and/or parallel communications units) and, by extension, manages the hardware resources of the exosuit 2900. The operating system 2912 is the only computer-readable program executed by the controller 2910 that has direct access to the hardware interface electronics 2940 and, by extension, the actuators 2920 and sensors 2930 of the exosuit 2900.

The applications 2914a, 2914b, 2914 are computer-readable programs that describe some function, functions, operating mode, or operating modes of the exosuit 2900. For example, application 2914a can describe a process for transmitting information about the wearer's posture to update a virtual avatar of the wearer that includes accessing information on a wearer's posture from the operating system 2912, maintaining communications with a remote system using the communications interface 2960, formatting the posture information, and sending the posture information to the remote system. The calibration service 2916 is a computer-readable program describing processes to store parameters describing properties of wearers, actuators 2920, and/or sensors 2930 of the exosuit 2900, to update those parameters based on operation of the actuators 2920, and/or sensors 2930 when a wearer is using the exosuit 2900, to make the parameters available to the operating system 2912 and/or applications 2914a, 2914b, 2914c, and other functions relating to the parameters. Note that applications 2914a, 2914b, 2914 and calibration service 2916 are intended as examples of computer-readable programs that can be run by the operating system 2912 of the controller 2910 to enable functions or operating modes of a exosuit 2900.

The operating system 2912 can provide for low-level control and maintenance of the hardware (e.g., 2920, 2930, 2940). In some examples, the operating system 2912 and/or hardware interface electronics 1540 can detect information about the exosuit 2900, the wearer, and/or the wearer's environment from one or more sensors 2930 at a constant specified rate. The operating system 2912 can generate an estimate of one or more states or properties of the exosuit 2900 or components thereof using the detected information. The operating system 2912 can update the generated estimate at the same rate as the constant specified rate or at a lower rate. The generated estimate can be generated from the detected information using a filter to remove noise, generate an estimate of an indirectly-detected property, or according to some other application. For example, the operating system 2912 can generate the estimate from the detected information using a Kalman filter to remove noise and to generate an estimate of a single directly or indirectly measured property of the exosuit 2900, the wearer, and/or the wearer's environment using more than one sensor. In some examples, the operating system can determine information about the wearer and/or exosuit 2900 based on detected information from multiple points in time. For example, the operating system 2900 can determine an eversion stretch and dorsiflexion stretch.

In some examples, the operating system 2912 and/or hardware interface electronics 2940 can operate and/or provide services related to operation of the actuators 2920. That is, in case where operation of the actuators 2920 requires the generation of control signals over a period of time, knowledge about a state or states of the actuators 2920, or other considerations, the operating system 2912 and/or hardware interface electronics 2940 can translate simple commands to operate the actuators 2920 (e.g., a command to generate a specified level of force using a twisted string actuator (TSA) of the actuators 2920) into the complex and/or state-based commands to the hardware interface electronics 2940 and/or actuators 2920 necessary to effect the simple command (e.g., a sequence of currents applied to windings of a motor of a TSA, based on a starting position of a rotor determined and stored by the operating system 2910, a relative position of the motor detected using an encoder, and a force generated by the TSA detected using a load cell).

In some examples, the operating system 2912 can further encapsulate the operation of the exosuit 2900 by translating a system-level simple command (e.g., a commanded level of force tension applied to the footplate) into commands for multiple actuators, according to the configuration of the exosuit 2900. This encapsulation can enable the creation of general-purpose applications that can effect a function of an exosuit (e.g., allowing a wearer of the exosuit to stretch his foot) without being configured to operate a specific model or type of exosuit (e.g., by being configured to generate a simple force production profile that the operating system 2912 and hardware interface electronics 2940 can translate into actuator commands sufficient to cause the actuators 2920 to apply the commanded force production profile to the footplate).

The operating system 2912 can act as a standard, multi-purpose platform to enable the use of a variety of exosuits having a variety of different hardware configurations to enable a variety of mechatronic, biomedical, human interface, training, rehabilitative, communications, and other applications. The operating system 2912 can make sensors 2930, actuators 2920, or other elements or functions of the exosuit 2900 available to remote systems in communication with the exosuit 2900 (e.g., using the communications interface 2960) and/or a variety of applications, daemons, services, or other computer-readable programs being executed by operating system 2912. The operating system 2912 can make the actuators, sensors, or other elements or functions available in a standard way (e.g., through an API, communications protocol, or other programmatic interface) such that applications, daemons, services, or other computer-readable programs can be created to be installed on, executed by, and operated to enable functions or operating modes of a variety of flexible exosuits having a variety of different configurations. The API, communications protocol, or other programmatic interface made available by the operating system 2912 can encapsulate, translate, or otherwise abstract the operation of the exosuit 2900 to enable the creation of such computer-readable programs that are able to operate to enable functions of a wide variety of differently-configured flexible exosuits.

Additionally or alternatively, the operating system 2912 can be configured to operate a modular flexible exosuit system (i.e., a flexible exosuit system wherein actuators, sensors, or other elements can be added or subtracted from a flexible exosuit to enable operating modes or functions of the flexible exosuit). In some examples, the operating system 2912 can determine the hardware configuration of the exosuit 2900 dynamically and can adjust the operation of the exosuit 2900 relative to the determined current hardware configuration of the exosuit 2900. This operation can be performed in a way that was 'invisible' to computer-readable programs (e.g., 2914a, 2914b, 2914c) accessing the functionality of the exosuit 2900 through a standardized programmatic interface presented by the operating system 2912. For example, the computer-readable program can indicate to the operating system 2912, through the standardized programmatic interface, that a specified level of torque was to be applied to an ankle of a wearer of the exosuit 2900. The operating system 2912 can responsively determine a pattern of operation of the actuators 2920, based on the determined hardware configuration of the exosuit 2900, sufficient to apply the specified level of torque to the ankle of the wearer.

In some examples, the operating system 2912 and/or hardware interface electronics 2940 can operate the actuators 2920 to ensure that the exosuit 2900 does not operate to directly cause the wearer to be injured and/or elements of the exosuit 2900 to be damaged. In some examples, this can include not operating the actuators 2920 to apply forces and/or torques to the body of the wearer that exceeded some maximum threshold. This can be implemented as a watchdog process or some other computer-readable program that can be configured (when executed by the controller 2910) to monitor the forces being applied by the actuators 2920 (e.g., by monitoring commands sent to the actuators 2920 and/or monitoring measurements of forces or other properties detected using the sensors 2930) and to disable and/or change the operation of the actuators 2920 to prevent injury of the wearer. Additionally or alternatively, the hardware interface electronics 2940 can be configured to include circuitry to prevent excessive forces and/or torques from being applied to the wearer (e.g., by channeling to a comparator the output of a load cell that is configured to measure the force generated by a TSA, and configuring the comparator to cut the power to the motor of the TSA when the force exceeded a specified level).

In some examples, operating the actuators 2920 to ensure that the exosuit 2900 does not damage itself can include a watchdog process or circuitry configured to prevent over-current, over-load, over-rotation, or other conditions from occurring that can result in damage to elements of the exosuit 2900. For example, the hardware interface electronics 2940 can include a metal oxide varistor, breaker, shunt diode, or other element configured to limit the voltage and/or current applied to a winding of a motor.

Note that the above functions described as being enabled by the operating system 2912 can additionally or alternatively be implemented by applications 2914a, 2914b, 2914c, services, drivers, daemons, or other computer-readable programs executed by the controller 2900. The applications, drivers, services, daemons, or other computer-readable programs can have special security privileges or other properties to facilitate their use to enable the above functions.

The operating system 2912 can encapsulate the functions of the hardware interface electronics 2940, actuators 2920, and sensors 2930 for use by other computer-readable programs (e.g., applications 2914a, 2914b, 2914c, calibration service 2916), by the user (through the user interface 2950), and/or by some other system (i.e., a system configured to communicate with the controller 2910 through the communications interface 2960). The encapsulation of functions of the exosuit 2900 can take the form of application programming interfaces (APIs), i.e., sets of function calls and procedures that an application running on the controller 2910 can use to access the functionality of elements of the exosuit 2900. In some examples, the operating system 2912 can make available a standard 'exosuit API' to applications being executed by the controller 2910. The 'exosuit API' can enable applications 2914a, 2914b, 2914c to access functions of the exosuit 2900 without requiring those applications 2914a, 2914b, 2914c to be configured to generate whatever complex, time-dependent signals are necessary to operate elements of the exosuit 2900 (e.g., actuators 2920, sensors 2930).

The 'exosuit API' can allow applications 2914a, 2914b, 2914c to send simple commands to the operating system 2912 (e.g., 'begin storing mechanical energy from the ankle of the wearer when the foot of the wearer contacts the ground') in such that the operating system 2912 can interpret those commands and generate the command signals to the hardware interface electronics 2940 or other elements of the exosuit 2900 that are sufficient to effect the simple commands generated by the applications 2914a, 2914b, 2914c (e.g., determining whether the foot of the wearer has contacted the ground based on information detected by the sensors 2930, responsively applying high voltage to an exotendon that crosses the user's ankle).

The 'exosuit API' can be an industry standard (e.g., an ISO standard), a proprietary standard, an open-source standard, or otherwise made available to individuals that can then produce applications for exosuits. The 'exosuit API' can allow applications, drivers, services, daemons, or other computer-readable programs to be created that are able to operate a variety of different types and configurations of exosuits by being configured to interface with the standard 'exosuit API' that is implemented by the variety of different types and configurations of exosuits. Additionally or alternatively, the 'exosuit API' can provide a standard encapsulation of individual exosuit-specific actuators (i.e., actuators that apply forces to specific body segments, where differently-configured exosuits may not include an actuator that applies forces to the same specific body segments) and can provide a standard interface for accessing information on the configuration of whatever exosuit is providing the 'exosuit API'. An application or other program that accesses the 'exosuit API' can access data about the configuration of the exosuit (e.g., locations and forces between body segments generated by actuators, specifications of actuators, locations and specifications of sensors) and can generate simple commands for individual actuators (e.g., generate a force of 30 newtons for 50 milliseconds) based on a model of the exosuit generated by the application and based on the information on the accessed data about the configuration of the exosuit. Additional or alternate functionality can be encapsulated by an 'exosuit API' according to an application.

Applications 2914a, 2914b, 2914c can individually enable all or parts of the functions and operating modes of a flexible exosuit described herein. For example, an application can enable haptic control of a robotic system by transmitting postures, forces, torques, and other information about the activity of a wearer of the exosuit 2900 and by translating received forces and torques from the robotic system into haptic feedback applied to the wearer (i.e., forces and torques applied to the body of the wearer by actuators 2920 and/or haptic feedback elements). In another example, an application can enable a wearer to locomote more efficiently by submitting commands to and receiving data from the operating system 2912 (e.g., through an API) such that actuators 2920 of the exosuit 2900 assist the movement of the user, extract negative work from phases of the wearer's locomotion and inject the stored work to other phases of the wearer's locomotion, or other methods of operating the exosuit 2900. Applications can be installed on the controller 2910 and/or on a computer-readable storage medium included in the exosuit 2900 by a variety of methods. Applications can be installed from a removable computer-readable storage medium or from a system in communication with the controller 2910 through the communications interface 2960. In some examples, the applications can be installed from a web site, a repository of compiled or un-compiled programs on the Internet, an online store (e.g., Google Play, iTunes App Store), or some other source. Further, functions of the applications can be contingent upon the controller 2910 being in continuous or periodic communication with a remote system (e.g., to receive updates, authenticate the application, to provide information about current environmental conditions).

The exosuit 2900 illustrated in FIG. 29 is intended as an illustrative example. Other configurations of flexible exosuits and of operating systems, kernels, applications, drivers, services, daemons, or other computer-readable programs are anticipated. For example, an operating system configured to operate an exosuit can include a real-time operating system component configured to generate low-level commands to operate elements of the exosuit and a non-real-time component to enable less time-sensitive functions, like a clock on a user interface, updating computer-readable programs stored in the exosuit, or other functions. A exosuit can include more than one controller; further, some of those controllers can be configured to execute real-time applications, operating systems, drivers, or other computer-readable programs (e.g., those controllers were configured to have very short interrupt servicing routines, very fast thread switching, or other properties and functions relating to latency-sensitive computations) while other controllers are configured to enable less time-sensitive functions of a flexible exosuit. Additional configurations and operating modes of an exosuit are anticipated. Further, control systems configured as described herein can additionally or alternatively be configured to enable the operation of devices and systems other than exosuit; for example, control systems as described herein can be configured to operate robots, rigid exosuits or exoskeletons, assistive devices, prosthetics, or other mechatronic devices.

Control of actuators of an exosuit can be implemented in a variety of ways according to a variety of control schemes. Generally, one or more hardware and/or software controllers can receive information about the state of the flexible exosuit, a wearer of the exosuit, and/or the environment of the exosuit from sensors disposed on or within the exosuit and/or a remote system in communication with the exosuit. The one or more hardware and/or software controllers can then generate a control output that can be executed by actuators of the exosuit to affect a commanded state of the exosuit and/or to enable some other application. One or more software controllers can be implemented as part of an operating system, kernel, driver, application, service, daemon, or other computer-readable program executed by a processor included in the exosuit.

In some embodiments, a powered assistive exosuit intended primarily for assistive functions can also be adapted to perform exosuit functions. In one embodiment, an assistive exosuit similar to the embodiments described in U.S. patent application publication no. 2018/0056104, titled "Systems and Methods for Assistive Exosuit System,", that is used for assistive functions may be adapted to perform exosuit functions. Embodiments of such an assistive exosuit typically include FLAs approximating muscle groups such as hip flexors, gluteal/hip extensors, spinal extensors, or abdominal muscles. In the assistive modes of these exosuits, these FLAs provide assistance for activities such as moving between standing and seated positions, walking, and postural stability. Actuation of specific FLAs within such an exosuit system may also provide stretching assistance. Typically, activation of one or more FLAs approximating a muscle group can stretch the antagonist muscles. For example, activation of one or more FLAs approximating the abdominal muscles might stretch the spinal extensors, or activation of one or more FLAs approximating gluteal/hip extensor muscles can stretch the hip flexors. The exosuit may be adapted to detect when the wearer is ready to initiate a stretch and perform an automated stretching regimen; or the wearer may indicate to the suit to initiate a stretching regimen.

It can be appreciated that assistive exosuits may have multiple applications. Assistive exosuits may be prescribed for medical applications. These may include therapeutic applications, such as assistance with exercise or stretching regimens for rehabilitation, disease mitigation or other therapeutic purposes. Mobility-assistance devices such as wheelchairs, walkers, crutches and scooters are often prescribed for individuals with mobility impairments. Likewise, an assistive exosuit may be prescribed for mobility assistance for patients with mobility impairments. Compared with mobility assistance devices such as wheelchairs, walkers, crutches and scooters, an assistive exosuit may be less bulky, more visually appealing, and conform with activities of daily living such as riding in vehicles, attending community or social functions, using the toilet, and common household activities.

An assistive exosuit may additionally function as primary apparel, fashion items or accessories. The exosuit may be stylized for desired visual appearance. The stylized design may reinforce visual perception of the assistance that the exosuit is intended to provide. For example, an assistive exosuit intended to assist with torso and upper body activities may present a visual appearance of a muscular torso and upper body. Alternatively, the stylized design may be intended to mask or camouflage the functionality of the assistive exosuit through design of the base layer, electro/mechanical integration or other design factors.

Similarly to assistive exosuits intended for medically prescribed mobility assistance, assistive exosuits may be developed and utilized for non-medical mobility assistance, performance enhancement and support. For many, independent aging is associated with greater quality of life, however activities may become more limited with time due to normal aging processes. An assistive exosuit may enable aging individuals living independently to electively enhance their abilities and activities. For example, gait or walking assistance could enable individuals to maintain routines such as social walking or golf Postural assistance may render social situations more comfortable, with less fatigue. Assistance with transitioning between seated and standing positions may reduce fatigue, increase confidence, and reduce the risk of falls. These types of assistance, while not explicitly medical in nature, may enable more fulfilling, independent living during aging processes.

Athletic applications for an assistive exosuit are also envisioned. In one example, an exosuit may be optimized to assist with a particular activity, such as cycling. In the cycling example, FLAs approximating gluteal or hip extensor muscles may be integrated into bicycle clothing, providing assistance with pedaling. The assistance could be varied based on terrain, fatigue level or strength of the wearer, or other factors. The assistance provided may enable increased performance, injury avoidance, or maintenance of performance in the case of injury or aging. It can be appreciated that assistive exosuits could be optimized to assist with the demands of other sports such as running, jumping, swimming, skiing, or other activities. An athletic assistive exosuit may also be optimized for training in a particular sport or activity. Assistive exosuits may guide the wearer in proper form or technique, such as a golf swing, running stride, skiing form, swimming stroke, or other components of sports or activities. Assistive exosuits may also provide resistance for strength or endurance training. The provided resistance may be according to a regimen, such as high intensity intervals.

Assistive exosuit systems as described above may also be used in gaming applications. Motions of the wearer, detected by the suit, may be incorporated as a game controller system. For example, the suit may sense wearer's motions that simulate running, jumping, throwing, dancing, fighting, or other motions appropriate to a particular game. The suit may provide haptic feedback to the wearer, including resistance or assistance with the motions performed or other haptic feedback to the wearer.

Assistive exosuits as described above may be used for military or first responder applications. Military and first responder personnel are often to be required to perform arduous work where safety or even life may be at stake. An assistive exosuit may provide additional strength or endurance as required for these occupations. An assistive exosuit may connect to one or more communication networks to provide communication services for the wearer, as well as remote monitoring of the suit or wearer.

Assistive exosuits as described above may be used for industrial or occupational safety applications. Exosuits may provide more strength or endurance for specific physical tasks such as lifting or carrying or repetitive tasks such as assembly line work. By providing physical assistance, assistive exosuits may also help avoid or prevent occupational injury due overexertion or repetitive stress.

Assistive exosuits as described above may also be configured as home accessories. Home accessory assistive exosuits may assist with household tasks such as cleaning or yard work, or may be used for recreational or exercise purposes. The communication capabilities of an assistive exosuit may connect to a home network for communication, entertainment or safety monitoring purposes.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art can appreciate that the conception, upon which this disclosure is based, may readily be utilized as a basis for the designing of other structures, systems, methods and media for carrying out the several purposes of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

What is claimed is:

1. A pelvis load distribution system, comprising:
    a first member comprising first and second interfacing regions, a first rigid member, and a first plurality of anchor stays mounted above the first rigid member;
    a second member comprising third and fourth interfacing regions, a second rigid member, and a second plurality of anchor stays mounted above the second rigid member; and
    a third member comprising fifth and sixth interfacing regions, a third rigid member, and a third plurality of anchor stays mounted above the third rigid member;
    wherein the first, second, and third members interconnect to form a three part loop having an adjustable fit that enables the three part loop to be secured around a pelvis of a human being.

2. The system of claim 1, wherein the three part loop is formed when the first member is coupled to the third member, the third member is coupled to the second member, and the second member is coupled to the first member.

3. The system of claim 1, wherein interconnection among the first, second, and third members is operable to accept a plurality of rotation combinations between any interfacing members to accommodate different shapes of the pelvis.

4. The system of claim 1, wherein interconnection among the first, second, and third members is operable to accept a plurality of varied length combinations between any interfacing members to accommodate different sizes of the pelvis.

5. The system of claim 1, wherein the first and second, and third plurality of anchor stays are operative to interface with respective flexdrive components.

6. The system of claim 1, wherein the first and second interfacing regions are located at respective distal ends of the first member, wherein the third and fourth interfacing regions are located at respective distal ends of the second member, wherein the fifth and sixth interfacing regions are located at respective distal ends of the third member.

7. The system of claim 1, wherein the first member includes first and second sides, wherein the first and second interfacing regions are located on the first side, and wherein the first plurality of anchor stays are located on the second side;
    wherein the second member includes third and fourth sides, wherein the third interfacing region is located on the third side, wherein the fourth interfacing region is located on the fourth side, and wherein the second plurality of anchor stays are located on the third side; and
    wherein the third member includes fifth and sixth sides, wherein the fifth and sixth interfacing regions are located on the fifth side, and wherein the third plurality of anchor stays are located on the fifth side.

8. The system of claim 7, wherein the first rigid member is integrated within the first member between the first and second sides, wherein the second rigid member is integrated within the second member between the third and fourth sides, and wherein the third rigid member is integrated within the third member between the fifth and sixth sides.

9. The system of claim 1, wherein the first member further comprises a first flange member that defines a periphery of the first member, wherein the second member further comprises a second flange member that defines a periphery of the second member, and wherein the third member further comprises a third flange member that defines a periphery of the third member.

10. A thigh load distribution system, comprising:
a first member comprising first and second interfacing regions and a first stay region, wherein the first interface region is located on an exterior side of the first member and wherein the second interfacing region is located on an interior side of the first member; and
a second member comprising third and fourth interfacing regions and a second stay region, wherein the third interface region is located on an exterior side of the second member and wherein the fourth interfacing region is located on an interior side of the first member;
wherein the first and second members interconnect to form a two part loop having an adjustable fit that enables the two part loop to be secured around a thigh of a human being.

11. The system of claim 10, wherein the two part loop is formed when the second interfacing member is coupled to the third interfacing member, and the first interfacing member is coupled to the fourth interfacing member.

12. The system of claim 10, wherein interconnection among the first and second members is operable to accept a plurality of rotation combinations to accommodate different shapes of the pelvis.

13. The system of claim 10, wherein interconnection among the first and second members is operable to accept a plurality of varied length combinations to accommodate different sizes of the pelvis.

14. The system of claim 10, wherein the first and second stays are operative to interface with respective flexdrive components.

15. The system of claim 10, wherein the first, second, third, and fourth interfacing members are hook and loop interfacing members.

16. A thigh load distribution system, comprising:
flange member;
stay region secured to the flange member;
first no stretch member secured on top of the stay region and the flange member;
first and second interfacing regions secured on top of the first no stretch member;
third interfacing region secured below the flange member; and
adjustment member secured to the first no stretch member, the adjustment member comprising:
a stretch member secured to the first no stretch member;
a second no stretch member secured to the stretch member; and
a fourth interfacing member secured to the second no stretch member;
wherein the first and second interfacing members are coupled together to establish a first loop connection around a thigh of a human, and wherein the fourth and third interfacing members are coupled together to establish a second loop connection around the thigh.

17. The system of claim 16, wherein the second stretch region provides flexibility in establishing a desired tightness fit of the second loop connection.

18. The system of claim 16, further comprising:
at least one flexdrive component coupled to the first no stretch member above the stay region.

19. The system of claim 16, wherein the first, second, third, and fourth interfacing members comprise hook and loop interfaces.

* * * * *